United States Patent [19]

Ohyama et al.

[11] Patent Number: 4,752,326
[45] Date of Patent: Jun. 21, 1988

[54] 1-ARYLPYRAZOLES, COMPOSITION CONTAINING THEM, AND HERBICIDAL METHOD OF USING THEM

[75] Inventors: Hiroshi Ohyama, Chigasak; Toshiharu Ono, Atsugi; Takuro Shimozono, Atsugi; Teruhiko Terakawa, Atsugi, all of Japan

[73] Assignee: Hokko Chemical Industry Co., Ltd., Tokyo, Japan

[21] Appl. No.: 860,870

[22] Filed: May 8, 1986

[30] Foreign Application Priority Data

May 15, 1985 [JP] Japan ................................. 60-101459
Oct. 1, 1985 [JP] Japan ................................. 60-216163

[51] Int. Cl.$^4$ .................. A01N 43/56; C07D 231/36; C07D 231/38; C07D 231/52
[52] U.S. Cl. ........................................ 71/92; 548/362; 548/373; 548/375; 548/376; 548/377; 548/378
[58] Field of Search .............. 548/362, 373, 375, 376, 548/377, 378, 369; 71/92

[56] References Cited

U.S. PATENT DOCUMENTS

| | | | |
|---|---|---|---|
| 3,869,274 | 3/1975 | Crovetti et al. | 548/375 |
| 4,059,434 | 11/1977 | Wolf | 548/369 |
| 4,124,373 | 11/1978 | Wolf | 548/369 |
| 4,124,374 | 11/1978 | Wolf | 548/369 |
| 4,624,699 | 11/1986 | Nagano et al. | 548/369 |
| 4,666,507 | 5/1987 | Yanagi et al. | 548/375 |

Primary Examiner—Richard A. Schwartz
Assistant Examiner—Kurt G. Briscoe
Attorney, Agent, or Firm—Larson and Taylor

[57] ABSTRACT

As compounds is provided a pyrazole derivative of the formula

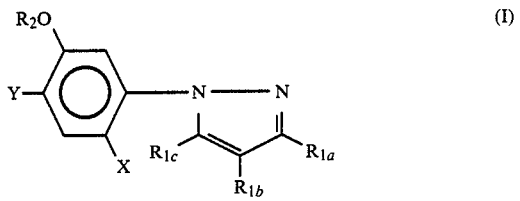

wherein $R_{1a}$, $R_{1b}$ and $R_{1c}$ are each a hydrogen atom, a halogen atom, a nitro group, an amino group, a (lower) alkyl group, a halo-(lower)alkyl group, a(lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group;

$R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lowr)alkyl group, a (lower) alkoxycarbonyl(lower)alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower) alkyl-substituted phenylsulfonyl group, and X and Y are the same or different and each are a halogen atom. The pyrazoles are useful as herbicidal agent and may be produced by a variety of processes.

15 Claims, No Drawings

1-ARYLPYRAZOLES, COMPOSITION CONTAINING THEM, AND HERBICIDAL METHOD OF USING THEM

SUMMARY OF THE INVENTION

This invention relates to pyrazole derivatives which are useful as the herbicidal agent, processes of producing these pyrazole derivatives and also uses of these pyrazole derivatives. More particularly, this invention relates to a N-arylpyrazole derivative represented by the general formula (I) given hereinafter, as well as a herbicidal composition comprising said N-aryl pyrazole derivative as active ingredient. This invention further relates to processes for the production of said N-arylpyrazole derivatives.

BACKGROUND OF THE INVENTION

Certain kinds of pyrazole derivatives are already known to exhibit such physiological activities utilizable as agricultural chemicals. For instance, Japanese patent publication No. 19958/65 discloses that a class of N-phenylpyrazole derivatives represented by the formula

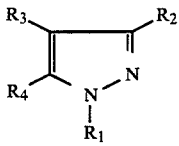

wherein $R_1$ is a hydrogen atom or phenyl group, $R_2$ is a hydrogen atom or a (lower)alkyl group, $R_3$ is a hydrogen atom, nitro group or cyano group and $R_4$ is a (lower)alkyl group, amino group or a (lower)alkoxy group shows herbicidal activity. Besides, Japanese patent publication No. 14833/67 discloses that an N-(nitro-substituted phenyl) pyrazole derivative or an N-(chloronitro-substituted phenyl)pyrazole derivative represented by the general formula

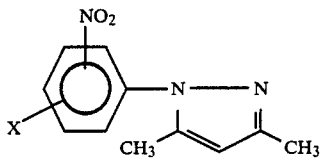

wherein X is Cl or H exhibits fungicidal activity and is useful to control fungicidal infections in crop-plants such as tomato, rice and kidney bean. Nonetheless, such N-phenylpyrazole derivatives of which the phenyl nucleus is bearing halogen atoms at the 2- and 4-positions and a hydroxy group or substituted hydroxy group at the 5-position in accordance with this invention, as be seen with the new compounds of this invention, have never been known before our invention, as far as we are aware of.

The known particular pyrazole derivatives according to the Japanese patent publication No. 19958/65 and No. 14833/67 can exhibit no or little herbicidal activity and are practically not useful as the herbicidal agent. Accordingly, we have made our researches in an attempt to provide such new pyrazole derivatives which show remarkably higher herbicidal activities than the above-mentioned known particular pyrazole derivatives, and which are practicably utilizable as the herbicidal agent for irrigated field of aquatic rice plant and also as the herbicidal agent for farm-fields (non-irrigated) for various kinds of crop-plants.

DETAILED DESCRIPTION OF THE INVENTION

With the above-mentioned attempt, we have synthetized a number of pyrazole derivatives and researched the utilities of the pyrazole derivatives so synthetized. As result, we have now found that a class of N-phenylpyrazole derivatives represented by the general formula (I) as given hereinafter is new compounds which have never been disclosed in any literatures and that these new N-phenyl pyrazole derivatives of the general formula (I) exhibit significantly high herbicidal activity and are useful as a herbicidal agent in practice.

According to a first aspect of this invention, therefore, there is provided a pyrazole derivative represented by the general formula

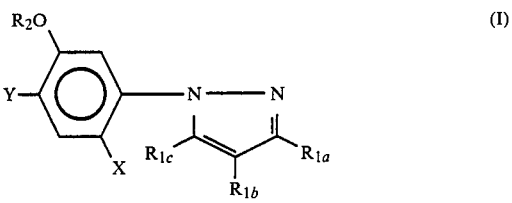

wherein $R_{1a}$, $R_{1b}$ and $R_{1c}$ are each a hydrogen atom, a halogen atom, a nitro group, an amino group, a (lower) alkyl group, a halo-(lower)alkyl group, a (lower)alkenyl group, a (lower)alkynyl group, a (lower)alkylcarbonylamino group, a (lower)alkoxycarbonylamino group, a mono(lower)alkylaminocarbonylamino group or a di-(lower) alkylaminocarbonylamino group;

$R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower) alkoxycarbonyl(lower)alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower) alkyl-substituted phenylsulfonyl group, and X and Y are the same or different and each are a halogen atom.

According to a second aspect of this invention, there is provided a herbicidal composition comprising an N-phenylpyrazole derivative of the above general formula (I), as active ingredient, in association with a solid or liquid carrier for the active ingredient.

According to a third aspect of this invention, there is provided a method of inhibiting the growth of unwanted weeds, which comprises applying to the weeds or to the locus of the weeds a herbicidally effective amount of the N-phenylpyrazole derivative of the general formula (I) as above.

In this specification, the term "(lower)alkyl group" appears in the terms "(lower)alkyl group", "(lower)alkylthio(lower)alkyl group", "cyano-(lower) alkyl group" and other terminologies which are shown by $R_{1a}$, $R_{1b}$, $R_{1c}$ and $R_2$ in the general formula (I) representing the new compounds of this invention. By the term "(lower)alkyl group" is herein meant an alkyl group of 1 to 6 carbon atoms, such as methyl, ethyl, propyl, isopropyl, butyl, isobutyl, sec-butyl, tert.butyl, pentyl, hexyl, isohexyl and the like. By the term "(lower)alkenyl group" which is shown by $R_{1a}$, $R_{1b}$ and $R_{1c}$ as well as by $R_2$ in the formula (I) is an alkenyl group containing 2 to 6 carbon atoms, such as vinyl, allyl, 1-propenyl, 2-methyl-2-propenyl, 1-methyl-2-propenyl, 2-butenyl, 3-butenyl, 2-pentenyl, 2,4-hexadienyl and the like. By the term "(lower)alkynyl group" is meant an alkynyl group containing 2 to 6 carbon atoms, such as ethynyl, 2-propynyl (or propargyl), 1-methyl-2-propynyl, 2-butynyl, 1-methyl-2-butynyl and the like. The halogen atom for X and Y as well as $R_{1a}$, $R_{1b}$ and $R_{1c}$ may be Cl, Br, F and I. Thus, the substituents $R_{1a}$, $R_{1b}$, $R_{1c}$, $R_2$, X and Y in the general formula (I) above may take any combinations of the above-mentioned particular values of these substituents of various sorts.

Particular examples of the new compound of the general formula (I) according to the first aspect of this invention are listed in Table 1 below.

TABLE 1

| Compound No. | $R_{1a}$, $R_{1b}$, $R_{1c}$ | $R_2$ | X | Y | Melting point (°C.) or refractive index ($n_D^{23}$) |
|---|---|---|---|---|---|
| 1 | 3-$CF_3$— | $C_2H_5$— | Cl | F | $n_D^{23}$ 1.4835 |
| 2 | 4-$NO_2$— | i-$C_3H_7$— | Cl | Cl | $n_D^{23}$ 1.4856 |
| 3 | 4-$NH_2$— | i-$C_3H_7$— | Cl | Cl | $n_D^{23}$ 1.4769 |
| 4 | 4-n-$C_3H_7$OCONH— | i-$C_3H_7$— | Cl | Cl | $n_D^{23}$ 1.4901 |
| 5 | 3-$CH_3$—5-$CF_3$— | n-$C_4H_9$— | F | Cl | $n_D^{23}$ 1.4889 |
| 6 | 3-$CF_3$—5-$CH_3$— | i-$C_3H_7$— | F | Cl | $n_D^{23}$ 1.4823 |
| 7 | 3-$CF_3$—5-$CH_3$— | $CH_3SO_2$— | F | Cl | mp. 95–98 |
| 8 | 3-$CH_3$—4-$NO_2$— | n-$C_3H_7$— | F | Cl | $n_D^{23}$ 1.4935 |
| 9 | 3-$CH_3$—4-$NO_2$— | n-$C_6H_{13}$ | F | Cl | $n_D^{23}$ 1.4926 |
| 10 | 3-$CH_3$—4-$NO_2$— | $CH_2$=CH—CH(—)—$CH_3$ | F | Cl | $n_D^{23}$ 1.4909 |
| 11 | 3-$C_2H_5$—4-$NO_2$— | $C_2H_5$— | F | Cl | $n_D^{23}$ 1.4911 |
| 12 | 3-$C_2H_5$—4-$NO_2$— | n-$C_3H_7$— | F | Br | $n_D^{23}$ 1.4916 |
| 13 | 3-$CH_3$—4-$NH_2$— | i-$C_3H_7$— | F | Cl | $n_D^{23}$ 1.4951 |
| 14 | 3-$CH_3$—4-n-$C_3H_7$CONH— | i-$C_3H_7$— | F | Cl | $n_D^{23}$ 1.4918 |
| 15 | 3-$CF_3$—4-Cl— | $C_2H_5$— | F | Cl | $n_D^{23}$ 1.4965 |
| 16 | 3-$CF_3$—5-Cl— | i-$C_3H_7$— | F | Cl | $n_D^{23}$ 1.4927 |
| 17 | 4-$NO_2$—5-Cl— | i-$C_3H_7$— | Cl | F | $n_D^{23}$ 1.4902 |
| 18 | 3,5-$(CF_3)_2$— | H— | F | Cl | $n_D^{23}$ 1.4656 |
| 19 | 3,5-$(CF_3)_2$— | i-$C_3H_7$— | F | Cl | $n_D^{23}$ 1.4634 |
| 20 | 3,5-$(CF_3)_2$— | $CH_2$=C(—$CH_3$)—$CH_2$— | F | Cl | $n_D^{23}$ 1.4630 |
| 21 | 3,5-$(CF_3)_2$— | HC≡C$CH_2$— | F | Cl | mp. 45–47 |
| 22 | 3,5-$(CF_3)_2$ | n-$C_4H_9$—O$CH_2CH_2$— | F | Cl | $n_D^{23}$ 1.4688 |
| 23 | 3,5-$(CF_3)_2$— | $CH_3$CO$CH_2$— | F | Cl | $n_D^{23}$ 1.4675 |
| 24 | 3,5-$(CF_3)_2$— | NC—CH(—$CH_3$)— | F | Cl | $n_D^{23}$ 1.4728 |
| 25 | 3,5-$(CF_3)_2$— | $CH_3SO_2$— | F | Cl | mp. 87–89.5 |
| 26 | 3,5-$(CF_3)_2$— | $CH_3$—C$_6H_4$—$SO_2$— | F | Cl | $n_D^{23}$ 1.4801 |
| 27 | 3,5-$(CF_3)_2$— | i-$C_3H_7$— | Cl | Cl | $n_D^{23}$ 1.5478 |
| 28 | 3,5-$(CF_3)_2$— | i-$C_3H_7$— | Cl | Br | $n_D^{23}$ 1.4964 |
| 29 | 3,5-$(CF_3)_2$— | i-$C_3H_7$— | Br | Cl | $n_D^{23}$ 1.5062 |
| 30 | 3-$CF_3$—4-$NO_2$— | i-$C_3H_7$— | F | Cl | $n_D^{23}$ 1.4935 |
| 31 | 3-$CF_3$—4-$NH_2$— | i-$C_3H_7$— | F | Cl | $n_D^{23}$ 1.4918 |
| 32 | 3-$CF_3$—4-$C_2H_5$NHCONH— | i-$C_3H_7$— | F | Cl | $n_D^{23}$ 1.5114 |
| 33 | 3,5-$(CH_3)_2$—4-$CF_3$— | i-$C_3H_7$— | F | Cl | $n_D^{23}$ 1.5106 |
| 34 | 3,5-$(CH_3)_2$—4-$CF_3$— | HC≡C$CH_2$— | F | Cl | $n_D^{23}$ 1.5092 |
| 35 | 3-$CF_3$—4-$C_2H_5$—5-$CH_3$— | i-$C_3H_7$— | F | Cl | $n_D^{23}$ 1.5118 |
| 36 | 3-$CF_3$—4-n-$C_4H_9$—5-$CH_3$— | i-$C_3H_7$— | F | Cl | $n_D^{23}$ 1.5110 |
| 37 | 3,5-$(CH_3)_2$—4-$NO_2$— | H— | F | Cl | mp. 157–158 |
| 38 | 3,5-$(CH_3)_2$—4-$NO_2$— | $CH_3$— | F | Cl | mp. 151.5–153 |
| 39 | 3,5-$(CH_3)_2$—4-$NO_2$— | $C_2H_5$— | F | Cl | mp. 135.5–136.5 |

TABLE 1-continued

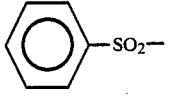

| Compound No. | $R_{1a}, R_{1b}, R_{1c}$ | $R_2$ | X | Y | Melting point (°C.) or refractive index ($n_D^{23}$) |
|---|---|---|---|---|---|
| 40 | 3,5-$(CH_3)_2$—4-$NO_2$— | n-$C_3H_7$— | F | Cl | mp. 76.5–78 |
| 41 | 3,5-$(CH_3)_2$—4-$NO_2$— | i-$C_3H_7$— | F | Cl | mp. 77–79 |
| 42 | 3,5-$(CH_3)_2$—4-$NO_2$— | n-$C_4H_9$— | F | Cl | $n_D^{23}$ 1.5633 |
| 43 | 3,5-$(CH_3)_2$—4-$NO_2$— | i-$C_4H_9$— | F | Cl | $n_D^{23}$ 1.5587 |
| 44 | 3,5-$(CH_3)_2$—4-$NO_2$— | n-$C_5H_{11}$— | F | Cl | mp. 70.5–72 |
| 45 | 3,5-$(CH_3)_2$—4-$NO_2$— | $CH=CHCH_2$— | F | Cl | mp. 98.5–100 |
| 46 | 3,5-$(CH_3)_2$—4-$NO_2$— | $CH_2=C(CH_3)-CH_2$— | F | Cl | $n_D^{23}$ 1.5734 |
| 47 | 3,5-$(CH_3)_2$—4-$NO_2$— | $HC\equiv CCH_2$— | F | Cl | mp. 125–126.5 |
| 48 | 3,5-$(CH_3)_2$—4-$NO_2$— | $HC\equiv C-CH(CH_3)-$ | F | Cl | $n_D^{23}$ 1.5675 |
| 49 | 3,5-$(CH_3)_2$—4-$NO_2$— | $CH_3OCH_2CH_2$— | F | Cl | mp. 108.5–110 |
| 50 | 3,5-$(CH_3)_2$—4-$NO_2$— | $CH_3OCOCH_2$— | F | Cl | mp. 109–110.5 |
| 51 | 3,5-$(CH_3)_2$—4-$NO_2$— | $NC-CH_2$— | F | Cl | mp. 131–132 |
| 52 | 3,5-$(CH_3)_2$—4-$NO_2$— | $CH_3SO_2$— | F | Cl | mp. 150.5–152.5 |
| 53 | 3,5-$(CH_3)_2$—4-$NO_2$— | $C_6H_5SO_2$— | F | Cl | mp. 136–137.5 |
| 54 | 3,5-$(CH_3)_2$—4-$NO_2$— | H— | Cl | Cl | mp. 177.5–179.5 |
| 55 | 3,5-$(CH_3)_2$—4-$NO_2$— | $CH_3$— | Cl | Cl | mp. 148.5–150 |
| 56 | 3,5-$(CH_3)_2$—4-$NO_2$— | i-$C_3H_7$— | Cl | Cl | $n_D^{23}$ 1.5743 |
| 57 | 3,5-$(CH_3)_2$—4-$NO_2$— | $HC\equiv CCH_2$— | Cl | Cl | mp. 144.5–147 |
| 58 | 3,5-$(CH_3)_2$—4-$NO_2$— | $CH_3SO_2$— | Cl | Cl | mp. 161–162.5 |
| 59 | 3,5-$(CH_3)_2$—4-$NO_2$— | 4-Cl-$C_6H_4SO_2$— | Cl | Cl | mp. 166.5–168 |
| 60 | 3,5-$(CH_3)_2$—4-$NO_2$— | i-$C_3H_7$— | Br | F | $n_D^{23}$ 1.5323 |
| 61 | 3,5-$(CH_3)_2$—4-$NO_2$— | i-$C_3H_7$— | Br | Br | $n_D^{23}$ 1.5163 |
| 62 | 3-$CH_3$—4-$NO_2$—5-$C_2H_5$— | i-$C_3H_7$— | Cl | Cl | $n_D^{23}$ 1.5215 |
| 63 | 3-$C_2H_5$—4-$NO_2$—5-$CH_3$— | i-$C_3H_7$— | Cl | Cl | $n_D^{23}$ 1.5286 |
| 64 | 3,5-$(C_2H_5)_2$—4-$NO_2$— | i-$C_3H_7$— | F | Cl | $n_D^{23}$ 1.5244 |
| 65 | 3,5-$(C_2H_5)_2$—4-$NO_2$— | $HC\equiv CCH_2$— | F | Cl | $n_D^{23}$ 1.5362 |
| 66 | 3,5-$(C_2H_5)_2$—4-$NO_2$— | i-$C_3H_7$— | Cl | F | $n_D^{23}$ 1.5541 |
| 67 | 3,5-$(C_2H_5)_2$—4-$NO_2$— | i-$C_3H_7$— | Cl | Cl | $n_D^{23}$ 1.5408 |
| 68 | 3,5-$(C_2H_5)_2$—4-$NO_2$— | i-$C_3H_7$— | Br | Cl | $n_D^{23}$ 1.5326 |
| 69 | 3,5-$(CH_3)_2$—4-$NH_2$— | i-$C_3H_7$— | F | Cl | mp. 94–96.5 |
| 70 | 3,5-$(CH_3)_2$—4-$NH_2$— | $HC\equiv CCH_2$— | F | Cl | mp. 124–126 |
| 71 | 3,5-$(C_2H_5)_2$—4-$NH_2$— | i-$C_3H_7$— | F | Cl | $n_D^{23}$ 1.5554 |
| 72 | 3,5-$(CH_3)_2$—4-$CH_3CONH$— | i-$C_3H_7$— | F | Cl | mp. 140–141.5 |
| 73 | 3,5-$(CH_3)_2$—4-$CH_3OCONH$— | $HC\equiv CCH_2$— | F | Cl | mp. 189.5–191 |
| 74 | 3,5-$(CH_3)_2$—4-$CH_3NHCONH$— | i-$C_3H_7$— | F | Cl | mp. 184–185 |
| 75 | 3,5-$(CH_3)_2$—4-$(CH_3)_2NCONH$— | i-$C_3H_7$— | F | Cl | mp. 132.5–134.5 |
| 76 | 3,5-$(C_2H_5)_2$—4-$(CH_3)_2NCONH$— | i-$C_3H_7$— | F | Cl | $n_D^{23}$ 1.5262 |
| 77 | 3-$CF_3$—4-$CH_2=CHCH_2$—5-$CH_3$— | i-$C_3H_7$— | F | Cl | $n_D^{23}$ 1.5315 |
| 78 | 3-$CF_3$—4-$HC\equiv CCH_2$—5-$CH_3$— | i-$C_3H_7$— | F | Cl | $n_D^{23}$ 1.5385 |
| 79 | 3-$CH_3$—4-Cl—5-$CF_3$— | $HC\equiv CCH_2$— | F | Cl | mp. 105–108 |
| 80 | 3-$CF_3$—4-Cl—5-$CH_3$— | $HC\equiv CCH_2$— | F | Cl | mp. 85–87 |
| 81 | 3-$CF_3$—4-Cl—5-$CH_3$— | $CH_3SO_2$— | F | Cl | mp. 72–74.5 |
| 82 | 3-$CF_3$—4-$CH_3$—5-Cl— | i-$C_3H_7$— | F | Cl | $n_D^{23}$ 1.5069 |
| 83 | 3-$CF_3$—4-Br—5-$CH_3$— | i-$C_3H_7$— | F | Cl | $n_D^{23}$ 1.5232 |
| 84 | 3-$CF_3$—4-Br—5-$CH_3$— | n-$C_3H_7S-CH_2CH_2$— | F | Cl | $n_D^{23}$ 1.5185 |
| 85 | 3-$CF_3$—4-Br—5-$CH_3$— | $CH_3SO_2$— | F | Cl | mp. 139–142 |
| 86 | 3-$CF_3$—4,5-$Cl_2$— | i-$C_3H_7$— | F | Cl | $n_D^{23}$ 1.5105 |
| 87 | 3-$CF_3$—4-$NO_2$—5-$CH_3$— | i-$C_3H_7$— | F | Cl | $n_D^{23}$ 1.5226 |
| 88 | 3-$CF_3$—4-$C_2H_5NHCONH$—5-$CH_3$— | i-$C_3H_7$— | F | Cl | $n_D^{23}$ 1.5245 |

TABLE 1-continued

Structure: R_2O on phenyl ring (with Y, X substituents) attached via N1—N2 to a diene system with R_{1a} at position 3, R_{1b} at position 4, R_{1c} at position 5.

| Compound No. | $R_{1a}$, $R_{1b}$, $R_{1c}$ | $R_2$ | X | Y | Melting point (°C.) or refractive index ($n_D^{23}$) |
|---|---|---|---|---|---|
| 89 | 3,5-(CF$_3$)$_2$—4-CH$_3$— | i-C$_3$H$_7$— | F | Cl | $n_D^{23}$ 1.5166 |
| 90 | 3,5-(CF$_3$)$_2$—4-CH$_3$— | CH$_3$S—CH$_2$CH$_2$— | F | Cl | $n_D^{23}$ 1.5402 |
| 91 | 3,5-(CF$_3$)$_2$—4-CH$_2$=CHCH$_2$— | i-C$_3$H$_7$— | F | Cl | $n_D^{23}$ 1.5351 |
| 92 | 3,5-(CF$_3$)$_2$—4-CH$_2$=CHCH$_2$— | C$_2$H$_5$S—COCH$_2$— | F | Cl | $n_D^{23}$ 1.5229 |
| 93 | 3,5-(CF$_3$)$_2$—4-NO$_2$— | i-C$_3$H$_7$— | F | Br | $n_D^{23}$ 1.5145 |
| 94 | 3,5-(CF$_3$)$_2$—4-NH$_2$— | i-C$_3$H$_7$— | F | Br | $n_D^{23}$ 1.5231 |
| 95 | 3,5-(NO$_2$)$_2$—4-CH$_3$CONH— | i-C$_3$H$_7$— | F | Cl | $n_D^{23}$ 1.5348 |
| 96 | H— | i-C$_3$H$_7$— | F | Cl | $n_D^{23}$ 1.5421 |
| 97 | H— | i-C$_3$H$_7$— | F | Br | $n_D^{23}$ 1.5425 |
| 98 | H— | i-C$_3$H$_7$— | Cl | Cl | $n_D^{23}$ 1.5491 |
| 99 | 3-CH$_3$— | i-C$_4$H$_9$— | Cl | Cl | $n_D^{23}$ 1.5473 |
| 100 | 4-CH$_3$— | n-C$_3$H$_7$— | Cl | Cl | $n_D^{23}$ 1.5402 |
| 101 | 5-CH$_3$— | i-C$_3$H$_7$— | F | Cl | $n_D^{23}$ 1.5474 |
| 102 | 5-CH$_3$— | CH$_2$=C(CH$_3$)—CH$_2$— | F | Cl | $n_D^{23}$ 1.5413 |
| 103 | 5-C$_2$H$_5$— | C$_2$H$_5$— | F | Br | $n_D^{23}$ 1.5502 |
| 104 | 4-CH$_2$=CH—CH$_2$— | i-C$_3$H$_7$— | Cl | Cl | $n_D^{23}$ 1.5469 |
| 105 | 4-Cl— | i-C$_3$H$_7$— | F | Cl | $n_D^{23}$ 1.5534 |
| 106 | 5-Cl— | i-C$_3$H$_7$— | F | Cl | $n_D^{23}$ 1.5489 |
| 107 | 5-Cl— | i-C$_3$H$_7$— | Cl | Cl | $n_D^{23}$ 1.5510 |
| 108 | 5-Br— | i-C$_3$H$_7$— | F | Cl | $n_D^{23}$ 1.5488 |
| 109 | 3,5-(CH$_3$)$_2$— | H— | Cl | Cl | mp. 78.5–80 |
| 110 | 3,5-(CH$_3$)$_2$— | i-C$_3$H$_7$— | F | Cl | $n_D^{23}$ 1.5439 |
| 111 | 3,5-(CH$_3$)$_2$— | i-C$_3$H$_7$— | Cl | Cl | mp. 77.5–79 |
| 112 | 3,5-(CH$_3$)$_2$— | CH$_3$SO$_2$— | F | Cl | mp. 77.5–79 |
| 113 | 3,5-(C$_2$H$_5$)$_2$— | CH$_3$S—CH$_2$CH$_2$— | F | Br | $n_D^{23}$ 1.5436 |
| 114 | 3,5-(C$_2$H$_5$)$_2$— | CH$_3$SO$_2$— | F | Cl | $n_D^{23}$ 1.5312 |
| 115 | 4-C$_2$H$_5$—5-CH$_3$— | i-C$_3$H$_7$— | Cl | Cl | $n_D^{23}$ 1.5376 |
| 116 | 4-C$_2$H$_5$—5-CH$_3$— | NC—CH(CH$_3$)— | Cl | Cl | $n_D^{23}$ 1.5404 |
| 117 | 4-CH$_2$=CHCH$_2$—5-CH$_3$— | i-C$_3$H$_7$— | Cl | Cl | $n_D^{23}$ 1.5412 |
| 118 | 4-Cl—5-CH$_3$— | i-C$_3$H$_7$— | F | Cl | $n_D^{23}$ 1.5399 |
| 119 | 4-Cl—5-CH$_3$— | i-C$_3$H$_7$— | Cl | Cl | $n_D^{23}$ 1.5413 |
| 120 | 4,5-Cl$_2$— | i-C$_3$H$_7$— | F | Cl | $n_D^{23}$ 1.5420 |
| 121 | 4,5-Cl$_2$— | i-C$_3$H$_7$— | Cl | Cl | $n_D^{23}$ 1.5498 |
| 122 | 3,4,5-(CH$_3$)$_3$— | H— | F | Cl | mp. 158–160 |
| 123 | 3,4,5-(CH$_3$)$_3$— | H— | Cl | F | mp. 172–173.5 |
| 124 | 3,4,5-(CH$_3$)$_3$— | CH$_3$— | F | Cl | mp. 151–153 |
| 125 | 3,4,5-(CH$_3$)$_3$— | CH$_3$— | Cl | F | mp. 122.5–124 |
| 126 | 3,4,5-(CH$_3$)$_3$— | C$_2$H$_5$— | F | Cl | mp. 112–114.5 |
| 127 | 3,4,5-(CH$_3$)$_3$— | C$_2$H$_5$— | F | Br | $n_D^{23}$ 1.5436 |
| 128 | 3,4,5-(CH$_3$)$_3$— | n-C$_3$H$_7$— | F | Cl | mp. 54.5–57 |
| 129 | 3,4,5-(CH$_3$)$_3$— | i-C$_3$H$_7$— | F | Cl | $n_D^{23}$ 1.5406 |
| 130 | 3,4,5-(CH$_3$)$_3$— | i-C$_3$H$_7$— | F | Br | $n_D^{23}$ 1.5418 |
| 131 | 3,4,5-(CH$_3$)$_3$— | i-C$_3$H$_7$— | Cl | F | mp. 52–54.5 |
| 132 | 3,4,5-(CH$_3$)$_3$— | i-C$_3$H$_7$— | Cl | Cl | mp. 56–58 |
| 133 | 3,4,5-(CH$_3$)$_3$— | n-C$_4$H$_9$— | F | Cl | $n_D^{23}$ 1.5459 |
| 134 | 3,4,5-(CH$_3$)$_3$— | i-C$_4$H$_9$— | Br | F | $n_D^{23}$ 1.5468 |
| 135 | 3,4,5-(CH$_3$)$_3$— | sec-C$_4$H$_9$— | Cl | Cl | $n_D^{23}$ 1.5466 |
| 136 | 3,4,5-(CH$_3$)$_3$— | CH$_2$=CHCH$_2$— | F | Cl | mp. 97–99 |
| 137 | 3,4,5-(CH$_3$)$_3$— | CH$_2$=C(CH$_3$)—CH$_2$ | F | Cl | mp. 98–99.5 |
| 138 | 3,4,5-(CH$_3$)$_3$— | HC≡CCH$_2$— | F | Cl | mp. 140.5–142 |
| 139 | 3,4,5-(CH$_3$)$_3$— | HC≡CCH$_2$— | Cl | F | mp. 133.5–135.5 |
| 140 | 3,4,5-(CH$_3$)$_3$— | HC≡CCH$_2$— | Cl | Cl | mp. 156.5–158 |
| 141 | 3,4,5-(CH$_3$)$_3$— | HC≡C—CH(CH$_3$)— | F | Cl | mp. 67–68.5 |

TABLE 1-continued

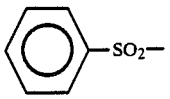

| Compound No. | $R_{1a}, R_{1b}, R_{1c}$ | $R_2$ | X | Y | Melting point (°C.) or refractive index ($n_D^{23}$) |
|---|---|---|---|---|---|
| 142 | 3,4,5-$(CH_3)_3$— | $HC{\equiv}C{-}CH(CH_3){-}$ | Cl | F | mp. 89–90.5 |
| 143 | 3,4,5-$(CH_3)_3$— | $HC{\equiv}C{-}CH(CH_3){-}$ | Cl | Cl | mp. 71–73 |
| 144 | 3,4,5-$(CH_3)_3$— | n-$C_4H_9OCH_2CH_2$— | Cl | F | $n_D^{23}$ 1.5479 |
| 145 | 3,4,5-$(CH_3)_3$— | $CH_3COCH_2$— | Cl | F | $n_D^{23}$ 1.5483 |
| 146 | 3,4,5-$(CH_3)_3$— | $CH_3OCOCH_2$— | F | Cl | mp. 105–107 |
| 147 | 3,4,5-$(CH_3)_3$— | $NC{-}CH_2$— | F | Cl | mp. 147–149 |
| 148 | 3,4,5-$(CH_3)_3$— | $CH_3SO_2$— | F | Cl | mp. 123–125 |
| 149 | 3,4,5-$(CH_3)_3$— | $CH_3SO_2$— | Cl | F | mp. 95–96.5 |
| 150 | 3,4,5-$(CH_3)_3$— | $C_6H_5SO_2$— | F | Cl | $n_D^{23}$ 1.5492 |
| 151 | 3,5-$(CH_3)_2$—4-$C_2H_5$— | $CH_3$— | F | Cl | $n_D^{23}$ 1.5483 |
| 152 | 3,5-$(CH_3)_2$—4-$C_2H_5$— | i-$C_3H_7$— | F | Cl | $n_D^{23}$ 1.5328 |
| 153 | 3,5-$(CH_3)_2$—4-$C_2H_5$— | i-$C_3H_7$— | Cl | Cl | mp. 56–58 |
| 154 | 3,5-$(CH_3)_2$—4-$C_2H_5$— | $CH_2{=}CH{-}CH(CH_3){-}$ | F | Cl | $n_D^{23}$ 1.5395 |
| 155 | 3,5-$(CH_3)_2$—4-$C_2H_5$— | $CH_3CH{=}CHCH_2$— | Cl | Cl | $n_D^{23}$ 1.5377 |
| 156 | 3,5-$(CH_3)_2$—4-n-$C_3H_7$— | i-$C_3H_7$— | F | Cl | $n_D^{23}$ 1.5212 |
| 157 | 3,5-$(CH_3)_2$—4-n-$C_3H_7$— | i-$C_3H_7$— | Cl | Cl | $n_D^{23}$ 1.5452 |
| 158 | 3,5-$(CH_3)_2$—4-i-$C_3H_7$— | i-$C_3H_7$— | F | Cl | $n_D^{23}$ 1.5312 |
| 159 | 3,5-$(CH_3)_2$—4-i-$C_3H_7$— | i-$C_3H_7$— | Cl | Cl | $n_D^{23}$ 1.5584 |
| 160 | 3,5-$(CH_3)_2$—4-$CH_2{=}CHCH_2$— | i-$C_3H_7$— | F | Cl | $n_D^{23}$ 1.5428 |
| 161 | 3,5-$(CH_3)_2$—4-$CH_2{=}CHCH_2$— | i-$C_3H_7$— | Cl | Cl | $n_D^{23}$ 1.5433 |
| 162 | 3,5-$(C_2H_5)_2$—4-$CH_3$— | n-$C_3H_7$— | F | Cl | $n_D^{23}$ 1.5448 |
| 163 | 3,5-$(C_2H_5)_2$—4-$CH_3$— | i-$C_3H_7$— | F | Cl | mp. 30–31 |
| 164 | 3,5-$(C_2H_5)_2$—4-$CH_3$— | i-$C_4H_9$— | Cl | Cl | $n_D^{23}$ 1.5407 |
| 165 | 3,4,5-$(C_2H_5)_3$— | H— | F | Cl | mp. 129–131.5 |
| 166 | 3,4,5-$(C_2H_5)_3$— | i-$C_3H_7$— | F | Cl | $n_D^{23}$ 1.5384 |
| 167 | 3,4,5-$(C_2H_5)_3$— | $HC{\equiv}CCH_2$— | F | Cl | mp. 62–65 |
| 168 | 3,4,5-$(C_2H_5)_3$— | $CH_3SO_2$— | F | Cl | $n_D^{23}$ 1.5359 |
| 169 | 3,5-$(C_2H_5)_2$—4-$HC{\equiv}CCH_2$— | i-$C_3H_7$— | F | Cl | $n_D^{23}$ 1.5391 |
| 170 | 3,5-$(C_2H_5)_2$—4-$HC{\equiv}CCH_2$— | i-$C_3H_7$— | Cl | Cl | $n_D^{23}$ 1.5402 |
| 171 | 3,5-$(CH_3)_2$—4-Cl— | H— | F | Cl | mp. 159–161 |
| 172 | 3,5-$(CH_3)_2$—4-Cl— | H— | Cl | F | mp. 159–161 |
| 173 | 3,5-$(CH_3)_2$—4-Cl— | H— | Cl | Cl | mp. 172–174 |
| 174 | 3,5-$(CH_3)_2$—4-Cl— | $CH_3$— | Cl | Cl | mp. 132–135 |
| 175 | 3,5-$(CH_3)_2$—4-Cl— | $C_2H_5$— | Cl | Cl | mp. 106–107.5 |
| 176 | 3,5-$(CH_3)_2$—4-Cl— | i-$C_3H_7$— | F | Cl | $n_D^{23}$ 1.5514 |
| 177 | 3,5-$(CH_3)_2$—4-Cl— | i-$C_3H_7$— | Cl | F | mp. 56–57 |
| 178 | 3,5-$(CH_3)_2$—4-Cl— | i-$C_3H_7$— | Cl | Cl | mp. 56.5–57.5 |
| 179 | 3,5-$(CH_3)_2$—4-Cl— | i-$C_3H_7$— | Br | Cl | $n_D^{23}$ 1.5448 |
| 180 | 3,5-$(CH_3)_2$—4-Cl— | i-$C_3H_7$— | Br | Br | $n_D^{23}$ 1.5503 |
| 181 | 3,5-$(CH_3)_2$—4-Cl— | n-$C_4H_9$— | F | Cl | $n_D^{23}$ 1.5413 |
| 182 | 3,5-$(CH_3)_2$—4-Cl— | $CH_2{=}CHCH_2$— | Cl | Cl | mp. 115–116.5 |
| 183 | 3,5-$(CH_3)_2$—4-Cl— | $HC{\equiv}CCH_2$— | F | Cl | mp. 143.5–144.5 |
| 184 | 3,5-$(CH_3)_2$—4-Cl— | $HC{\equiv}CCH_2$— | Cl | F | mp. 121.5–123 |
| 185 | 3,5-$(CH_3)_2$—4-Cl— | $HC{\equiv}CCH_2$— | Cl | Cl | mp. 154–155 |
| 186 | 3,5-$(CH_3)_2$—4-Cl— | i-$C_3H_7S{-}CH_2CH_2$— | F | Cl | $n_D^{23}$ 1.5398 |
| 187 | 3,5-$(CH_3)_2$—4-Cl— | $C_2H_5OCOCH_2$— | F | Cl | mp. 101–104 |
| 188 | 3,5-$(CH_3)_2$—4-Cl— | $C_2H_5S{-}COCH_2$— | F | Cl | $n_D^{23}$ 1.5446 |
| 189 | 3,5-$(CH_3)_2$—4-Cl— | $CH_3SO_2$— | F | Cl | $n_D^{23}$ 1.5431 |
| 190 | 3,5-$(CH_3)_2$—4-Cl— | $CH_3SO_2$— | Cl | F | mp. 94.5–96 |
| 191 | 3,5-$(CH_3)_2$—4-Cl— | $CH_3SO_2$— | Cl | Cl | mp. 109–111 |
| 192 | 3,5-$(CH_3)_2$—4-Cl— | n-$C_3H_7SO_2$— | F | Cl | $n_D^{23}$ 1.5453 |

TABLE 1-continued

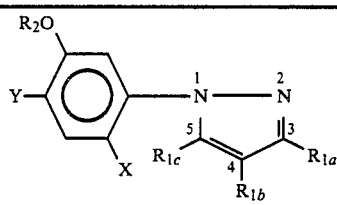

| Compound No. | $R_{1a}$, $R_{1b}$, $R_{1c}$ | $R_2$ | X | Y | Melting point (°C.) or refractive index ($n_D^{23}$) |
|---|---|---|---|---|---|
| 193 | 3,5-$(CH_3)_2$—4-Cl— | $CH_3$—⟨○⟩—$SO_2$— | F | Cl | $n_D^{23}$ 1.5475 |
| 194 | 3,5-$(C_2H_5)_2$—4-Cl— | H— | F | Cl | $n_D^{23}$ 1.5611 |
| 195 | 3,5-$(C_2H_5)_2$—4-Cl— | i-$C_3H_7$— | F | Cl | $n_D^{23}$ 1.5390 |
| 196 | 3,5-$(C_2H_5)_2$—4-Cl— | i-$C_3H_7$— | Cl | Cl | $n_D^{23}$ 1.5427 |
| 197 | 3,5-$(C_2H_5)_2$—4-Cl— | HC≡$CCH_2$— | F | Cl | mp. 92–94.5 |
| 198 | 3,5-$(C_2H_5)_2$—4-Cl— | $C_2H_5OCOCH_2$— | F | Cl | mp. 109–110.5 |
| 199 | 3,5-$(C_2H_5)_2$—4-Cl— | $CH_3SO_2$— | F | Cl | $n_D^{23}$ 1.5496 |
| 200 | 3,5-$(C_2H_5)_2$—4-Cl— | Cl—⟨○⟩—$SO_2$— | F | Cl | $n_D^{23}$ 1.5482 |
| 201 | 3,5-$(CH_3)_2$—4-Br— | H— | F | Cl | mp. 167–169 |
| 202 | 3,5-$(CH_3)_2$—4-Br— | H— | Cl | F | mp. 176–177 |
| 203 | 3,5-$(CH_3)_2$—4-Br— | i-$C_3H_7$— | F | Cl | $n_D^{23}$ 1.5610 |
| 204 | 3,5-$(CH_3)_2$—4-Br— | i-$C_3H_7$— | Cl | F | mp. 55–56 |
| 205 | 3,5-$(CH_3)_2$—4-Br— | HC≡$CCH_2$— | F | Cl | mp. 157–158 |
| 206 | 3,5-$(CH_3)_2$—4-Br— | HC≡$CCH_2$— | Cl | F | mp. 135–136 |
| 207 | 3,5-$(CH_3)_2$—4-Br— | $C_2H_5OCOCH_2$— | F | Cl | mp. 119–120.5 |
| 208 | 3,5-$(CH_3)_2$—4-Br— | $CH_3SO_2$— | F | Cl | $n_D^{23}$ 1.5472 |
| 209 | 3,5-$(CH_3)_2$—4-Br— | $CH_3SO_2$— | Cl | F | mp. 111–114 |

In Table 1 above, when any of $R_{1a}$, $R_{1b}$ and $R_{1c}$ is or are hydrogen atom(s), this is not indicated in the table specifically, except for compound Nos. 96, 97 and 98.

Compound Numbers shown in Table 1 are referred to hereinafter to identify the compounds as used or as produced in the following descriptions.

Amongst the particular compounds listed in Table 1 above, the following are preferred compounds in this invention.

(1) 1-(2-fluoro-4-chloro-5-allyloxyphenyl)-3,5-dimethyl-4-nitropyrazole (Compound No. 45)

(2) 1-(2-fluoro-4-chloro-5-propargyloxyphenyl)-3,5-dimethyl-4-nitropyrazole (Compound No. 47)

(3) 1-[2-fluoro-4-chloro-5-(1-methyl-2-propynyl)oxyphenyl]-3,5-dimethyl-4-nitropyrazole (Compound No. 48)

(4) 1-(2-fluoro-4-chloro-5-propargyloxyphenyl)-3,4,5-trimethylpyrazole (Compound No. 138)

(5) 1-(2-fluoro-4-chloro-5-propargyloxyphenyl)-3,5-dimethyl-4-chloropyrazole (Compound No. 183)

(6) 1-(2-fluoro-4-chloro-5-propargyloxyphenyl)-3,5-dimethyl-4-bromopyrazole (Compound No. 205)

The new compounds of the formula (I) according to the first aspect of this invention show improved herebicidal activity over the known pyrazole derivatives as disclosed in the aforesaid Japanese patent publications No. 19958/65 and No. 14833/67. Thus, the new compounds of this invention are herbicidally active against a wide variety of unwanted weeds, such as barnyard grass (*Echinochloa crus-galli*), monochoria (*Monochoria vaginalis*), narrowleaf water-plantain (*Alisma canaliculatum*), bulrush (*Scirpus juncoides*), false pimpernel (*Lindernia procumbens*), and tooth cup (*Rotala indica*) which frequently grow in the irrigated fields of aquatic rice plant. These sorts of weeds grown in the irrigated fields of rice plant can be killed completely by applying the new compound at a rate of application of 50 g or less of the compound of this invention per 10 ares of the field. When some preferred particular compounds are employed amongst the new compounds of this invention, the above-mentioned sorts of weeds can be killed completely even by application of the preferred compound at a rate of 6.25 g or less per 10 ares. The new compounds of this invention are also herbicidally active against a wide variety of unwanted weeds, such as crabgrass (*Digitaria adscendens*), common lambsquarters (*Chenopodium album*), pigweed (*Amaranthus ascendens*) and smartweed (*Polygonum nodosum*) which frequently grow in the farm fields (non-irrigated) for various crop plants. These sorts of weeds grown in the non-irrigated farm fields can be killed completely by applying the compound of this invention at a rate of application of 50 g or less of the compound of this invention per 10 ares. Application of some preferred particular compounds amongst the compounds of this invention can achieve complete kill of the weeds grown in the non-irrigated farm fields even at a rate of application of 12.5 g or less of the preferred compound. Further, the new compounds of this invention advantageously show no significant phytotoxicity to crop plants such as rice plant, soy bean, sugar beet, radish, wheat, barley and maize. Besides, it is observed that the new compounds of this invention are neither toxic to mammalian animals nor toxic to fishes, so that the compounds of this invention can be applied to the weeds with safety to the crop-plants as well as the animals.

The new compounds of the general formula (I) according to the first aspect of this invention include the following four particular embodiments:

(1) According to the first embodiment, there is provided a compound of the formula

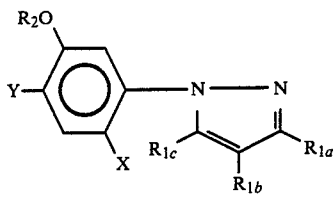

(Ia)

where $R_{1a}$, $R_{1b}$ and $R_{1c}$ each are a hydrogen atom, a halogen atom, a (lower)alkyl group, a (lower)alkenyl group or a (lower)alkynyl group, $R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower) alkoxycarbonyl(lower)alkyl group, a (lower)alkylthiocarbonyl(lower)alkyl group, a cyano(lower)alkyl group, X and Y are the same or different and each are a halogen atom.

(2) According to the second embodiment, there is provided a compound of the formula

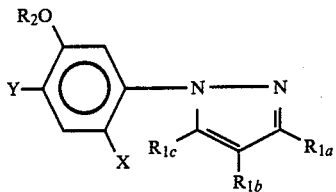

(Ib)

where $R_{1a}$, $R_{1b}$ and $R_{1c}$ each are a hydrogen atom, a halogen atom, a (lower)alkyl group, a (lower)alkenyl group or a (lower)alkynyl group, $R_2$ is a (lower)alkylsulfonyl group, phenylsulfonyl group, a halogen-substituted phenylsulfonyl group or a (lower)alkyl-substituted phenylsulfonyl group, and X and Y are the same or different and each are a halogen atom.

(3) According to the third embodiment, there is provided a compound of the formula

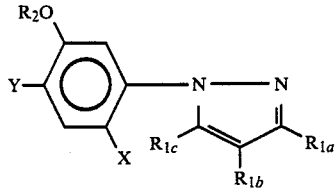

(Ic)

wherein
$R_{1a}$, $R_{1b}$ and $R_{1c}$ are each a hydrogen atom, a halogen atom, a nitro group, an amino group, a (lower) alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group; provided that at least one of $R_{1a}$, $R_{1b}$ and $R_{1c}$ is or are a halo-(lower)alkyl group, a nitro group, an amino group, a (lower)alkylcarbonylamino group, a (lower)alkoxycarbonylamino group, a mono-(lower)alkylaminocarbonylamino group or a di-(lower)alkylaminocarbonylamino group, $R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower alkoxycarbonyl(lower)alkyl group, a (lower)alkylthiocarbonyl(lower)alkyl group, a cyano(lower)alkyl group, and X and Y are the same or different and each are a halogen atom.

(4) According to the fourth embodiment, there is provided a compound of the formula

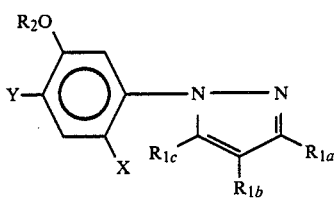

(Id)

wherein
$R_{1a}$, $R_{1b}$ and $R_{1c}$ are each a hydrogen atom, a halogen atom, a nitro group, an amino group, a (lower) alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group; provided that at least one of $R_{1a}$, $R_{1b}$ and $R_{1c}$ is or are a halo-(lower)alkyl group, a nitro group, an amino group, a (lower)alkylcarbonylamino group, a (lower)alkoxycarbonylamino group, a mono(lower)alkylaminocarbonylamino group or a di-(lower)alkylaminocarbonylamino group, $R_2$ is a (lower)alkylsulfonyl group, phenylsulfonyl group, a halogen-substituted phenylsulfonyl group or a (lower)alkyl-substituted phenylsulfonyl group, and X and Y are the same or different and each are a halogen atom.

The compound of the formula (Ia) as above according to the above-mentioned first embodiment includes, as preferred modes, the following three types:

(i) A compound of the formula

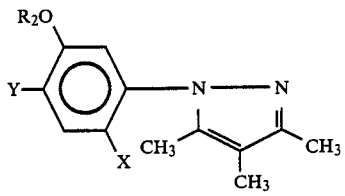

(Ie)

where $R_2$ is a (lower)alkyl group, a (lower)alkenyl group or a (lower)alkynyl group; and X and Y are the same or different and each are chlorine, bromine, fluorine or iodine atom.

(ii) A compound of the formula

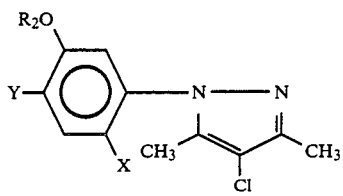

(If)

where $R_2$ is a (lower)alkyl group, a (lower)alkenyl group or a (lower)alkynyl group; and X and Y are the same or different and each are chlorine, bromine, fluorine or iodine atom.

(iii) A compound of the formula

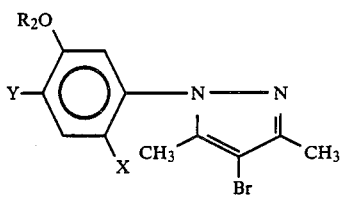

(Ig)

where $R_2$ is a (lower)alkyl group, a (lower)alkenyl group or a (lower)alkynyl group; and X and Y are the same or different and each are chlorine, bromine, fluorine or iodine atom.

The compound of the formula (Ic) as above according to the above-mentioned third embodiment includes as a preferred mode, the following type:

(iv) A compound of the formula

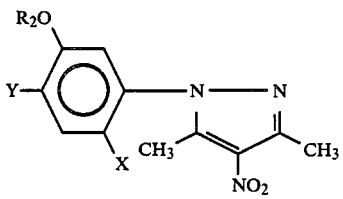

(Ih)

where $R_2$ is a (lower)alkyl group, a (lower)alkenyl group or a (lower)alkynyl group; and X and Y are the same or different and each are chlorine, bromine, fluorine or iodine atom.

The compounds of the general formula (I) according to the first aspect of this invention may be prepared by a variety of processes, typically by seven processes (A) to (G) as described below. Any of these processes (A) to (G) may be chosen appropriately, depending upon the nature of the substituents $R_{1a}$, $R_{1b}$, $R_{1c}$ and $R_2$ existing in the compounds of the formula (I) to be produced.

The various processes (A) to (G) of producing different types of the compounds of the formula (I) will be described below, schematically with reference to the reaction equations involved, where the substituents $R_{1a}$, $R_{1b}$ and $R_{1c}$ are referred to merely as $-(R_1)_n$, for sake of simplicity of expression, and where the substituent $R_2$ is also simply shown as $R_2$, though the substituents $R_1$ and $R_2$ of the concerned compound as shown in the reaction equations may have meanings which are, exactly speaking, not the very same meanings as defined for them with reference to the aforesaid general formula (I).

Process (A):

This process may be applied to the preparation of compounds (I-A), i.e. those of the general formula (I) where $R_{1a}$, $R_{1b}$ and $R_{1c}$ represent each a hydrogen, a lower alkyl, a haloalkyl, a lower alkyl, a lower alkenyl or a lower alkynyl, and $R_2$ represents a group defined above, except hydrogen, and this process (A) comprises such a reaction between a substituted phenylhydrazine compound of formula (II-A) and a di-carbonyl compound of formula (III) such as acetylacetone, malonalde, 1,1,1,5,5,5,-hexafluoro-penta-2,4-dione, 3-trifluoromethyl-penta-2,4-dione, 3-methylpenta-2,4-dione and 4-ethylhepta-3,5-dione, with involving the condensation and cyclization to give a compound of formula (I-A). This may be represented by the chemical equation:

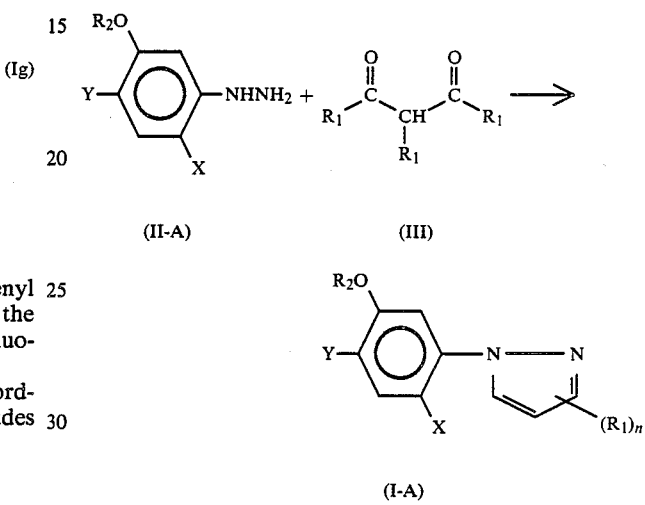

where n is 3 herein and hereinafter, unless otherwise stated.

The reaction may usually be conducted in various solvents including organic solvents such as hydrocarbons, ethers and alcohols and water. The reaction may proceed at room temperatures, but is preferably carried out at a higher temperature up to the refluxing temperature of the solvent used, under heating. After the completion of the reaction, the solvent may be removed from the reaction mixture by distillation to recover the desired reaction product. Alternatively, the desired product may be recovered by extracting the reaction mixture with water and an organic solvent such as benzene, toluene, tetrahydrofuran and chloroform and distilling off the solvent from the extract to obtain the desired product.

Process (A) is illustrated in Examples 1 to 5 hereinlater given.

Process (B):

This process is applicable to the preparation of compounds (I-B), i.e. those of general formula (I) where $R_{1a}$, $R_{1b}$ and $R_{1c}$ represent each a group defined above, except a (lower)alkylcarbonylamino, a (lower)alkoxycarbonylamino, a mono-(lower)alkylaminocarbonylamino and a di-(lower)alkylaminocarbonylamino, and $R_2$ is hydrogen, and this process (B) comprises hydrolyzing a compound of formula (I-C) which is itself within compounds of general formula (I) and which has as R such a group hydrolyzable to leave a hydroxyl group on the 5-position of the benzene ring. This reaction may be represented by the chemical equation:

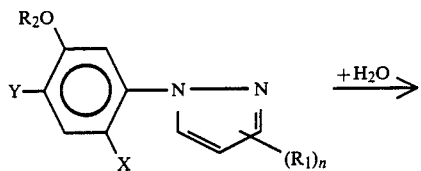

(I-C)

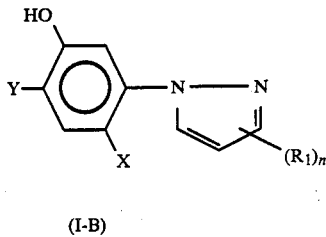

(I-B)

The hydrolysis may be effected simply by heating compound (I-C) together with water or in an aqueous organic solvent, but usually carried out in the presence of one equivalent or more of a basic compound. As the base, there may be used typically an alkali metal hydroxide such as sodium hydroxide, potassium hydroxide, or an alkali metal carbonate such as sodium carbonate and potassium carbonate. The reaction may proceed either at room temperatures or under heating. The addition of an alcohol such as methanol or an ether such as dioxane to the aqueous reaction medium for forming a homogeneous reaction phase may accelerate the reaction.

After the completion of the reaction, the reaction solution is made acidic with the addition of an inorganic acid such as hydrochloric acid and sulfuric acid and then extracted with an organic solvent such as benzene, toluene, tetrahydrofuran and chloroform. The removal of solvent from the extract by distillation yields the desired compound of formula (I-B).

Process (B) is illustrated hereinlater in Examples 6 to 8.

Process (C):

This process is applicable to the preparation of compounds (I-D) i.e. those of general formula (I) where $R_{1a}$, $R_{1b}$ and $R_{1c}$ have the same meaning as defined above and $R_2$ is a group defined above except hydrogen, and this process (C) comprises reacting a compound of formula (I-E) where $R_{1a}$, $R_{1b}$ and $R_{1c}$ correspond to those of the product compound (I-D) and $R_2$ is hydrogen, with a halide compound of formula (IV) such as an alkyl chloride, an alkenyl chloride and an alkylsulfonyl chloride. This reaction may be shown by the chemical equation:

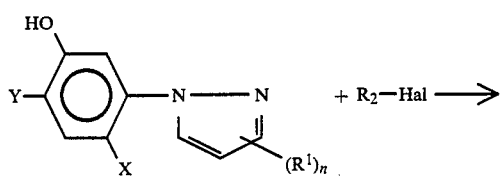

(I-E)            (IV)

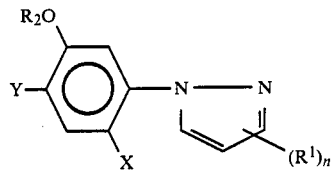

(I-D)

This substitution reaction may usually be conducted in an organic solvent in the presence of an acid binding agent. As such organic solvent, there may be used hydrocarbons such as benzene and toluene; ethers such as ethyl ether and tetrahydrofuran; esters such as methyl acetate and ethyl acetate; ketones such as acetone and methyl isobutyl ketone; nitriles such as acetonitrile and propionitrile amides such as dimethylformamide and dimethylacetamide; and dimethyl sulfoxide. The acid binding agent may be an inorganic base such as sodium hydroxide, sodium amide and potassium carbonate or an organic base such as triethylamine and pyridine. The reaction may be carried out at room temperatures or under heating to a temperature up to the refluxing temperature of the solvent used.

After the completion of the reaction, the reaction mixture may be filtered to remove the salt(s) of the acid binding agent as formed and then distilled to remove the solvent used, affording the desired compound (I-D) produced. Alternatively, the desired compound may be isolated by adding to the reaction mixture water and an organic solvent such as benzene, toluene, tetrahydrofuran and chloroform to extract the compound and distilling off the solvent from the extract to leave the compound.

Process (C) is illustrated in Examples 9 to 14.

Process (D):

This process is applicable to the preparation of compounds (I-F), i.e. those of general formula (I) where at least one of $R_{1a}$, $R_{1b}$ and $R_{1c}$ is a halogen atom, and this process (D) comprises reacting a halogenating agent having a halogen atom (Z) to be introduced, with a compound of formula (I-G) where $R_{1a}$, $R_{1b}$, $R_{1c}$ and $R_2$ correspond to those of the product compound (I-F) provided that at least one of $R_{1a}$, $R_{1b}$ and $R_{1c}$ is a hydrogen atom, and, for instance, all of $R_{1a}$, $R_{1b}$ and $R_{1c}$ are not halogen atoms, or one or two of $R_{1a}$, $R_{1b}$ and $R_{1c}$ are halogen atoms other than the halogen (Z) to be introduced, or one or two of $R_{1a}$, $R_{1b}$ and $R_{1c}$ are the same as the halogen atoms (Z) to be introduced. This reaction may be approximately depicted by the chemical equation:

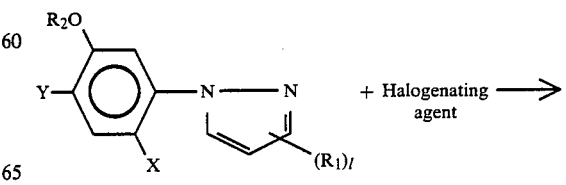

(I-G)

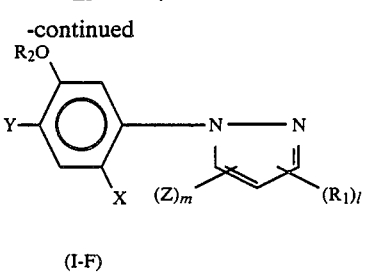

(I-F)

wherein $R_1$ is as explained above but except hydrogen, and $R_2$, X and Y are as defined above; l is 0, 1 or 2; Z is each a halogen atom introduced by the halogenating agent, m is 3, 2 or 1 and (l+m) is an integer of 1 to 3.

The halogenation reaction may conveniently be effected in an organic solvent such as halogenated hydrocarbons, amides and water. Halogenating agent which may be used includes an elementary halogen such as chlorine and bromine; sulfuryl halides and phosporus halides. The reaction temperature may be appropriately chosen from room temperature to the boiling point of the solvent used.

After the completion of the reaction, the desired product may be isolated in many cases by distilling off the solvent from the reaction mixture. If necessary, however, water and an organic solvent may be added to the reaction mixture to extract the desired compound and the solvent may be distilled off from the extract to afford the desired compound of formula (I-F).

Process (D) is illustrated by way of Examples 15 to 17.

Process (E)

This process is applicable to the preparation of compound (I-H), i.e. those of general formula (I) where at least one of $R_{1a}$, $R_{1b}$, $R_{1c}$ is nitro group, and this process (E) comprises reacting a nitrating agent with a compound of formula (I-I) where $R_{1a}$, $R_{1b}$, $R_{1c}$ and $R_2$ correspond to those of compound (I-H) provided that at least one of $R_{1a}$, $R_{1b}$ and $R_{1c}$ is the hydrogen atom, and for instance, all of $R_{1a}$, $R_{1b}$ and $R_{1c}$ are not nitro groups or one or two of $R_{1a}$, $R_{1b}$ and $R_{1c}$ are nitro groups already introduced. This reaction may be approximately depicted by the chemical equation:

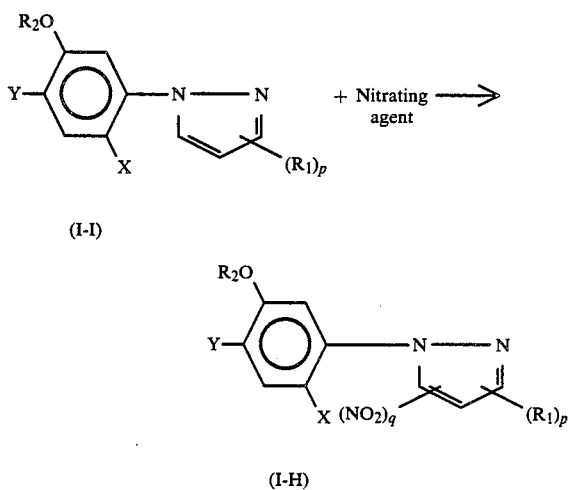

where $R_1$ is as explained above but except hydrogen, and $R_2$, X and Y are as defined above; p is 0,1 or 2; q is 3, 2 or 1 and (p+q) is an integer of 1 to 3.

The nitration reaction may usually be effected in a solvent, for example, an inorganic acid such as sulfuric acid; an organic acid such as acetic acid; water; or a mixture of an acid and water. As the nitrating agent, there may be used usually nitric acid and fuming nitric acid. The reaction temperature may be appropriately chosen from a temperature under cooling with ice-water to the refluxing temperature of the solvent used.

After the completion of the reaction, the desired compound may be recovered, for example, by adding water to the reaction mixture, extracting the desired compound with an organic solvent such as benzene toluene, tetrahydrofuran and chloroform and distilling off the organic solvent from the extract to leave the desired compound.

Process (E) is illustrated by way of Example 18.

Process (F):

This process is applicable to the preparation of compounds (I-J), i.e. those of general formula (I) where at least one of $R_{1a}$, $R_{1b}$ and $R_{1c}$ is amino group, and this process (F) comprises reducing a corresponding nitrosubstituted compound of formula (I-H). This reaction may be shown by the chemical equation:

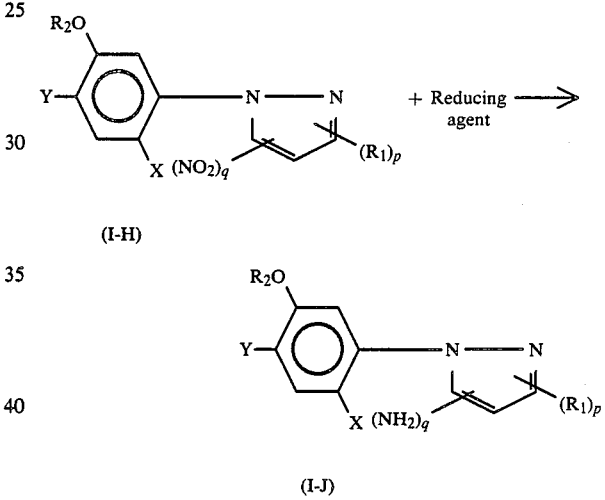

where $R_1$ is as explained above but except hydrogen and $R_2$, X, Y, p and q are as defined above.

The reduction may be effected, in general, using iron or tin or nascent hydrogen as reducing agent. Usually, water is used as solvent. In most cases, the addition of a small amount of hydrochloric acid to the water can promote the reaction intended. The reaction temperature may be appropriately chosen from a temperature under cooling with ice-water to the refluxing temperature of water. Warming up of the reaction mixture may promote the reaction, shortening the reaction time.

After the completion of the reaction, the desired compound may be recovered by extracting the reaction mixture with an organic solvent such as benzene, toluene, tetrahydrofuran and chloroform and distilling off the solvent from the extract to leave the desired compound.

Process (F) is illustrated by way of Example 19.

Process (G):

This process is applicable to the preparation of acylamino-substituted compounds (I-K), i.e. those of general formula (I) where at least one of $R_{1a}$, $R_{1b}$ and $R_{1c}$ is an aminoalkylcarbonylamino, a lower alkoxycarbonylamino, a mono-lower alkylaminocarbonylamino or a di-lower alkylaminocarbonylamino group, and this process (G) comprises acylating a corresponding amino-substituted compound of formula (I-J). This reaction may be shown by the chemical equation:

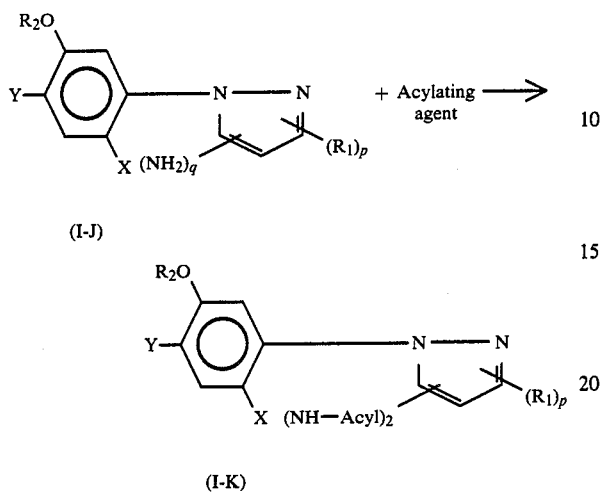

(I-J)

(I-K)

where $R_1$, $R_2$, X, Y, p and q are as defined above and Acyl represents a lower alkylcarbonyl, a lower alkoxycarbonyl, a mono-lower alkylaminocarbonyl or a di-lower alkylaminocarbonyl group.

In cases where the acyl group of the acylating agent to be used in this process (G) is a lower alkylcarbonyl, a lower alkoxycarbonyl or a di-lower alkylaminocarbonyl group, the acylation reaction may be carried out using as acylating agent a lower alkanoic acid chloride a lower alkyl chloroformate or a di-lower alkylcarbamoyl chloride, respectively, in an organic solvent such as benzene, chloroform, tetrahydrofuran, acetone and acetonitrile in the presence of an organic or inorganic acid binding agent, including an organic base such as triethylamine and pyridine and an inorganic base such as anhydrous sodium carbonate and anhydrous potassium carbonate. The reaction temperature may be properly chosen from a temperature under ice-water cooling to the refluxing temperature of the solvent used. After the completion of the reaction, the desired compound may be recovered from the reaction mixture by adding thereto water and an organic solvent such as benzene, toluene, tetrahydrofuran and chloroform, separating the organic layer thus formed and distilling off the organic solvent to leave the desired compound.

In cases where the acyl group of the acylating agent to be used in this process (G) is a mono-lower alkylaminocarbonyl group, the acylation reaction may be conducted by using a lower alkyl isocyanate in an inert solvent such as benzene, ether, tetrahydrofuran and acetone at a temperature ranging from room temperature to the refluxing temperature of the solvent used. The reaction may be accelerated by adding a catalytic amount of a tertiary amine such as triethyl amine or an organotin compound such as dibutyltin diacetate. After the completion of the reaction, the desired compound may be isolated by distilling off the solvent used from the reaction mixture.

Process (G) is illustrated by way of Example 20.

Now, referring back to process (A), the substituted phenylhydrazine compounds of formula (II-A) which is to be used as starting compound are also new compounds. The phenylhydrazine compounds of formula (II-A) where $R_2$ is sulfonyl or a substituted sulfonyl group may be prepared by process (H) given below which starts from a corresponding substituted phenol of formula (V).

Process (H):

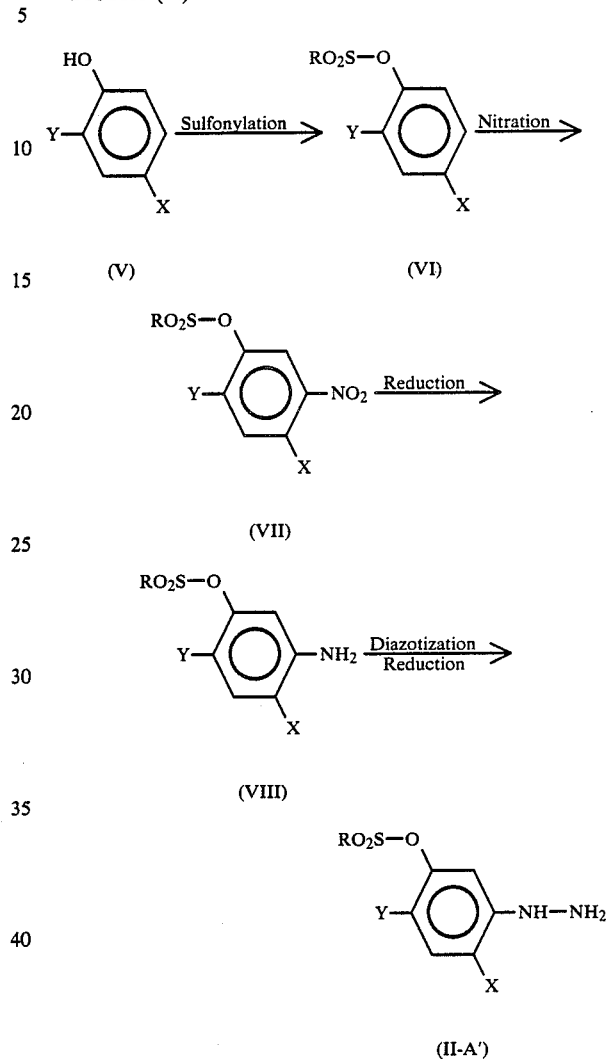

where R is a substituted or unsubstituted alkyl or aryl group.

Intermediate compounds (VI), (VII) and (VIII) given above are also novel compounds.

In process (H), substituted phenol (V) is first reacted with a sulfonyl halide $RSO_2Cl$ or $RSO_2Br$ to cause sulfonylation of the phenolic hydroxyl group to form sulfonyloxy compound (VI). The sulfonylation is preferably carried out in pyridine which may serve not only as solvent but also as the acid binding agent. Usually, this reaction is effected in such a manner that a sulfonyl halide is added dropwise to a mixture of a dihalophenol and pyridine under cooling with ice-cold water, followed by stirring the reaction mixture at room temperature. If a long time is required for the completion of the reaction, heating to a suitable temperature which may be up to the boiling point of pyridine makes it possible to significantly shorten the reaction time. After the reaction, pyridine salt thus deposited is filtered off and the pyridine solvent is distilled off to leave sulfonyloxy compound (VI). This compound may also be obtained from the reaction mixture above by adding water and an organic solvent such as benzene, toluene, tetrahydrofuran and chloroform to extract the compound intended, (VI), washing the extract with a dilute hydrochloric acid to remove pyridine and distilling off the solvent used.

Nitro compound (VII) may be prepared by nitrating sulfonyloxy compound (VI) with nitric acid. The nitration may be carried out under such mixed acid condition as usual. Thus, to a mixture of 95% sulfonic acid and sulfonyloxy compound (VI), is added dropwise a mixture of an equivalent amount of concentrated nitric acid and 95% sulfuric acid under ice-water cooling, followed by stirring the reaction mixture at room temperature until the nitration reaction becomes complete. Thereafter, the reaction mixture is added to ice pieces for dilution, to which an organic solvent such as benzene, toluene, tetrahydrofuran and chloroform is added to extract the desired nitro compound. Then, the solvent is distilled off from the extract to isolate the nitro compound.

Nitro compound (VII) is then reduced by iron to give amino compound (VIII). The reduction may usually be conduced in water as solvent with the addition of a small amount of hydrochloric acid to promote the reaction. Heating the reaction mixture to a temperature of 50°–100° C. is preferred to shorten the reaction time. After the completion of the reaction, the reaction mixture is extracted with an organic solvent such as benzene, toluene, tetrahydrofuran and chloroform. The removal of the solvent from the extract by distillation yields sulfonyloxyamino compound (VIII).

Subsequent diazotizatio of amino compound (VIII) followed by reduction with stannous chloride and hydrochloric acid results in the formation of hydrazino compound (II-A'). The diazotiazation may be effected by adding amino compound (VIII) to aqueous hydrochloric acid, followed by adding an equivalent amount of aqueous sodium nitrite solution dropwise to the resulting mixture at about −20° C. The subsequent reduction may be achieved by adding the resulting diazonium salt solution to an aqueous solution of hydrochloric acid and stannous chloride under ice-cooling, followed by stirring the mixture at room temperature. After the completion of the reaction, the mixture is made weakly alkaline with the addition of an aqueous sodium hydroxide solution, then extracted with an organic solvent such as benzene, toluene, tetrahydrofuran and chloroform. The removal of the solvent from the extract by distillation affords hydrazino compound (II-A').

The preparation of the hydrazine compound (II-A') according to process (H) is illustrated later in Example 22.

Further, various members of compounds of the aforesaid formula (I-A) where $R_2$ is of the sulfonyl type may be prepared in the same manner as that of the aforesaid process (A) above, and they may be used as starting compounds for the preparation of other compounds of general formula (I) where $R_{1a}$, $R_{1b}$, $R_{1c}$ and $R_2$ may have desired meanings within the respective ranges defined above, by utilizing any appropriate process selected from the processes (A) to (G) described hereinbefore.

As stated hereinbefore, any of the processes (A) to (G) described above may be chosen appropriately for the production of the compounds of the general formula (I) depending on the nature of the groups $R_{1a}$, $R_{1b}$, $R_{1c}$ and $R_2$ present in the compound (I) to be produced. The process (A) may be utilized for the production of some members of the compounds of the general formula (I). According to a fourth aspect of this invention, therefore, there is provided a process for the production of a pyrazole derivative of the formula

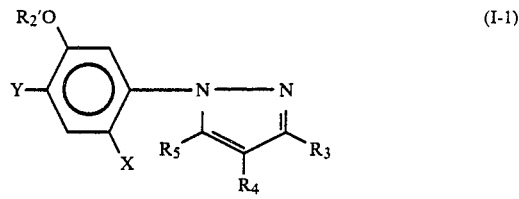

(I-1)

where $R_3$, $R_4$ and $R_5$ each are a hydrogen atom, a (lower) alkyl group, a halo-(lower)alkyl group, a (lower)alkenyl group or a (lower)alkynyl group, $R_2'$ is a (lower)alkyl group, a (lower)alkenyl group, a (lower)alkynyl group, a (lower)alkoxy(lower) alkyl group, a (lower)alkylthio(lower)alkyl group, a (lower)alkylcarbonyl(lower)alkyl group, a (lower)alkoxycarbonyl(lower)alkyl group, a (lower)alkylthiocarbonyl (lower)alkyl group, a cyano(lower)alkyl group, a (lower) alkylsulfonyl group, phenylsulfonyl group, a halogen-substituted phenylsulfonyl group or a (lower)alkyl-substituted phenylsulfonyl group, and X and Y are the same or different and each are a halogen atom, which comprises reacting a hydrazine compound of the formula

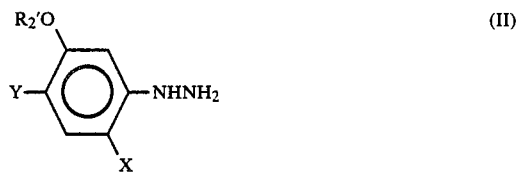

(II)

wherein $R_2'$, X and Y are as defined above, with a dicarbonyl compound of the formula

(III')

wherein $R_3$, $R_4$ and $R_5$ are as defined just above, in a solvent in which the compound of the formula (II) and the compound of the formula (III') are soluble and which is unreactive with both the compounds of the formulae (II) and (III'), at a temperature of from room temperature to the refluxing temperature of said solvent, to produce the compound of the formula (I-1) above.

The reaction invoved in the above process according to the fourth aspect of this invention may be carried out in the same manner as described for the aforesaid process (A).

The process (B) as described above may be utilized for the production of another some compounds amongst the compounds of the formula (I). According to the fifth aspect of this invention, therefore, there is provided a process for the production of a pyrazole derivative of the formula

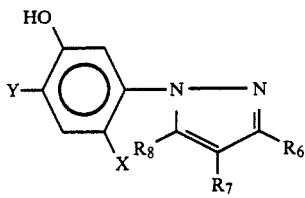
(I-2)

where $R_6$, $R_7$ and $R_8$ are each a hydrogen atom, a halogen atom, a nitro group, an amino group, a (lower)alkyl group, a halo-(lower)alkyl group, a (lower)alkenyl group or a (lower)alkynyl group, and X and Y are the same or different and each are a halogen atom, which comprises hydrolysing a pyrazole compound of the formula

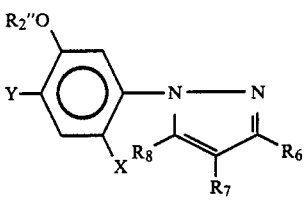
(I-3)

wherein $R_6$, $R_7$ and $R_8$ are as defined above, $R_2''$ is a (lower)alkylsulfonyl group, phenylsulfonyl group, a halogen-substituted phenylsulfonyl group or a (lower)alkyl-substituted phenylsulfonyl group, and X and Y are as defined above, in an aqueous medium at a temperature of from room temperature to the refluxing temperature of the aqueous medium in the presence of a basic compound.

The hydrolysing reaction involved in the above process of the fifth aspect of this invention may be carried out in the same manner as described for the process (B) hereinbefore.

The process (C) as described above may be utilized for the production of further some Compounds amongst the compounds of the formula (I). According to the sixth aspect of this invention, therefore, there is provided a process for the production of a pyrazole derivative of the formula

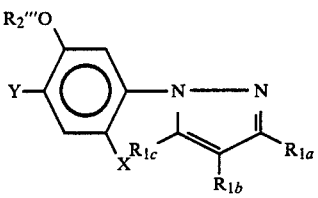
(I-4)

where $R_{1a}$, $R_{1b}$ and $R_{1c}$ are each a hydrogen atom, a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group;

$R_2'''$ is a (lower)alkyl group, a (lower)alkenyl group, a (lower)alkynyl group, a (lower)alkoxy(lower)alkyl group, a (lower)alkylthio(lower)alkyl group, a (lower)alkylcarbonyl(lower)alkyl group, a (lower)alkoxycarbonyl(lower alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower)alkyl-substituted phenylsulfonyl group, and X and Y are the same or different and each are a hydrogen atom, which comprises reacting a pyrazole compound of the formula

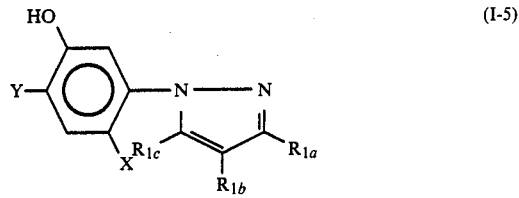
(I-5)

wherein $R_{1a}$, $R_{1b}$, $R_{1c}$, X and Y are as defined above, with a halide compound of the formula

$R_2'''$—Hal (IV)

wherein $R_2'''$ is as defined above and Hal denotes a chlorine, bromine or iodine atom, in an organic solvent in which the compound of the formula (I-5) and the compound of the formula (IV) are soluble and which is unreactive with the compounds of the formulae (I-5) and (IV), at a temperature of from room temperature to the refluxing temperature of said organic solvent, in the presence of an inorganic or organic acid-binding agent.

The reaction involved in this process of the fifth aspect of this invention may be carried out in the same manner as described for the process (C) hereinbefore. This process is most useful to produce the new compounds of this invention.

Tthe processes (D) and (E) as described above may be utilized for the production of further another some compounds amongst the compounds of the formula (I). According to the seventh aspect of this invention, therefore, there is provided a process for the production of a pyrazole derivative of the formula

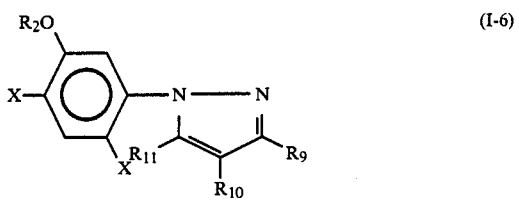
(I-6)

where $R_9$, $R_{10}$ and $R_{11}$ are each a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_9$, $R_{10}$ and $R_{11}$ is or are halogen atom or nitro group, $R_2$ is a hydrogen atom, a (lower)alkyl group, a (lower)alkenyl group, a (lower)alkynyl group, a (lower)alkoxy(lower)alkyl group, a (lower)alkylthio(lower)alkyl group, a (lower)alkylcarbonyl(lower)alkyl group, a (lower) alkoxycarbonyl(lower)alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower) alkyl-substituted phenylsulfonyl group, and X and Y are the same or different and each are a halogen atom, which comprises reacting a pyrazole compound of the formula

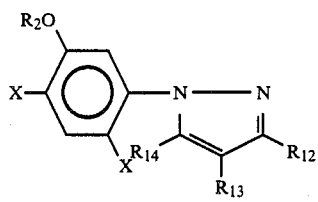
(I-7)

where $R_{12}$, $R_{13}$ and $R_{14}$ are each a hydrogen atom, a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_{12}$, $R_{13}$ and $R_{14}$ is or are hydrogen atom and $R_2$, X and Y are as defined above,- with a halogenating agent or a nitrating agent in a solvent at a temperature of from 0° C. to the refluxing temperature of the solvent as employed, to convert such one or ones of the groups $R_{12}$, $R_{13}$ and $R_{14}$ of the compound (I-7) which is or are the hydrogen atom, into the halo group or nitro group.

The halogenation or nitration involved in this process of the seventh aspect of this invention may be carried out in the same manner as described for the process (D) or (E) hereinbefore.

The process (F) as described above may be utilized for the production of further some compounds amongst the compounds of the formula (1). According to the eighth aspect of this invention, therefore, there is provided a process for the production of a pyrazole derivative of the formula

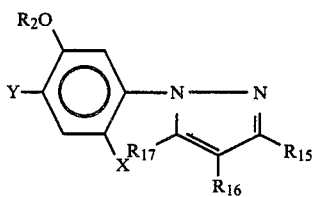
(I-8)

where $R_{15}$, $R_{16}$ and $R_{17}$ each are a hydrogen atom, a halogen atom, an amino group, a (lower)alkyl group, a halo-(lower) alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_{15}$, $R_{16}$ and $R_{17}$ is or are amino group, $R_2$ is a hydrogen atom, a (lower)alkyl group, a (lower) alkenyl group, a (lower)alkynyl group, a (lower)alkoxy(lower) alkyl group, a (lower)alkylthio(-lower)alkyl group, a (lower) alkylcarbonyl(lower)alkyl group, a (lower)alkoxycarbonyl (lower)alkyl group, a (lower)alkylthiocarbonyl(lower)alkyl group, a cyano(-lower)alkyl group, a (lower)alkylsulfonyl group, phenylsulfonyl group, a halogen-substituted phenylsulfonyl group or a (lower)alkylsubstituted phenylsulfonyl group, and X and Y are the same or different and each are a halogen atom, which comprises reacting a pyrazole compound of the formula

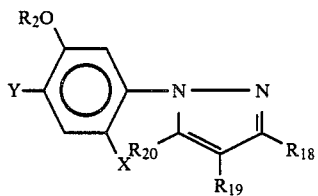
(I-9)

where $R_{18}$, $R_{19}$ and $R_{20}$ each are a hydrogen atom, a halogen atom, an amino group, a (lower)alkyl group, a halo-(lower) alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_{18}$, $R_{19}$ and $R_{20}$ is or are nitro group, $R_2$, X and Y are as defined above, with metallic iron or tin as the reducing agent in the presence of hydrochloric or sulfuric acid or with nascent hydrogen as formed by reaction of metallic iron or tin with hydrochloric or sulfuric acid, in an aqueous medium at a temperature of from 0° C. to the refluxing temperature of the aqueous medium, to convert the nitro group(s) present in the compound (I-9) into the amino group(s). The reduction reaction involved in this process of the eighth aspect of this invention may be carried out in the same manner as described for the process (F) hereinbefore.

The process (G) as described above may be utilized for the production of some compounds amongst the compounds of the formula (I). According to the ninth aspect of this invention, therefore, there is provided a process for the production of a pyrazole derivative of the formula

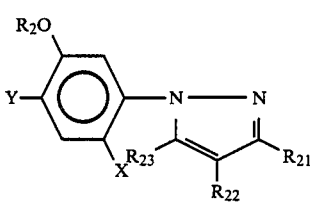
(I-10)

where $R_{21}$, $R_{22}$ and $R_{23}$ each are a hydrogen atom, a halogen atom, a nitro group, a (lower)alkyl group, a halo-(lower) alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_{21}$, $R_{22}$ and $R_{23}$ is or are a (lower)alkylcarbonylamino group, a (lower)alkoxycarbonylamino group, a mono-(lower)alkylaminocarbonylamino group or a di-(lower) alkylaminocarbonylamino group, $R_2$ is a hydrogen atom, a (lower)alkyl group, a (lower) alkenyl group, a (lower)alkynyl group, a (lower)alkoxy(lower) alkyl group, a (lower)alkylthio(-lower)alkyl group, a (lower) alkylcarbonyl(lower)alkyl group, a (lower)alkoxycarbonyl (lower)alkyl group, a (lower)alkylthiocarbonyl(lower)alkyl group, a cyano(-lower)alkyl group, a (lower)alkylsulfonyl group, phenylsulfonyl group, a halogen-substituted phenylsulfonyl group or a (lower)alkylsubstituted phenylsulfonyl group, and X and Y are the same or different and each are a halogen atom, which comprises reacting a pyrazole compouund of the formula

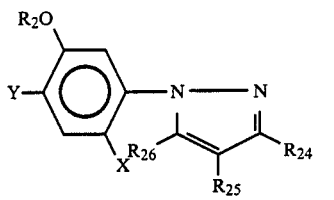

(I-11)

where $R_{24}$, $R_{25}$ and $R_{26}$ each are a hydrogen atom, a halogen atom, nitro group, an amino group, a (lower)alkyl group, a halo-(lower) alkyl group, a (lower)alkenyl group, a (lower)alkynyl group, a (lower)alkylcarbonylamino group, a (lower)alkoxycarbonylamino group, a mono-(lower)alkylaminocarbonylamino group or a di-(lower)alkylaminocarbonylamino group; provided that one, two or three of $R_{24}$, $R_{25}$ and $R_{26}$ is or are amino group, $R_2$, X and Y are as defined above, with a chloride compound of the formula

Q—CO—Cl (IX)

wherein Q is a (lower)alkyl group, a (lower)alkoxy group, a mono-(lower)alkylamino group or a di-(lower)alkylamino, in an organic solvent in which the compounds of the formulae (I-11) and (IX) are soluble, at a temperature of 0° C. to the refluxing temperature of said organic solvent in the presence of an acid binding agent, or with an isocyanate compound of the formula

Q'—N=C=O (X)

wherein Q' is a (lower)alkyl group, in an organic solvent in which the compounds of the formulae (I-11) and the isocyanate compound of the formula (X) are soluble and which is unreactive with the isocyanate compound (VI), at a temperature of from room temperature to the refluxing temperature of said organic solvent, to acylate the amino group(s) present in the compound of the formula (I-11) with the acyl group Q—CO— of the compound (IX) or with the acyl group Q'—NH—CO— as derived from the isocyanate compound (X).

The acylation reaction involved in this process of the ninth aspect of this invention may be carried out in the same manner as described for the process (G) hereinbefore.

Now, the herbicidal composition according to the second aspect of this invention is described in particular.

The herbicidal composition according to the second aspect of this invention may be, for example, in the form of aqueous solution, dispersion, emulsion, dusting powder, wettable powder, flowable powder (sol), driftless (DL-type) powder, granules, fine granules, tablets and others. Any form of the composition above-mentioned may be prepared from the compounds of formula (I) according to conventional formulation techniques. Any desired solid or liquid carrier or diluent may be used which has been used conventionally in the preparation of agricultural or horticultural chemical compositions.

Suitable solid carriers or diluents include mineral powders such as kaolin, bentonite, clay, montmorillonite, talc, diatomaceous earth, mica, vermiculite, gypsum, calcium carbonate, apatite, white carbon, slaked lime, siliceous sand, ammonium sulfate and urea; vegetable powders such as soya bean flour, wheat flour, wood meal, tobacco powder, starch and crystalline cellulose; macromolecular compounds such as petroleum resin, polyvinyl chloride, ketone resin and dammar gum; alumina, silicates, sugar polymers, high-dispersible silicic acid and waxes.

Suitable liquid carriers or diluents include water; alcohols such as methanol, ethanol, n-propanol, i-propanol, butanol, ethylene glycol and benzyl alcohol, aromatic hydrocarbons such as toluene, benzene, xylene, ethylbenzene, and methyl naphthalene; halogenated hydrocarbons such as chloroform, carbon tetrachloride, dischloromethane, chloroethylene, monochlorobenzene, trichlorofluoromethane and dichlorodifluoromethane; ethers such as ethylether, ethylene oxide, dioxane and tetrahydrofuran; ketones such as acetone, methyl ethyl ketone, cyclohexanone, methyl isobutyl ketone and isophorone; esters such as ethyl acetate, butyl acetate, ethylene glycol acetate and amyl acetate; acid amides such as dimethylformamide and dimethylacetamide; nitriles such as acetonitrile, propionitrile and acrylonitrile; sulfoxides such as dimethylsulfoxide; alcoholethers such as ethylene glycol monomethylether and ethylene glycol monoethylether; aliphatic and cycloaliphatic hydrocarbons such as n-hexane and cyclohexane; industrial gasoline such as petroleum ether and solvent naphtha; and petroleum fractions such as paraffins, kerosene and gas oil.

In the preparation of emulsion, dispersion, wettable powder, flowable powder and the like, one or more surface active agents are used for the purpose of emulsification, dispersion, solubilization, wetting, foaming, lubrication, spreading or the like. Surface active agents may be of non-ionic, anionic, cationic or amphoteric type. Suitable agents of the non-ionic type include for example polyoxyethylene alkylethers, polyoxyethylene alkylesters, polyoxyethylenesorbitan alkylesters and sorbitan alkylesters. Suitable agents of the anionic type include, for example, soaps, alkylbenzene sulfonates, alkylsulfosuccinates, alkyl sulphates, polyoxyethylene alkylsulfates and aryl sulfonates. Suitable agents of the cationic type include alkylamines such as laurylamine, stearyl trimethyl ammonium chloride and alkyl dimethyl benzyl ammonium chloride; and polyoxyethylene alkylamines. Suitable agents of the amphoteric type include carboxylic acids of betaine type and salts of sulfuric esters.

In addition to the carriers or diluents and surface active agents, the herbicidal composition may contain a variety of additives, as desired. Such additives include for example polyvinyl alcohol, carboxymethylcellulose, gum arabic, polyvinyl acetate, gelatine, casein, sodium alginate and tragacanth gum.

The herbicidal compositions according to this invention may be formulated in any desired form as exemplified above in which the compound of formula (I) is present in an amount of 0.001 to 95% by weight, preferably 0.01 to 90% by weight. For example, the content of the compounds of formula (I) may usually be 0.01 to 5% by weight when formulated in the form of powder, DL powder or fine granules (F), 0.01 to 10% by weight in the form of granules, and 1 to 75% by weight in the form of wettable powder, aqueous emulsion or solution.

The herbicidal compositions in the form of granules, for example, may be applied as such by dusting them on the surface of or in the soil or in aquatic medium in an amount of about 0.3 to 300 g of the active ingredient per 10 ares. In cases of sol powder, emulsions or wettable powder, the compositions are usually diluted with water or an appropriate solvent and the diluted compositions are applied at a rate of about 0.3 to 300 g of the active ingredient per 10 ares.

When the compounds of this invention, as such or in the form of a composition, are used as herbicides, they may be used, if desired, in combination with one or more of known herbicides, insecticides, fungicides, plantgrowth regulating agents and others for extending the application range of the compounds with a possibility of synergism resulting from such combinations in some cases.

Examples of other herbicides which may be used in combination with the compounds of this invention include the following.

Triazine herbicides 6-chloro-N-ethyl-N'-isopropyl-1,3,5-triazin-2-yl-2,4-diamine
6-chloro-N,N'-diethyl-1,3,5-triazin-2,4-diyldiamine
N-ethyl-N'-isopropyl-6-methylthio-1,3,5-triazin-2,4-diyldiamine
N-N'di-isopropyl-6-methylthio-1,3,5-triazine-2,4-diyldiamine
N,N'-diethyl-6-methylthio-1,3,5-triazin-2,4-diyldiamine
N-(1,2-dimethylpropyl)-N'-ethyl-6-methylthio-1,3,5-triazin-2-yl-2,4-diamine
2-(4-chloro-6-ethylamino-1,3,5-triazin-2-ylamino)-2-methylpropionitrile
3-cyclohexyl-6-dimethylamino-1-methyl-1,3,5-triazin-2,4(1H,3H)-dione
4-amino-6-tert-butyl-3-methylthio-1,2,4-triazin-5(4H)-one
4-amino-3-methyl-6-phenyl-1,2,4-triazin-5(4H)-one

Amide Herbicides 2-chloro-2',6'-diethyl-N-methoxymethylacetanilide
2-chloro-6'-ethyl-N-(2-methoxy-1-methylethyl)acetortho-toluidine
N-butoxymethyl-2-chloro-2',6'-diethylacetanilide
2-chloro-2',6'-diethyl-N-(2-propoxyethyl)acetanilide
2-chloro-N-isopropylacetanilide
3',4'-dichloropropionanilide
N-1-naphthylphthalamic amide
Ethyl N-benzoyl-N-(3,4-dichlorophenyl)-D,L-alaninate
N,N-dimethyldiphenylacetamide
3,5-dichloro-N-(1,1-dimethylpropynyl)benzamide
5'-(trifluoromethansulfonamido)acet-2',4'-xylidide
N-(α,α-dimethylbenzyl)-2-bromo-3,3,-dimethylbutaamide
N-methyl-2-(benzthiazol-2-yloxy)acetanilide

Carbamate Herbicides

S-4-chlorobenzyl diethyl(thiocarbamate)
S-ethyl azepin-1-carbothioate
S-propyl dipropyl(thiocarbamate)
S-ethyl dipropyl(thiocarbamate)
S-ethyl diisobutyl(thiocarbamate)
S-propyl butyl(ethyl)thiocarbamate
S-ethyl N-cyclohexyl-N-ethyl(thiocarbamate)
S-2,3-dichloroallyl diisopropyl(thiocarbamate)
Isopropyl carbanilate
Methyl 3,4-dichlorocarbanilate
Methyl sulfanylcarbamate
Methyl 3-(3-methylcarbanyloyloxy)carbanilate
S-isopropyl hexahydro-1H-azepin-1-carbothioate
S-3-chloropropyl 3,6-dimethylhexahydro-1H-azepin-1-carbothioate
S-α,α-dimethylbenzyl piperidin-1-carbothioate

Urea Herbicides 3-(4-chlorophenyl)-1,1-dimethylurea
3-(3,4-dichlorophenyl)-1-methoxy-1-methylurea
3-(3,4-dichlorophenyl)-1,1-dimethylurea
1,1-dimethyl-3-(α,α,α-trifluoro-meta-tolyl)urea
3-(4-bromo-3-chlorophenyl)-1-methoxy-1-methylurea
3-(3-chloro-4-methoxyphenyl)-1,1-dimethylurea
3-para-cumenyl-1,1-dimethylurea
3-[4-(4-chlorophenoxy)phenyl]-1,1-dimethylurea
1-(2-methylcyclohexyl)-3-phenylurea
1-benzothiazol-2-yl-3-methylurea
1-benzothiazol-2-yl-1,3-dimethylurea
1-(5-tert-butyl-1,3,4-thiadiazol-2-yl)-1,3-dimethylurea
3-(5-tert-butyl-1,3,4-thiadiazol-2-yl)-4-hydroxy-1-methyl-2-imidazolidone
1-(2-chlorophenylsulfonyl)-3-(4-methoxy-6-methyl-1,3,5-triazin-2-yl)urea
Methyl 2-{[(4,6-dimethoxy-pyrimidin-2-yl)amino-carbonyl]aminosulfonylmethyl)}benzoate
1-(α,α-dimethylbenzyl)-3-(para-tolyl)urea

Toluidine Herbicides

α,α,α-trifluoro-2,6-dinitro-N,N-dipropyl-paratoluidine
N-(1-ethylpropyl)-2,6-dinitro-3,4-xylidine
$N_1,N^1$-diethyl-2,6-dinitro-4-trifluoromethyl-metaphenylenediamine
N-(2-chloroethyl)-α,α,α-trifluoro-2,6-dinitro-N-propyl-para-toluidine
4-methylsulfonyl-2,6-dinitro-N,N-dipropylaniline

Diazine Herbicides 5-tert-butyl-3-(2,4-dichloro-5-isopropoxyphenyl)-1,3,4-oxadiazol-2(3H)-one
2-(3,4-dichlorophenyl)-4-methyl-1,2,4-oxadiazolidine-3,5-dione
3-isopropyl-(1H)-2,1,3-benzothiadiazin-4(3H)-one 2,2-dioxide
4-(2,4-dichlorobenzoyl)-1,3-dimethylpyrazol-5-yl-paratoluene sulfonate
1,3-dimethyl-4-(2,4-dichlorobenzoyl)-5-phenacyloxypyrazole

Diphenylether Herbicides 5-(2-chloro-α,α,α-trifluoro-para-tolyloxy)-2-nitrobenzoic acid
2-chloro-1-(3-ethoxy-4-nitrophenoxy)-4-(trifluoromethyl)benzene
2,4-dichlorophenyl-3-methoxy-4'-nitrophenylether
2,4,6-trichlorophenyl-4'-nitrophenylether
Methyl 5-(2,4-dichlorophenoxy)-2-nitrobenzoate

Phenoxyaliphatic Acid Herbicides 2-methyl-4-chlorophenoxyacetic acid and its salts, esters and amide derivatives
2,4-dichlorophenoxyacetic acid and its salts, esters and amide derivatives
±-2-(4-chloro-2-methylphenoxy)propionic acid and its salts, esters and amide derivatives
4-(4-chloro-o-tolyloxy)butyric acid and its salts, esters and amide derivatives
S-ethyl 4-chloro-o-tolyloxythioacetate 2-(2,4-dichloro-3-methylphenoxy)propionanilide
α-(2-naphthyloxy)propionanilide
(RS)-N,N-diethyl-2-(1-naphthyloxy)propionamide
(RS)-2-[4-(2,4-dichlorophenoxy)phenoxy]propionic acid and its ester derivatives
(RS)-2-[4-(5-trifluoromethyl-2-pyridyloxy)phenoxy]propionic acid and its ester derivatives
(RS)-2-[4-(3-chloro-5-trifluoromethyl-2-pyridyloxy)phenoxy]propionic acid and its ester derivatives
(RS)-2-[4-(3,5-dichloro-2-pyridyloxy)phenoxy]propionic acid and its salts, esters and amide derivatives
(RS)-2-[4-(6-chloroquinoxalinyloxy)phenoxy]propionic acid and its ester derivatives

Organophosphorus Herbicides

N-(phosphonomethyl)glycine and its salt derivatives
D,L-homoalanine-4-yl(methyl)phosphinic acid and its salt derivatives
2-amino-4-[(hydroxy)(methyl)phosphionyl]-butyrylalanylalanine and its salt derivatives
O-ethyl O-6-nitro-meta-tolyl sec-butylphosphoroamidothioate
S-4-chloro-N-isopropylcarbanyloxymethyl O,O-dimethylphosphorodithioate
S-2-methylpiperidinocarbonylmethyl O,O-dipropylphosphorodithioate
S-2-benzensulfonamidoethyl O,O-di-isopropylphosphorodithioate

Nitrile Herbicides 2,6-dichlorobenzonitrile
2,6-dichloro(thiobenzamide)
3,5-dibromo-4-hydroxybenzonitrile
4-hydroxy-3,5-di-iodobenzonitrile

Uracil Herbicides 5-bromo-3-sec-butyl-6-methyluracil
3-cyclohexyl-1,5,6,7-tetrahydrocyclopentapyrimidin-2,4(3H)-dione
3-tert-butyl-5-chloro-6-methyluracil

Benzoic Acid Herbicides 3-amino-2,5-dichlorobenzoic acid and its salt derivatives
3,6-dichloro-ortho-anisic acid and its salt derivatives
2,3,5,6-tetrachloroterephthalic acid and its salts, esters and amide derivatives

Phenolic Herbicides 2-sec-butyl-4,6-dinitrophenol and its salts and carboxylate ester derivatives
4,6-dinitro-ortho-cresol and its salts and carboxylate ester derivatives

Quaternary Ammonium Herbicides 1,1'-dimethyl-4,4'-bipyridinium dichloride
1,1'-ethylene-2,2'-bipyridinium dibromide

Pyridazine Herbicides 5-amino-4-chloro-2-phenylpyridazin-3(2H)-one
4-chloro-5-methylamino-2-(α,α,α-trifluoro-metatolyl)-pyridazin-3(2H)-one

Pyridine Herbicides 4-amino-3,5,6-trichloropyridin-2-carboxylic acid and its salt derivatives
3,5,6-trichloro-2-pyridyloxyacetic acid and its salt and ester derivatives
1-methyl-3-phenyl-5-(α,αα-trifluoro-meta-tolyl)-4-pyridone

Other Herbicides 3-(chloro-2-amino-1,4-naphthoquinomethyl 3-[1-(allyloxyimino)butyl]-4-hydroxy-6,6-dimethyl-2oxocyclohexa-3-encarboxylate and its salt derivatives
(±)-2-(1-ethoxyiminobutyl)-5-[2-(ethylthio) propyl]-3-hydroxycyclohexa-2-enone
1,2-dimethyl-3,5-diphenylpyrazoliummethylsulphate.

This invention is now illustrated, but not limited, by the following examples. In Examples, all parts and percentages are by weight, unless otherwise stated.

EXAMPLE 1

Preparation of 1-(2-fluoro-4-chloro-5-methylsulfonyloxyphenyl)-3,5-di-trifluoromethylpyrazole (Compound No. 25) (Process A)

A mixture of (2-fluoro-4-chloro-5-methylsulfonyloxyphenyl)-hydrazine (25.5 g), 1,1,1,5,5,5-hexafluoropenta-2,4-dione (20.8 g), ethanol (100 ml) and water (100 ml) was heated to reflux for one hour. After the reaction mixture was cooled, toluene was added thereto to form two layers. The toluene layer separated was washed with water and dried over anhydrous sodium sulfate. Removal of the solvent by distillation under reduced pressure gave the titled compound (40.1 g) as a pale brown crystalline solid. Recrystallization of this solid from a mixture of cyclohexane and ethyl acetate afforded a white crystalline solid. m.p. 87°–89.5° C.

EXAMPLE 2

Preparation of 1-(2,4-dichloro-5-isopropoxyphenyl)-3,5-di-trifluoromethylpyrazole (Compound No. 27) (Process A)

(2,4-dichloro-5-isopropoxyphenyl)hydrazine (23.5 g) was admixed with 1,1,1,5,5,5-hexafluoropenta-2,4-dione (20.8 g) and the resultant admixture was slowly warmed and maintained at 120° C. for one hour. After the reaction mixture was cooled, toluene was added thereto and the mixture was washed with an aqueous dilute hydrochloric acid solution and then with water and dried over anhydrous sodium sulfate. Removal of the solvent by distillation under reduced pressure gave the titled compound (37.4 g) as a pale yellow oil. Purification of this oil by silica gel column chromatography yielded a colorless oil. $n_D^{23} = 1.5478$.

EXAMPLE 3

Preparation of 1-(2-fluoro-4-chloro-5-methylsulfonyloxyphenyl)-3,4,5-trimethylpyrazole (Compound No. 148) (Process A)

A mixture of (2-fluoro-4-chloro-5-methylsulfonyloxyphenyl)hydrazine (25.5 g) of the formula:

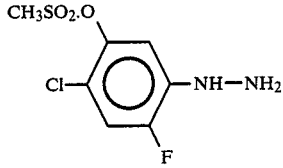

3-methylpenta-2,5-dione (CH$_3$COCH(CH$_3$)COCH$_3$) (11.4 g), ethanol (100 ml) and water (100 ml) was heated to reflux for one hour. After the reaction mixture was cooled, toluene was added thereto to form two layers. The toluene layer separated was washed with water and dried over anhydrous sodium sulfate. Removal of the solvent by distillation in vacuo gave the titled compound (29.3 g) as a pale yellow crystalline solid. Recrystallization of this solid from a mixture of n-hexane and ethyl acetate afforded a white crystalline solid. m.p. 123°–125° C.

EXAMPLE 4

Preparation of 1-(2-fluoro-4-chloro-5-phenylsulfonyloxyphenyl)-3,4,5-trimethylpyrazole (Compound No. 150) (Process A)

A mixture of (2-fluoro-4-chloro-5-phenylsulfonyloxyphenyl)-hydrazine (31.7 g), 3-methylpenta-2,4-dione (11.4 g) and water (150 ml) was stirred at 70° C. for one hour. After the reaction mixture was cooled, toluene was added thereto whereby to form two layers. The toluene layer thus separated was washed with water and dried over anhydrous sodium sulfate. Removal of the solvent by distillation in vacuo gave the titled compound (37.5 g) as a pale brown crystalline solid. Recrystallization of this solid from carbon tetrachloride afforded a white crystalline solid. $n_D^{23} = 1.5492$.

EXAMPLE 5

Preparation of 1-(2-fluoro-4-chloro-5-propargyloxyphenyl)-3,4,5-triethylpyrazole (Compound No. 167) (Process A)

(2-fluoro-4-chloro-5-propargyloxyphenyl)hydrazine (21.5 g) and 4-ethylhepta-3,5-dione (15.6 g) were reacted with each other and processed in the same manner as in Example 1 to afford the titled compound (30.1 g) as a pale yellow oil. Purification of this oil by silica gel column chromatography gave a white crystalline solid. m.p. 62°–65° C.

EXAMPLE 6

Preparation of 1-(2-fluoro-4-chloro-5-hydroxyphenyl)-3,5-dimethyl-4-nitropyrazole (Compound No. 37) (Process B)

A mixture of 1-(2-fluoro-4-chloro-5-methylsulfonyloxyphenyl)-3,5-dimethyl-4-nitropyrazole (36.5 g), 2N aqueous sodium hydroxide solution (100 ml) and ethanol (50 ml) was stirred at 40° C. for 30 minutes. After cooling, the reaction mixture was acidified with an aqueous hydrochloric acid solution and extracted with toluene. The toluene layer thus obtained was washed with water and dried over anhydrous sodium sulfate. Removal of the solvent by distillation in vacuo gave the titled compound (28.1 g) as a pale yellow crystalline solid. Recrystallization of this solid from a mixture of n-hexane and ethyl acetate afforded a white crystalline solid. m.p. 157°–158° C.

EXAMPLE 7

Preparation of 1-(2-fluoro-4-chloro-5-hydroxyphenyl)-3,4,5-trimethylpyrazole (Compound No. 122) (Process B)

A mixture of 1-(2-fluoro-4-chloro-5-methylsulfonyloxyphenyl)- 3,4,5-trimethylpyrazole (33.3 g), 2N aqueous sodium hydroxide (100 ml) and ethanol (50 ml) was stirred at 40° C. for 30 minutes. After cooling, the reaction mixture was acidified with aqueous hydrochloric acid and then extracted wth toluene. The toluene layer thus obtained was washed with water and dried over anhydrous sodium sulfate. Removal of the solvent by distillation in vacuo gave the titled compound (24.2 g) as a pale yellow crystalline solid. Recrystallization of this solid from a mixture of n-hexane/ethyl acetate yielded a white crystalline solid. m.p. 158°–160° C.

EXAMPLE 8

Preparation of 1-(2,4-dichloro-5-hydroxyphenyl)-3,5-di-methyl-4-chloropyrazole (Compound No. 173) (Process B)

A mixture of 1-(2,4-dichloro-5-methylsulfonyloxyphenyl)-3,5-dimethyl-4-chloropyrazole (37.0 g) and 2N aqueous sodium hydroxide was stirred at 50° C. for 30 minutes. After cooling, the reaction mixture was acidified with aqueous hydrochloric acid and then extracted with toluene. The resulting toluene layer was washed with water and dried over anhydrous sodium sulfate. Removal of the solvent by distillation in vacuo gave the titled compound (26.8 g) as a pale yellow crystalline solid. Recrystallization of this solid from a mixture of n-hexane/ethyl acetate afforded a white crystalline solid. m.p. 172°–174° C.

EXAMPLE 9

Preparation of 1-(2-fluoro-4-chloro-5-propargyloxyphenyl)-3,5-dimethyl-4-nitropyrazole (Compound No. 47) (process C)

A mixture of 1-(2-fluoro-4-chloro-5-hydroxyphenyl)-3,5-dimethyl-4-nitropyrazole (28.7 g), propargy bromide (13.1 g), anhydrous potassium carbonate (15.2 g) and acetonitrile (200 ml) was stirred at 60° C. for 2 hours. After cooling, the reaction mixture was filtered through a filter to remove crystalline solid matters and the filtrate was concentrated to a small volume under reduced pressure. The concentrated solution was admixed with toluene and water to form two layers. The toluene layer formed (the extract) was separated, washed with water and then dried over anhydrous sodium sulfate. Removal of the solvent by distillation in vacuo gave the titled compound (31.2 g) as a pale yellow crystalline solid. Recrystallization of this solid from a mixture of n-hexane/ethyl acetate yielded a white crystalline solid. m.p. 125°–126.5° C.

EXAMPLE 10

Preparation of 1-(2-fluoro-4-chloro-5-isopropyloxyphenyl)-3,4,5-trimethylpyrazole (Compound No. 129) (Process C)

A mixture of 1-(2-fluoro-4-chloro-5-hydroxyphenyl)-3,4,5-trimethylpyrazole (25.5 g), isopropyl iodide (18.7 g), anhydrous potassium carbonate (14.5 g) and dimethylsulfoxide (200 ml) was stirred at 80° C. for one hour. After cooling, the reaction mixture was admixed with water and toluene to form two layers. The toluene layer formed was separated, washed with water and then dried over anhydrous sodium sulfate. Removal of the solvent by distillation in vacuo gave the titled compound (31.1 g) as a pale yellow oil, which was then purified through silica gel column chromatography to yield a colorless oil. $n_D^{23} = 1.5406$.

EXAMPLE 11

Preparation of 1-(2-fluoro-4-chloro-5-allyloxyphenyl)-3,4,5-trimethylpyrazole (Compound No. 136) (Process C)

A mixture of 1-(2-fluoro-4-chloro-5-hydroxyphenyl)-3,4,5-trimethylpyrazole (25.5 g), allyl bromide (13.3 g), anhydrous potassium carbonate (14.5 g) and acetonitrile (150 ml) was heated under reflux, with stirring for 3 hours. After cooling, the reaction mixture was filtered through a filter to remove the inorganic salts therefrom and the filtrate was concentrated to a small volume under reduced pressure, affording the titled compound (28.7 g) as a pale brown crystalline solid. Recrystallization of this solid from cyclohexane yielded a white crystalline solid. m.p. 97°–99° C.

EXAMPLE 12

Preparation of 1-(2-fluoro-4-chloro-5-ethoxycarbonylmethyloxyphenyl)-3,5-dimethyl-4-chloropyrazole (Compound No. 187) (Process C)

1-(2-fluoro-4-chloro-5-hydroxyphenyl)-3,5-dimethyl-4-chloropyrazole (27.5 g) was dissolved in tetrahydrofuran (200 ml), and to the resultant solution was added sodium amide (4.0 g). When the evolution of ammonia gas from the reaction mixture ceased, ethyl monochloroacetate (12.3 g) was added dropwise to the reaction mixture. After the completion of addition, the reaction mixture was heated under reflux, with stirring for further 3 hours. To the reaction mixture, after cooling, were added toluene and water to form two layers. The organic layer as separated was washed with water and dried over anhydrous sodium sulfate. Removal of the solvent by distillation in vacuo gave the titled compound (33.9 g) as a pale brown crystalline solid. Recrystallization of this solid from cyclohexane afforded a white crystalline solid. m.p. 101°–104° C.

EXAMPLE 13

Preparation of 1-(2,4-dichloro-5-isopropoxyphenyl)-3,4,5-trimethylpyrazole (Compound No. 132) (Process C)

A mixture of 1-(2,4-dichloro-5-hydroxyphenyl)-3,4,5-trimethylpyrazole (27.1 g), isopropyl bromide (12.3 g), aqueous sodium hydroxide (4.2 g) and dimethylformamide (150 ml) was stirred at 70° C. for 2 hours. To the reaction mixture, after cooling, were added water and toluene, to form two layers. The toluene layer as separated was washed with water and then dried over anhydrous sodium sulfate. Removal of the toluene by distillation in vacuo gave the titled compound (27.9 g) as a pale yellow oil, which was then purified through silica gel column chromatography to afford a white crystalline solid. m.p. 56°–58° C.

EXAMPLE 14

Preparation of 1-(2,4-dichloro-5-propargyloxyphenyl)-3,5-dimethyl-4-chloropyrazole (Compound No. 140) (Process C)

1-(2,4-dichloro-5-hydroxyphenyl)-3,5-dimethyl-4-chloropyrazole (29.2 g) and propargyl bromide (12.0 g) were added to a solution of sodium methoxide which was previously prepared from metallic sodium (2.3 g) and methanol (200 ml). The resulting mixture was heated under reflux, with stirring for 3 hours. To the reaction mixture, after cooling, were added water and toluene to form two layers. The toluene layer as formed was separated, washed with water and then dried over anhydrous sodium sulfate. Removal of the solvent by distillation in vacuo gave the titled compound (30.1 g) as a pale brown crystalline solid. Recrystallization of this solid from a mixture of cyclohexane/acetone afforded a white crystalline solid. m.p. 156.5°–158° C.

EXAMPLE 15

Preparation of 1-(2-fluoro-4-chloro-5-methylsulfonyloxyphenyl)-3-trifluoromethyl-4-chloro-5-methylpyrazole (Compound No. 81) (Process D)

Into a solution of 1-(2-fluoro-4-chloro-5-methylsulfonyloxyphenyl)-3-trifluoromethyl-5-methylpyrazole (37.3 g) in chloroform (200 ml) was introduced chlorine gas (7.1 g) at 60° C. for 20 minutes. Removal of the solvent from the reaction solution by distillation in vacuo gave the titled compound (40.2 g) as a pale yellow oil which soon crystallized on standing at room temperature. Recrystallization from a mixture of n-hexane/benzene yielded a white crystalline solid. m.p. 72°–74.5° C.

EXAMPLE 16

Preparation of 1-(2-fluoro-4-chloro-5-methylsulfonyloxyphenyl)-3,5-dimethyl-4-chloropyrazole (Compound No. 189) (Process D)

Into a solution of 1-(2-fluoro-4-chloro-5-methylsulfonyloxyphenyl)-3,5-dimethylpyrazole (31.9 g) in chloroform (200 ml) was introduced chlorine gas (7.1 g) for 10 minutes under water-cooling, and then the reaction mixture was stirred for further 30 minutes to effect the chlorination reaction. Removal of the solvent from the reaction solution by distillation in vacuo gave the titled compound (35.2 g) as a pale brown oil. Purification of this oil by silica gel column chromatography yielded a colorless oil. $n_D^{23} = 1.5431$.

EXAMPLE 17

Preparation of 1-(2-fluoro-4-chloro-5-ethoxylphenyl)-3,5-dimethyl-4-chloropyrazole (Compound No. 175) (Process D)

To a solution of 1-(2-fluoro-4-chloro-5-ethoxyphenyl)-3,5-dimethylpyrazole (26.9 g) in chloroform (200 ml) was added dropwise sulfuryl chloride (13.5 g) for 10 minutes under water-cooling, and the reaction mixture was stirred for further 30 minutes to effect the chlorination reaction. Removal of the solvent from the reaction solution by distillation in vacuo gave the titled compound (30.0 g) as a pale yellow crystalline solid. After recrystallization of the solid from a mixture of n-hexane/ethyl acetate, the resulting white crystalline product showed the melting point of 106°–107.5° C.

EXAMPLE 18

Preparation of 1-(2-fluoro-4-chloro-5-methylsulfonyloxyphenyl)-3,5-dimethyl-4-nitropyrazole (Compound No. 52) (Process E)

To 1-(2-fluoro-4-chloro-5-methylsulfonyloxyphenyl)-3,5-dimethylpyrazole (31.9 g) was added 95% sulfuric acid (35 ml) and then added dropwise an acid mixture of 95% sulfuric acid (7.5 ml) and 61% nitric acid (10.3 g) under cooling with iced water, and the reaction mixture was stirred at room temperature for further one hour, and was then poured into iced water. The reaction mixture was extracted with toluene and the resulting toluene layer was washed with 1N aqueous sodium hydroxide solution and then with water and dried over anhydrous sodium sulfate. Removal of the solvent from the extract in toluene by distillation in vacuo gave the titled compound (33.1 g) as a yellowish brown crystalline solid. Recrystallization of the solid from a mixture of cyclohexane/acetone yielded a pale yellow crystalline solid. m.p. 150.5°–152.5° C.

EXAMPLE 19

Preparation of 1-(2-fluoro-4-chloro-5-isopropoxyphenyl)-3,5-dimethyl-4-aminopyrazole (Compound No. 69) (Process F)

1-(2-fluoro-4-chloro-5-isopropoxyphenyl)-3,5-dimethyl-4-nitropyrazole (32.8 g) and metallic iron (33.5 g) were suspended in water (140 ml), and the resultant suspension was heated at 80° C., to which 35% aqueous hydrochloric acid (3.2 g) was then added dropwise. After the completion of addition, the reaction mixture was stirred for further 30 minutes at 80° C. Subsequent to cooling, the reaction mixture was brought to pH 9 with aqueous sodium hydroxide solution, followed by addition of toluene to form two layers. The organic layer as separated was washed with water and dried over anhydrous sodium sulfate. Removal of the solvent by distillation in vacuo gave the titled compound (27.7 g) as a pale yellow oil which soon crystallized on standing at room temperature. Recrystallization from a mixture of n-hexane/ethyl acetate yielded a white crystalline solid. m.p. 94°–96.5° C.

EXAMPLE 20

Preparation of 1-(2-fluoro-4-chloro-5-isopropoxyphenyl)-3,5-dimethyl-4-methylaminocarbonylaminopyrazole (Compound No. 74) (Process G)

To a solution of 1-(2-fluoro-4-chloro-5-isopropoxyphenyl)-3,5-dimethyl-4-aminopyrazole (29.8 g) in tetrahydrofuran (100 ml) was added one drop of triethylamine and then added dropwise a solution of methyl isocyanate (6.0 g) in tetrahydrofuran (50 ml). After the completion of addition, the reaction mixture was left to stand at room temperature for one hour. Removal of the solvent from the reaction solution by distillation in vacuo gave the titled compound (34.7 g) as a white crystalline solid. Recrystallization of the solid from a mixture of cyclohexane/acetone provided a white crystalline solid. m.p. 184°–185° C.

EXAMPLE 21

Preparation of 1-(2-fluoro-4-chloro-5-methylsulfonyloxyphenyl)-3,5-dimethylpyrazole (Compound No. 112) [Process A]

A mixture of 2-fluoro-4-chloro-5-methylsulfonyloxyphenylhydrazine (25.5 g), acetylacetone (10.0 g), ethanol (100 ml) and water (100 ml) was refluxed for 2 hours. After cooling, toluene was added to the reaction mixture to separate layers. The toluene layer as separated was washed with water and then subjected to distillation under a reduced pressure to remove the toluene, yielding the titled compound (29.3 g) as pale yellow crystals. Recrystallization from a mixture of hexane/ethyl acetate gave colorless crystals with melting point 77.5°–79° C.

EXAMPLE 22

(a) Preparation of 2-chloro-4-fluorophenyl methanesulfonate

To a mixture of 2-chloro-4-fluorophenol (14.7 g) and methylsulfonyl chloride (11.5 g), under ice-cooling, pyridine (30 g) was added dropwise. The resulting mixture was stirred at room temperature for 30 minutes to complete the methylsulfonylation, after which the pyridine was distilled off under reduced pressure. Toluene and water were added to the residue and the mixture was washed with a dilute aqueous hydrochloric acid, then with water. The toluene layer as separated was dried over anhydrous sodium sulfate and then the toluene was distilled off to afford the titled compound (20.8 g) as a pale yellow oil. After purification by silica gel chromatography, the oil was made colorless with a refractive index $n_D^{23} = 1.5117$.

(b) Preparation of 2-chloro-4-fluoro-5-nitrophenyl methanesulfonate

A 95% sulfuric acid (35 ml) was added to 2-chloro-4-fluorophenyl methanesulfonate (22.5 g), to which was then added dropwise a mixture of 95% sulfuric acid (7.5 ml) and 61% nitric acid (10.3 g) under ice-water cooling and stirring to effect nitration reaction. After the completion of the addition, the reaction mixture was stirred for further 30 minutes at room temperature and then poured onto ice pieces and extracted with toluene. The toluene extract as separated was washed with 1N aqueous sodium hydroxide solution and then with water and dried over anhydrous sodium sulfate. The toluene was distilled off to afford the titled compound (25.9 g) as pale yellow crystals with melting point 64°–65.5° C.

(c) Preparation of 2-chloro-4-fluoro-5-aminophenyl methanesulfonate

A suspension of 2-chloro-4-fluoro-5-nitrophenyl methanesulfonate (27.0 g) and iron (33.5 g) in water (140 ml) was heated for reduction of the nitro group into amino group. When the temperature of the reaction mixture reached 80° C., 35% hydrochloric acid (3.2 g) was added thereto. Upon cooling to room temperature, the pH of the reaction mixture was adjusted to 9.0 with the addition of an aqueous sodium hydroxide solution. The reaction mixture was then extracted with toluene and tetrahydrofuran. The organic layer so separated was washed with water, dried over anhydrous sodium sulfate and then distilled under reduced pressure to remove the solvent, affording the titled compound (22.3 g) as a pale yellow oil which was then purified by silica gel chromatography to give colorless crystals with melting point 79°–80° C.

(d) Preparation of 2-chloro-4-fluoro-5-hydrazinophenyl methanesulfonate

A mixture of 2-chloro-4-fluoro-5-aminophenyl methanesulfonate (24.0 g), 35% hydrochloric acid (63 g) and water (48 ml) was stirred at 60° C. for 30 minutes. Then, a solution of sodium nitrite (9.1 g) in water (55 ml) was added dropwise to the resulting mixture at −20° C. to effect diazotization reaction. The resulting mixture was added under stirring to a preformed and cooled (−20° C.) solution of 35% hydrochloric acid (52 ml) and stannous chloride hydrate (58 g) in water (100 ml) and the stirring was continued for 30 minutes under cooling. Then, the reaction solution was brought to room temperature and the pH of the solution was adjusted to 8.0 with an aqueous sodium hydroxide solution. Then, the reaction solution was extracted with toluene and tetrahydrofuran and the extract was washed with water, dried over anhydrous sodium sulfate and subjected to distillation under a reduced pressure to remove the solvent used, affording the titled compound (21.9 g) of the formula:

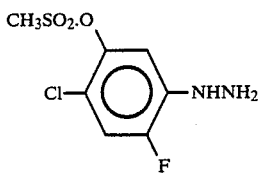

as yellow crystals. Recrystallization from cyclohexane gave pale yellow crystals having melting point 75°–77° C.

Examples 23 to 30 illustrate some embodiments for formulating compounds of the general formula (I) as the herbicidal compositions. Compounds Nos. correspond to those given in Table 1 above. Of course, this invention is not limited to these Examples but may include various modifications. Thus, the herbicidal compositions according to this invention may contain various other additives in any appropriate proportions and may comprise one or more further herbicidal compounds in any appropriate proportions. In the following Examples, all parts are by weight.

EXAMPLE 23

Preparation of Granules

Compound No. 20 (1 part), lauryl sulfate (1 part), calcium lignosulfonate (1 part), bentonite (30 parts) and clay (67 parts) were mixed together. Water (15 parts) was added to the mixture and the whole mixture was kneaded in a kneader, then granulated in a granulator and dried in a fluidized drier to obtain granules containing 1% of the active compound.

EXAMPLE 24

Preparation of Granules

According to the method same as that shown in Example 23, a granule preparation containing 1% of acitve ingredient was formulated from Compound No. 34 (1 part), lauryl sulfate (1 part), calcium lignosulfonate (1 part), bentonite (30 parts), clay (67 parts) and water (15 parts).

EXAMPLE 25

Preparation of Granules

The procedure of Example 23 was repeated except that Compound No. 47 was used in place of Compound No. 20, whereby to formulate a granule preparation containing 1% of the active compound.

EXAMPLE 26

Preparation of Wettable Powder

Compound No. 41 (15 parts), white carbon (15 parts), calcium lignosulfonate (3 parts), polyoxyethylene nonylphenol ether (2 parts), diatomaceous earth (5 parts) and clay (60 parts) were ground and homogeneously mixed together in a mill to obtain a wettable powder containing 15% of the active compound.

EXAMPLE 27

Preparation of Wettable Powder

The procedure of Example 26 was repeated except that Compound No. 138 was used in place of Compound No. 41, whereby to form a wettable powder containing 15% of the active compound.

EXAMPLE 28

Preparation of an Emulsifiable Concentrate

Compound No. 47 (20 parts), Sorpor 700 H (an emulsifier produced and sold by Toho Chemical Industry Company) (20 parts) and xylene (60 parts) were mixed together to obtain an emulsifiable concentrate containing 20% of the active compound.

EXAMPLE 29

Preparation of an Emulsifiable Concentrate

The procedure of Example 28 was repeated except that Compound No. 140 was used in place of Compound No. 47 to obtain an emulsifiable concentrate containing 20% of the active compound.

EXAMPLE 30

Preparation of a Dusting Powder

Compound No. 183 (0.5 parts), silicic acid anhydride in the form of fine powder (0.5 parts), calcium stearate (0.5 parts), clay (50 parts) and talc (48.5 parts) were ground and homogeneously mixed together to obtain a dusting powder containing 0.5% of the active compound.

The following Test Examples 1–4 were conducted to demonstrate the herbicidal activity of the new compounds according to this invention.

TEST EXAMPLE 1

This test was to evaluate the herbicidal effects of the compound under test on the weeds predominant in the irrigated field of aquatic rice plant, as well as the phytotoxicity of the compounds under test to aquatic rice plants a transplanted.

Each of biscuit pots having a top surface area of 1/5000 ares was packed with a farm soil (alluvial soil). In the surface layer of the soil in the pots were sown uniformly 50 seeds each of barnyard grass, bulrush, narrowleaf water-plantain, monochoria, false pimpernel and tooth cup. One day after the sowing, the pots were irrigated with water and the depth of the irrigating water on the soil surface in the pot was kept at 2 cm. Three days after the sowing, stocks each comprising two aquatic rice plants of 4-leaved stage were transplanted in each pot at the rate of three stocks of the rice plants per pot. One day after the transplantation of the rice plant, the emulsifiable concentrate as formulated according to the procedure of Example 28 above was diluted with water and the aqueous emulsion preparations so made was dropwise added to the irrigating water in the pot at the rate of application of 10 ml of said aqueous emulsion preparation (corresponding to the rate of 50 g of the active ingredient per 10 ares) for the pre-emergence herbicidal treatment. The test was conducted with two replicates. Thirty days after the treatment, the herbicidal activity of each compound under test as well as the phytotoxicity of the compound to aquatic rice plant were assessed according to the following gradings. The test results obtained are shown in Table 2 below.

| Gradings for evaluation of the herbicidal effects obtained | Rate (percentages) of kill of weeds |
|---|---|
| 5 | 100% |
| 4 | 80% to less than 100% |
| 3 | 60% to less than 80% |
| 2 | 40% to less than 60% |
| 1 | 20% to less than 40% |
| 0 | Less than 20% |

| Gradings for evaluation of the phytotoxicity to rice plant | Observed degrees of damage of rice plant |
|---|---|
| 5 | Complete kill |
| 4 | Great damage |
| 3 | Medium damage |
| 2 | Low damage |
| 1 | Very low damage |
| 0 | Substantially null |

TABLE 2

| Test Compound No. | Herbicidal Effect | | | | | | Phytotoxicity to aquatic rice plant |
|---|---|---|---|---|---|---|---|
| | Barnyard grass | Bulrush | Narrow-leaf water plantain | Monochoria | False pimpernel | Tooth cut | |
| 1 | 5 | 4 | 5 | 5 | 5 | 5 | 0 |
| 2 | 5 | 4 | 5 | 5 | 5 | 5 | 0 |
| 3 | 4 | 4 | 5 | 4 | 5 | 5 | 0 |
| 4 | 4 | 4 | 4 | 4 | 5 | 5 | 0 |
| 5 | 5 | 4 | 5 | 5 | 5 | 5 | 0 |
| 6 | 5 | 5 | 5 | 5 | 5 | 5 | 0 |
| 7 | 4 | 4 | 5 | 5 | 5 | 5 | 0 |
| 8 | 4 | 5 | 5 | 5 | 5 | 5 | 0 |
| 9 | 4 | 4 | 5 | 4 | 5 | 5 | 0 |
| 10 | 5 | 4 | 5 | 5 | 5 | 5 | 0 |
| 11 | 5 | 4 | 5 | 4 | 5 | 5 | 0 |
| 12 | 4 | 4 | 5 | 5 | 5 | 5 | 0 |
| 13 | 4 | 4 | 4 | 4 | 5 | 5 | 0 |
| 14 | 5 | 4 | 5 | 5 | 5 | 5 | 0 |
| 15 | 5 | 5 | 5 | 4 | 5 | 5 | 0 |
| 16 | 5 | 5 | 5 | 4 | 5 | 5 | 0 |
| 17 | 5 | 5 | 5 | 5 | 5 | 5 | 0 |
| 18 | 4 | 4 | 5 | 4 | 5 | 5 | 0 |
| 19 | 5 | 5 | 5 | 5 | 5 | 5 | 0 |
| 20 | 5 | 5 | 5 | 5 | 5 | 5 | 0 |
| 21 | 5 | 5 | 5 | 5 | 5 | 5 | 0 |
| 22 | 4 | 4 | 5 | 4 | 5 | 5 | 0 |
| 23 | 5 | 4 | 5 | 5 | 5 | 5 | 0 |
| 24 | 4 | 4 | 5 | 5 | 5 | 5 | 0 |
| 25 | 5 | 4 | 5 | 5 | 5 | 5 | 0 |
| 26 | 4 | 4 | 4 | 5 | 5 | 5 | 0 |
| 27 | 5 | 5 | 5 | 5 | 5 | 5 | 0 |
| 28 | 4 | 4 | 5 | 4 | 5 | 4 | 0 |
| 29 | 4 | 4 | 5 | 5 | 4 | 5 | 0 |
| 30 | 5 | 4 | 5 | 5 | 5 | 5 | 0 |
| 31 | 4 | 4 | 4 | 4 | 5 | 5 | 0 |
| 32 | 4 | 4 | 4 | 4 | 5 | 4 | 0 |
| 33 | 5 | 5 | 5 | 5 | 5 | 5 | 0 |
| 34 | 5 | 5 | 5 | 5 | 5 | 5 | 0 |
| 35 | 5 | 5 | 5 | 5 | 5 | 5 | 0 |
| 36 | 4 | 4 | 4 | 4 | 5 | 5 | 0 |
| 37 | 5 | 4 | 5 | 5 | 5 | 5 | 0 |
| 38 | 5 | 5 | 5 | 5 | 5 | 5 | 0 |
| 39 | 5 | 5 | 5 | 5 | 5 | 5 | 0 |
| 40 | 5 | 5 | 5 | 5 | 5 | 5 | 0 |
| 41 | 5 | 5 | 5 | 5 | 5 | 5 | 0 |
| 42 | 5 | 4 | 5 | 5 | 5 | 5 | 0 |
| 43 | 5 | 5 | 5 | 5 | 5 | 5 | 0 |
| 44 | 5 | 4 | 5 | 5 | 5 | 5 | 0 |
| 45 | 5 | 5 | 5 | 5 | 5 | 5 | 0 |
| 46 | 5 | 5 | 5 | 5 | 5 | 5 | 0 |
| 47 | 5 | 5 | 5 | 5 | 5 | 5 | 0 |
| 48 | 5 | 5 | 5 | 5 | 5 | 5 | 0 |
| 49 | 5 | 4 | 5 | 5 | 5 | 5 | 0 |
| 50 | 4 | 4 | 5 | 5 | 5 | 5 | 0 |
| 51 | 4 | 4 | 4 | 5 | 5 | 5 | 0 |
| 52 | 5 | 5 | 5 | 5 | 5 | 5 | 0 |
| 53 | 4 | 4 | 4 | 4 | 5 | 5 | 0 |
| 54 | 5 | 4 | 4 | 5 | 5 | 5 | 0 |
| 55 | 5 | 5 | 4 | 4 | 5 | 5 | 0 |
| 56 | 5 | 4 | 5 | 5 | 5 | 5 | 0 |
| 57 | 5 | 5 | 5 | 5 | 5 | 5 | 0 |
| 58 | 4 | 4 | 4 | 5 | 4 | 5 | 0 |
| 59 | 4 | 4 | 4 | 5 | 4 | 5 | 0 |
| 60 | 5 | 4 | 5 | 4 | 5 | 5 | 0 |

TABLE 2-continued

| | Herbicidal Effect | | | | | | Phytotoxicity to aquatic rice plant |
|---|---|---|---|---|---|---|---|
| | Barnyard grass | Bulrush | Narrow-leaf water plantain | Monochoria | False pimpernel | Tooth cut | |
| 61 | 5 | 4 | 4 | 4 | 5 | 5 | 0 |
| 62 | 4 | 4 | 4 | 5 | 5 | 5 | 0 |
| 63 | 5 | 4 | 4 | 4 | 5 | 4 | 0 |
| 64 | 5 | 4 | 5 | 5 | 5 | 5 | 0 |
| 65 | 5 | 5 | 5 | 5 | 5 | 5 | 0 |
| 66 | 5 | 4 | 5 | 5 | 5 | 5 | 0 |
| 67 | 5 | 4 | 4 | 5 | 5 | 5 | 0 |
| 68 | 4 | 4 | 4 | 5 | 4 | 5 | 0 |
| 69 | 4 | 4 | 4 | 4 | 4 | 5 | 0 |
| 70 | 5 | 5 | 5 | 5 | 5 | 5 | 0 |
| 71 | 5 | 4 | 4 | 4 | 5 | 5 | 0 |
| 72 | 4 | 4 | 4 | 4 | 5 | 4 | 0 |
| 73 | 5 | 4 | 5 | 5 | 4 | 5 | 0 |
| 74 | 5 | 4 | 5 | 5 | 5 | 5 | 0 |
| 75 | 5 | 4 | 4 | 4 | 5 | 5 | 0 |
| 76 | 4 | 4 | 4 | 5 | 5 | 5 | 0 |
| 77 | 5 | 5 | 5 | 5 | 5 | 5 | 0 |
| 78 | 5 | 4 | 5 | 5 | 5 | 5 | 0 |
| 79 | 5 | 5 | 5 | 5 | 5 | 5 | 0 |
| 80 | 5 | 5 | 5 | 5 | 5 | 5 | 0 |
| 81 | 5 | 4 | 5 | 5 | 5 | 5 | 0 |
| 82 | 5 | 4 | 5 | 5 | 5 | 5 | 0 |
| 83 | 5 | 5 | 5 | 5 | 5 | 5 | 0 |
| 84 | 4 | 5 | 4 | 4 | 5 | 5 | 0 |
| 85 | 4 | 4 | 4 | 4 | 5 | 5 | 0 |
| 86 | 5 | 4 | 5 | 5 | 5 | 5 | 0 |
| 87 | 5 | 4 | 5 | 5 | 5 | 5 | 0 |
| 88 | 4 | 4 | 4 | 4 | 5 | 5 | 0 |
| 89 | 5 | 5 | 5 | 5 | 5 | 5 | 0 |
| 90 | 5 | 4 | 5 | 5 | 5 | 5 | 0 |
| 91 | 5 | 4 | 4 | 5 | 5 | 5 | 0 |
| 92 | 4 | 4 | 4 | 4 | 4 | 5 | 0 |
| 93 | 5 | 4 | 5 | 5 | 5 | 5 | 0 |
| 94 | 4 | 4 | 4 | 5 | 5 | 5 | 0 |
| 95 | 4 | 4 | 4 | 5 | 5 | 5 | 0 |
| 96 | 5 | 4 | 5 | 5 | 5 | 5 | 0 |
| 97 | 4 | 4 | 5 | 5 | 5 | 4 | 0 |
| 98 | 4 | 4 | 5 | 5 | 4 | 5 | 0 |
| 99 | 4 | 5 | 4 | 5 | 5 | 5 | 0 |
| 100 | 4 | 4 | 4 | 5 | 5 | 5 | 0 |
| 101 | 5 | 4 | 5 | 5 | 5 | 5 | 0 |
| 102 | 5 | 4 | 5 | 5 | 5 | 5 | 0 |
| 103 | 4 | 5 | 4 | 4 | 5 | 5 | 0 |
| 104 | 5 | 4 | 5 | 5 | 5 | 5 | 0 |
| 105 | 5 | 5 | 4 | 5 | 5 | 5 | 0 |
| 106 | 5 | 5 | 4 | 5 | 5 | 5 | 0 |
| 107 | 4 | 4 | 5 | 4 | 5 | 5 | 0 |
| 108 | 5 | 4 | 5 | 5 | 5 | 5 | 0 |
| 109 | 4 | 4 | 4 | 5 | 5 | 5 | 0 |
| 110 | 5 | 4 | 5 | 5 | 5 | 5 | 0 |
| 111 | 4 | 4 | 4 | 5 | 5 | 5 | 0 |
| 112 | 4 | 4 | 5 | 5 | 5 | 5 | 0 |
| 113 | 4 | 5 | 4 | 5 | 5 | 5 | 0 |
| 114 | 4 | 4 | 4 | 5 | 5 | 5 | 0 |
| 115 | 5 | 4 | 5 | 5 | 5 | 5 | 0 |
| 116 | 4 | 4 | 4 | 4 | 5 | 5 | 0 |
| 117 | 4 | 5 | 4 | 4 | 5 | 5 | 0 |
| 118 | 4 | 4 | 5 | 4 | 5 | 5 | 0 |
| 119 | 4 | 4 | 5 | 4 | 4 | 5 | 0 |
| 120 | 4 | 5 | 5 | 5 | 5 | 5 | 0 |
| 121 | 4 | 4 | 4 | 4 | 5 | 5 | 0 |
| 122 | 5 | 5 | 4 | 5 | 5 | 5 | 0 |
| 123 | 4 | 5 | 4 | 5 | 5 | 5 | 0 |
| 124 | 5 | 5 | 5 | 5 | 5 | 5 | 0 |
| 125 | 5 | 4 | 5 | 5 | 5 | 5 | 0 |
| 126 | 5 | 5 | 5 | 5 | 5 | 5 | 0 |
| 127 | 5 | 4 | 5 | 5 | 5 | 5 | 0 |
| 128 | 5 | 5 | 5 | 5 | 5 | 5 | 0 |
| 129 | 5 | 5 | 5 | 5 | 5 | 5 | 0 |
| 130 | 5 | 4 | 5 | 5 | 5 | 5 | 0 |
| 131 | 4 | 5 | 5 | 5 | 5 | 5 | 0 |
| 132 | 5 | 5 | 5 | 5 | 5 | 5 | 0 |
| 133 | 5 | 4 | 5 | 5 | 5 | 5 | 0 |
| 134 | 4 | 5 | 5 | 5 | 5 | 5 | 0 |
| 135 | 4 | 5 | 5 | 5 | 5 | 5 | 0 |
| 136 | 5 | 5 | 5 | 5 | 5 | 5 | 0 |
| 137 | 5 | 4 | 5 | 5 | 5 | 5 | 0 |
| 138 | 5 | 5 | 5 | 5 | 5 | 5 | 0 |
| 139 | 4 | 5 | 5 | 5 | 5 | 5 | 0 |

TABLE 2-continued

| | Herbicidal Effect | | | | | | Phytotoxicity to aquatic rice plant |
|---|---|---|---|---|---|---|---|
| | Barnyard grass | Bulrush | Narrow-leaf water plantain | Monochoria | False pimpernel | Tooth cut | |
| 140 | 5 | 5 | 5 | 5 | 5 | 5 | 0 |
| 141 | 5 | 5 | 5 | 5 | 5 | 5 | 0 |
| 142 | 4 | 4 | 5 | 5 | 5 | 5 | 0 |
| 143 | 4 | 5 | 5 | 5 | 5 | 5 | 0 |
| 144 | 4 | 4 | 4 | 4 | 5 | 5 | 0 |
| 145 | 4 | 5 | 4 | 5 | 5 | 5 | 0 |
| 146 | 4 | 4 | 4 | 5 | 4 | 5 | 0 |
| 147 | 5 | 5 | 5 | 5 | 5 | 5 | 0 |
| 148 | 5 | 5 | 5 | 5 | 5 | 5 | 0 |
| 149 | 4 | 4 | 5 | 4 | 5 | 4 | 0 |
| 150 | 4 | 4 | 4 | 5 | 4 | 5 | 0 |
| 151 | 5 | 4 | 5 | 5 | 5 | 5 | 0 |
| 152 | 5 | 5 | 5 | 5 | 5 | 5 | 0 |
| 153 | 4 | 4 | 5 | 5 | 5 | 5 | 0 |
| 154 | 5 | 4 | 5 | 5 | 5 | 5 | 0 |
| 155 | 4 | 4 | 5 | 5 | 5 | 5 | 0 |
| 156 | 5 | 4 | 5 | 5 | 5 | 5 | 0 |
| 157 | 4 | 4 | 5 | 5 | 5 | 5 | 0 |
| 158 | 4 | 5 | 5 | 5 | 5 | 5 | 0 |
| 159 | 4 | 5 | 5 | 5 | 5 | 5 | 0 |
| 160 | 5 | 4 | 4 | 5 | 5 | 5 | 0 |
| 161 | 5 | 4 | 4 | 5 | 5 | 5 | 0 |
| 162 | 5 | 4 | 5 | 5 | 5 | 5 | 0 |
| 163 | 5 | 5 | 5 | 5 | 5 | 5 | 0 |
| 164 | 4 | 5 | 4 | 4 | 5 | 5 | 0 |
| 165 | 4 | 4 | 5 | 4 | 5 | 5 | 0 |
| 166 | 5 | 4 | 5 | 5 | 5 | 5 | 0 |
| 167 | 5 | 5 | 5 | 5 | 5 | 5 | 0 |
| 168 | 4 | 4 | 5 | 5 | 5 | 5 | 0 |
| 169 | 4 | 4 | 4 | 5 | 5 | 5 | 0 |
| 170 | 4 | 5 | 4 | 5 | 5 | 5 | 0 |
| 171 | 5 | 4 | 5 | 5 | 5 | 5 | 0 |
| 172 | 4 | 4 | 5 | 5 | 5 | 5 | 0 |
| 173 | 4 | 4 | 5 | 5 | 5 | 5 | 0 |
| 174 | 5 | 4 | 5 | 5 | 5 | 5 | 0 |
| 175 | 5 | 4 | 5 | 5 | 5 | 5 | 0 |
| 176 | 5 | 5 | 5 | 5 | 5 | 5 | 0 |
| 177 | 4 | 5 | 5 | 5 | 5 | 5 | 0 |
| 178 | 5 | 5 | 5 | 5 | 5 | 5 | 0 |
| 179 | 5 | 5 | 5 | 5 | 5 | 5 | 0 |
| 180 | 4 | 4 | 4 | 4 | 5 | 5 | 0 |
| 181 | 4 | 5 | 5 | 5 | 5 | 5 | 0 |
| 182 | 5 | 5 | 5 | 5 | 5 | 5 | 0 |
| 183 | 5 | 5 | 5 | 5 | 5 | 5 | 0 |
| 184 | 5 | 5 | 5 | 5 | 5 | 5 | 0 |
| 185 | 5 | 5 | 5 | 5 | 5 | 5 | 0 |
| 186 | 4 | 4 | 5 | 5 | 5 | 5 | 0 |
| 187 | 4 | 5 | 5 | 5 | 5 | 5 | 0 |
| 188 | 4 | 4 | 4 | 5 | 5 | 5 | 0 |
| 189 | 4 | 5 | 5 | 5 | 5 | 5 | 0 |
| 190 | 4 | 4 | 4 | 5 | 5 | 5 | 0 |
| 191 | 4 | 4 | 4 | 4 | 5 | 5 | 0 |
| 192 | 4 | 4 | 5 | 4 | 5 | 5 | 0 |
| 193 | 4 | 4 | 5 | 5 | 5 | 5 | 0 |
| 194 | 4 | 4 | 5 | 5 | 5 | 5 | 0 |
| 195 | 4 | 5 | 5 | 5 | 5 | 5 | 0 |
| 196 | 4 | 4 | 4 | 5 | 5 | 5 | 0 |
| 197 | 5 | 5 | 5 | 5 | 5 | 5 | 0 |
| 198 | 4 | 4 | 5 | 5 | 5 | 5 | 0 |
| 199 | 4 | 5 | 5 | 5 | 5 | 5 | 0 |
| 200 | 4 | 4 | 4 | 4 | 4 | 5 | 0 |
| 201 | 4 | 5 | 4 | 5 | 5 | 5 | 0 |
| 202 | 4 | 4 | 4 | 5 | 5 | 5 | 0 |
| 203 | 5 | 5 | 5 | 5 | 5 | 5 | 0 |
| 204 | 4 | 5 | 4 | 5 | 5 | 5 | 0 |
| 205 | 5 | 5 | 5 | 5 | 5 | 5 | 0 |
| 206 | 4 | 4 | 5 | 4 | 4 | 4 | 0 |
| 207 | 4 | 5 | 5 | 5 | 5 | 5 | 0 |
| 208 | 4 | 4 | 5 | 5 | 5 | 5 | 0 |
| 209 | 4 | 5 | 4 | 5 | 5 | 5 | 0 |
| Comparative Compound | | | | | | | |
| A | 1 | 0 | 1 | 2 | 3 | 2 | 0 |
| B | 2 | 1 | 2 | 3 | 3 | 3 | 1 |
| C | 0 | 0 | 0 | 1 | 0 | 0 | 0 |
| D | 0 | 0 | 0 | 1 | 1 | 0 | 0 |

TABLE 2-continued

| | Herbicidal Effect | | | | | | Phytotoxicity to aquatic rice plant |
|---|---|---|---|---|---|---|---|
| | Barnyard grass | Bulrush | Narrow-leaf water plantain | Monochoria | False pimpernel | Tooth cut | |
| E | 3 | 0 | 3 | 2 | 3 | 3 | 1 |

Notes:-
In Table 2 above; Comparative compound A:

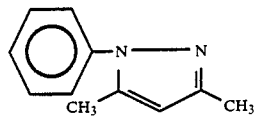

(a compound as disclosed in Japanese patent publication No. 19958/65).
Comparative compound B:

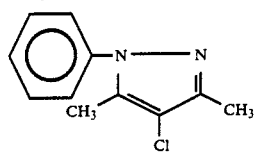

(a compound as disclosed in Japanese patent publication No. 19958/65).
Comparative compound C:

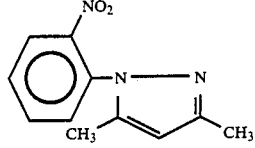

(a compound as disclosed in Japanese patent publication No. 14833/67).
Comparative compound D:

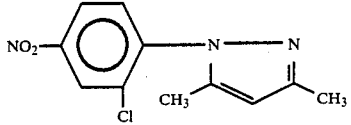

(a compound as disclosed in Japanese patent publication No. 14833/67).
Comparative compound E:

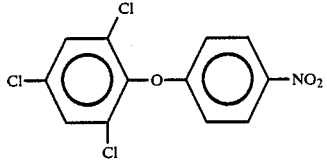

("Chlornitrophene", commercially available herbicide).

TEST EXAMPLE 2

This test was to evaluate the herbicidal effects of the compounds under test on the weeds predominant in the irrigated field of aquatic rice plant, as well as the phytotoxicity of the compounds under test to the aquatic rice plant when the compounds were applied at low rates of application of 25, 12.5 or 6.25 g of the active ingredient per 10 ares.

The procedure of Test Example 1 above was repeated, except that the herbicidal treatment of the weeds was conducted by applying the test compounds at low rates. The herbicidal effects on the weeds and the phytotoxicity to aquatic rice plant were assessed in the same way as in Test Example 1 above. The test results obtained are summarized in Table 3 below.

TABLE 3

| Test compound No. | Rate of application of active compound (g/10 ares) | Herbicidal Effect | | | | | | Phyto-toxicity to aquatic rice plant |
|---|---|---|---|---|---|---|---|---|
| | | Barn-yard grass | Bulrush | Narrow-leaf water plantain | Mono-choria | False pimpernel | Tooth cup | |
| 6 | 25 | 5 | 5 | 5 | 5 | 5 | 5 | 0 |
| | 12.5 | 5 | 4 | 5 | 5 | 5 | 5 | 0 |
| | 6.25 | 4 | 4 | 4 | 5 | 5 | 5 | 0 |
| 17 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 4 | 5 | 5 | 0 |
| 19 | 25 | 5 | 5 | 5 | 5 | 5 | 5 | 0 |
| | 12.5 | 5 | 5 | 5 | 5 | 5 | 5 | 0 |
| | 6.25 | 5 | 4 | 5 | 5 | 5 | 5 | 0 |
| 20 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 5 | 5 | 5 | 0 |

TABLE 3-continued

| Test compound No. | Rate of application of active compound (g/10 ares) | Herbicidal Effect ||||||  Phyto-toxicity to aquatic rice plant |
|---|---|---|---|---|---|---|---|---|
| | | Barn-yard grass | Bulrush | Narrow-leaf water plantain | Mono-choria | False pimpernel | Tooth cup | |
| 21 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 27 | 25 | 5 | 5 | 5 | 5 | 5 | 5 | 0 |
| | 12.5 | 5 | 4 | 5 | 5 | 5 | 5 | 0 |
| | 6.25 | 4 | 4 | 4 | 5 | 5 | 5 | 0 |
| 33 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 34 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 35 | 25 | 5 | 5 | 5 | 5 | 5 | 5 | 0 |
| | 12.5 | 5 | 5 | 5 | 5 | 5 | 5 | 0 |
| | 6.25 | 5 | 4 | 5 | 5 | 5 | 5 | 0 |
| 38 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 39 | 25 | 5 | 5 | 5 | 5 | 5 | 5 | 0 |
| | 12.5 | 5 | 5 | 5 | 5 | 5 | 5 | 0 |
| | 6.25 | 5 | 4 | 5 | 5 | 5 | 5 | 0 |
| 40 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 5 | 5 | 5 | 0 |
| 41 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 43 | 25 | 5 | 5 | 5 | 5 | 5 | 5 | 0 |
| | 12.5 | 5 | 4 | 5 | 5 | 5 | 5 | 0 |
| | 6.25 | 4 | 4 | 4 | 5 | 5 | 5 | 0 |
| 45 | 25 | 5 | 5 | 5 | 5 | 5 | 5 | 0 |
| | 12.5 | 4 | 4 | 5 | 5 | 5 | 5 | 0 |
| | 6.25 | 4 | 4 | 4 | 4 | 4 | 5 | 0 |
| 46 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 47 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 48 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 52 | 25 | 5 | 5 | 5 | 5 | 5 | 5 | 0 |
| | 12.5 | 5 | 4 | 5 | 5 | 5 | 5 | 0 |
| | 6.25 | 4 | 4 | 4 | 4 | 5 | 5 | 0 |
| 57 | 25 | 5 | 5 | 5 | 5 | 5 | 5 | 0 |
| | 12.5 | 5 | 5 | 5 | 5 | 5 | 5 | 0 |
| | 6.25 | 5 | 4 | 5 | 5 | 5 | 5 | 0 |
| 65 | 25 | 5 | 5 | 5 | 5 | 5 | 5 | 0 |
| | 12.5 | 5 | 5 | 5 | 5 | 5 | 5 | 0 |
| | 6.25 | 5 | 4 | 4 | 5 | 5 | 5 | 0 |
| 70 | 25 | 5 | 5 | 5 | 5 | 5 | 5 | 0 |
| | 12.5 | 5 | 4 | 5 | 5 | 5 | 5 | 0 |
| | 6.25 | 4 | 4 | 5 | 5 | 5 | 5 | 0 |
| 77 | 25 | 5 | 5 | 5 | 5 | 5 | 5 | 0 |
| | 12.5 | 5 | 5 | 5 | 5 | 5 | 5 | 0 |
| | 6.25 | 4 | 4 | 4 | 4 | 5 | 5 | 0 |
| 79 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 80 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 83 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 4 | 5 | 5 | 0 |
| 89 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 124 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 5 | 5 | 5 | 0 |
| 126 | 25 | 5 | 5 | 5 | 5 | 5 | 5 | 0 |
| | 12.5 | 5 | 5 | 5 | 5 | 5 | 5 | 0 |
| | 6.25 | 4 | 5 | 5 | 5 | 5 | 5 | 0 |
| 128 | 25 | 5 | 5 | 5 | 5 | 5 | 5 | 0 |
| | 12.5 | 5 | 5 | 5 | 5 | 5 | 5 | 0 |

TABLE 3-continued

| Test compound No. | Rate of application of active compound (g/10 ares) | Herbicidal Effect | | | | | | Phyto-toxicity to aquatic rice plant |
|---|---|---|---|---|---|---|---|---|
| | | Barn-yard grass | Bulrush | Narrow-leaf water plantain | Mono-choria | False pimpernel | Tooth cup | |
| | 6.25 | 5 | 5 | 5 | 5 | 5 | 5 | 0 |
| 129 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 132 | 25 | 5 | 5 | 5 | 5 | 5 | 5 | 0 |
| | 12.5 | 4 | 5 | 5 | 5 | 5 | 5 | 0 |
| | 6.25 | 4 | 4 | 4 | 5 | 5 | 5 | 0 |
| 136 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 138 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 140 | 25 | 5 | 5 | 5 | 5 | 5 | 5 | 0 |
| | 12.5 | 5 | 4 | 4 | 5 | 5 | 5 | 0 |
| | 6.25 | 4 | 4 | 4 | 4 | 4 | 5 | 0 |
| 141 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 147 | 25 | 5 | 5 | 5 | 5 | 5 | 5 | 0 |
| | 12.5 | 4 | 5 | 5 | 5 | 5 | 5 | 0 |
| | 6.25 | 4 | 4 | 4 | 5 | 5 | 5 | 0 |
| 148 | 25 | 5 | 5 | 5 | 5 | 5 | 5 | 0 |
| | 12.5 | 5 | 4 | 4 | 5 | 5 | 5 | 0 |
| | 6.25 | 4 | 4 | 4 | 4 | 5 | 5 | 0 |
| 152 | 25 | 5 | 5 | 5 | 5 | 5 | 5 | 0 |
| | 12.5 | 5 | 5 | 5 | 5 | 5 | 5 | 0 |
| | 6.25 | 4 | 4 | 4 | 4 | 4 | 5 | 0 |
| 163 | 25 | 5 | 5 | 5 | 5 | 5 | 5 | 0 |
| | 12.5 | 5 | 5 | 5 | 5 | 5 | 5 | 0 |
| | 6.25 | 5 | 4 | 5 | 5 | 5 | 5 | 0 |
| 167 | 25 | 5 | 5 | 5 | 5 | 5 | 5 | 0 |
| | 12.5 | 4 | 4 | 5 | 5 | 5 | 5 | 0 |
| | 6.25 | 4 | 4 | 4 | 4 | 5 | 5 | 0 |
| 176 | 25 | 5 | 5 | 5 | 5 | 5 | 5 | 0 |
| | 12.5 | 5 | 5 | 5 | 5 | 5 | 5 | 0 |
| | 6.25 | 4 | 5 | 5 | 5 | 5 | 5 | 0 |
| 178 | 25 | 5 | 5 | 5 | 5 | 5 | 5 | 0 |
| | 12.5 | 5 | 5 | 5 | 5 | 5 | 5 | 0 |
| | 6.25 | 4 | 4 | 5 | 5 | 5 | 5 | 0 |
| 179 | 25 | 5 | 5 | 5 | 5 | 5 | 5 | 0 |
| | 12.5 | 4 | 5 | 5 | 5 | 5 | 5 | 0 |
| | 6.25 | 4 | 4 | 4 | 5 | 5 | 4 | 0 |
| 182 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 183 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 184 | 25 | 5 | 5 | 5 | 5 | 5 | 5 | 0 |
| | 12.5 | 5 | 4 | 5 | 5 | 5 | 5 | 0 |
| | 6.25 | 4 | 4 | 4 | 5 | 5 | 5 | 0 |
| 185 | 25 | 5 | 5 | 5 | 5 | 5 | 5 | 0 |
| | 12.5 | 5 | 4 | 5 | 5 | 5 | 5 | 0 |
| | 6.25 | 4 | 4 | 5 | 5 | 5 | 5 | 0 |
| 197 | 25 | 5 | 5 | 5 | 5 | 5 | 5 | 0 |
| | 12.5 | 5 | 5 | 5 | 5 | 5 | 5 | 0 |
| | 6.25 | 4 | 5 | 5 | 5 | 5 | 5 | 0 |
| 203 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| 205 | 25 | 5 | 5 | 5 | 5 | 5 | 5 | 0 |
| | 12.5 | 5 | 5 | 5 | 5 | 5 | 5 | 0 |
| | 6.25 | 5 | 5 | 5 | 5 | 5 | 5 | 0 |
| Comparative compound A | 25 | 0 | 0 | 0 | 1 | 2 | 1 | 0 |
| | 12.5 | 0 | 0 | 0 | 0 | 1 | 0 | 0 |
| | 6.25 | 0 | 0 | 0 | 0 | 0 | 0 | 0 |
| Comparative compound B | 25 | 1 | 1 | 1 | 2 | 2 | 2 | 0 |
| | 12.5 | 0 | 0 | 1 | 1 | 2 | 1 | 0 |
| | 6.25 | 0 | 0 | 0 | 0 | 0 | 0 | 0 |
| Comparative compound C | 25 | 0 | 0 | 0 | 0 | 0 | 0 | 0 |
| | 12.5 | 0 | 0 | 0 | 0 | 0 | 0 | 0 |
| | 6.25 | 0 | 0 | 0 | 0 | 0 | 0 | 0 |
| Comparative compound D | 25 | 0 | 0 | 0 | 0 | 0 | 0 | 0 |
| | 12.5 | 0 | 0 | 0 | 0 | 0 | 0 | 0 |
| | 6.25 | 0 | 0 | 0 | 0 | 0 | 0 | 0 |
| Comparative | 25 | 2 | 0 | 2 | 1 | 2 | 2 | 0 |

TABLE 3-continued

| Test compound No. | Rate of application of active compound (g/10 ares) | Herbicidal Effect | | | | | | Phyto-toxicity to aquatic rice plant |
|---|---|---|---|---|---|---|---|---|
| | | Barn-yard grass | Bulrush | Narrow-leaf water plantain | Mono-choria | False pimpernel | Tooth cup | |
| compound E | 12.5 | 1 | 0 | 2 | 1 | 1 | 1 | 0 |
| | 6.25 | 0 | 0 | 0 | 0 | 0 | 0 | 0 |

Notes:
In Table 3 above, Comparative Compound A to E were the same compounds as identified for Table 2 above.

TEST EXAMPLE 3

This test was to evaluate the herbicidal activity of the compounds under test on the weeds predominant in the non-irrigated farm field of various crop plants, as well as the phytotoxicity of the compounds to crop plants.

The test of evaluating the herbicidal effects of the test compounds on the weeds was conducted according to the following procedure. Thus, each of biscuit pots having a top surface area of 1/5000 ares was packed with a farm soil (alluvial soil). Seeds of crabgrass, common lambsquarters, pigweed and smartweed were sown by mixing 50 seeds of each sort of weed uniformly with the soil present in the 1 cm deep surface layer of the soil in each pot and then lightly pressing on the top surface of the soil in the pot. Two days after the sowing, the top surface of the soil in the pots was herbicidally treated by spraying thereon such an aqueous emulsion preparation containing the compound under test which had been prepared by diluting with water the emulsifiable concentrate as formulated by the procedure of Example 28 above, at a rate of application of 100 l per 10 ares of the field (corresponding to the rate of application of 100 g of the active ingredient per 10 ares). The test was conducted with two replicates. Thirty days after the sowing, the herbicidal effects were assessed with the same gradings and in the same way as described in Tast Example 1 above.

The test of evaluating the phytotoxicity to crop plants was performed according to the following procedure. Thus, each of buiscuit pots having a top surface area of 1/10,000 ares was packed with a farm soil (alluyial soil). Seeds of various crop plants, namely 5 seeds of soy bean, 10 seeds of sugar beet, 10 seeds of radish, 10 seeds of wheat or 5 seeds of maize were sown on the soil surface in the separate pots, followed by lightly pressing on the top surface of the soil. One day after the sowing, the soil surface was treated by spraying thereon an aqueous emulsion preparation containing the test compound which had been prepared by diluting with water the emulsifiable concentrate as made in Example 28 above, at a rate of application of 100 l of the emulsion preparation per 10 ares of the field (corresponding to the rate of application of 100 g of the active ingredient per 10 ares). The test was conducted with two duplicates. Thirty days after the treatment with the test compounds, the phytotoxicity of the tested compounds to germinated crop plants was assesssed in the same way and with the same gradings as set out in Test Example 1 above. The results obtained are summarized in Table 4 below.

TABLE 4

| | Herbicidal effect on weeds in farm-field | | | | Phyto-toxicity to crop plants | | | | |
|---|---|---|---|---|---|---|---|---|---|
| | Crabgrass | Common lambsquarters | Pigweed | Smartweed | Soya bean | Sugar beet | Radish | Wheat | Maize |
| Test Compound No. | | | | | | | | | |
| 1 | 5 | 5 | 4 | 4 | 0 | 0 | 0 | 0 | 0 |
| 2 | 5 | 5 | 4 | 4 | 0 | 0 | 0 | 0 | 0 |
| 3 | 4 | 5 | 4 | 4 | 0 | 0 | 0 | 0 | 0 |
| 4 | 4 | 4 | 4 | 4 | 0 | 0 | 0 | 0 | 0 |
| 5 | 5 | 5 | 5 | 5 | 0 | 0 | 0 | 0 | 0 |
| 6 | 5 | 5 | 5 | 4 | 0 | 0 | 0 | 0 | 0 |
| 7 | 4 | 5 | 4 | 4 | 0 | 0 | 0 | 0 | 0 |
| 8 | 5 | 5 | 4 | 4 | 0 | 0 | 0 | 0 | 0 |
| 9 | 4 | 5 | 4 | 4 | 0 | 0 | 0 | 0 | 0 |
| 10 | 5 | 5 | 5 | 4 | 0 | 0 | 0 | O | 0 |
| 11 | 5 | 5 | 4 | 5 | 0 | 0 | 0 | 0 | 0 |
| 12 | 5 | 5 | 4 | 5 | 0 | 0 | 0 | 0 | 0 |
| 13 | 4 | 4 | 5 | 4 | 0 | 0 | 0 | 0 | 0 |
| 14 | 4 | 4 | 4 | 4 | 0 | 0 | 0 | 0 | 0 |
| 15 | 5 | 5 | 5 | 5 | 0 | 0 | 0 | 0 | 0 |
| 16 | 5 | 5 | 5 | 4 | 0 | 0 | 0 | 0 | 0 |
| 17 | 5 | 5 | 5 | 5 | 0 | 0 | 0 | 0 | 0 |
| 18 | 4 | 5 | 4 | 4 | 0 | 0 | 0 | 0 | 0 |
| 19 | 5 | 5 | 5 | 4 | 0 | 0 | 0 | 0 | 0 |
| 20 | 5 | 5 | 5 | 4 | 0 | 0 | 0 | 0 | 0 |
| 21 | 5 | 5 | 5 | 5 | 0 | 0 | 0 | 0 | 0 |
| 22 | 5 | 4 | 4 | 4 | 0 | 0 | 0 | 0 | 0 |
| 23 | 5 | 4 | 4 | 4 | 0 | 0 | 0 | 0 | 0 |
| 24 | 4 | 5 | 4 | 4 | 0 | 0 | 0 | 0 | 0 |
| 25 | 4 | 4 | 4 | 4 | 0 | 0 | 0 | 0 | 0 |
| 26 | 4 | 4 | 4 | 4 | 0 | 0 | 0 | 0 | 0 |
| 27 | 5 | 5 | 5 | 5 | 0 | 0 | 0 | 0 | 0 |
| 28 | 5 | 4 | 4 | 4 | 0 | 0 | 0 | 0 | 0 |
| 29 | 4 | 5 | 4 | 4 | 0 | 0 | 0 | 0 | 0 |
| 30 | 5 | 5 | 5 | 4 | 0 | 0 | 0 | 0 | 0 |
| 31 | 4 | 5 | 4 | 4 | 0 | 0 | 0 | 0 | 0 |
| 32 | 4 | 4 | 4 | 4 | 0 | 0 | 0 | 0 | 0 |
| 33 | 5 | 5 | 5 | 5 | 0 | 0 | 0 | 0 | 0 |

TABLE 4-continued

| | Herbicidal effect on weeds in farm-field | | | | Phyto-toxicity to crop plants | | | | |
| --- | --- | --- | --- | --- | --- | --- | --- | --- | --- |
| | Crabgrass | Common lambsquarters | Pigweed | Smartweed | Soya bean | Sugar beet | Radish | Wheat | Maize |
| 34 | 5 | 5 | 5 | 5 | 0 | 0 | 0 | 0 | 0 |
| 35 | 4 | 5 | 4 | 4 | 0 | 0 | 0 | 0 | 0 |
| 36 | 5 | 5 | 5 | 5 | 0 | 0 | 0 | 0 | 0 |
| 37 | 5 | 5 | 5 | 5 | 0 | 0 | 0 | 0 | 0 |
| 38 | 5 | 5 | 5 | 5 | 0 | 0 | 0 | 0 | 0 |
| 39 | 5 | 5 | 5 | 4 | 0 | 0 | 0 | 0 | 0 |
| 40 | 5 | 5 | 5 | 4 | 0 | 0 | 0 | 0 | 0 |
| 41 | 5 | 5 | 5 | 5 | 0 | 0 | 0 | 0 | 0 |
| 42 | 5 | 5 | 5 | 4 | 0 | 0 | 0 | 0 | 0 |
| 43 | 5 | 5 | 5 | 4 | 0 | 0 | 0 | 0 | 0 |
| 44 | 5 | 5 | 5 | 5 | 0 | 0 | 0 | 0 | 0 |
| 45 | 5 | 5 | 4 | 5 | 0 | 0 | 0 | 0 | 0 |
| 46 | 5 | 5 | 5 | 5 | 0 | 0 | 0 | 0 | 0 |
| 47 | 5 | 5 | 5 | 5 | 0 | 0 | 0 | 0 | 0 |
| 48 | 5 | 5 | 5 | 5 | 0 | 0 | 0 | 0 | 0 |
| 49 | 5 | 5 | 5 | 4 | 0 | 0 | 0 | 0 | 0 |
| 50 | 5 | 5 | 4 | 4 | 0 | 0 | 0 | 0 | 0 |
| 51 | 4 | 5 | 4 | 4 | 0 | 0 | 0 | 0 | 0 |
| 52 | 5 | 5 | 5 | 5 | 0 | 0 | 0 | 0 | 0 |
| 53 | 4 | 4 | 5 | 4 | 0 | 0 | 0 | 0 | 0 |
| 54 | 4 | 5 | 4 | 4 | 0 | 0 | 0 | 0 | 0 |
| 55 | 5 | 5 | 4 | 5 | 0 | 0 | 0 | 0 | 0 |
| 56 | 5 | 5 | 5 | 5 | 0 | 0 | 0 | 0 | 0 |
| 57 | 5 | 5 | 5 | 4 | 0 | 0 | 0 | 0 | 0 |
| 58 | 4 | 5 | 4 | 4 | 0 | 0 | 0 | 0 | 0 |
| 59 | 4 | 4 | 4 | 4 | 0 | 0 | 0 | 0 | 0 |
| 60 | 4 | 4 | 5 | 4 | 0 | 0 | 0 | 0 | 0 |
| 61 | 4 | 4 | 4 | 4 | 0 | 0 | 0 | 0 | 0 |
| 62 | 5 | 5 | 4 | 4 | 0 | 0 | 0 | 0 | 0 |
| 63 | 5 | 5 | 4 | 4 | 0 | 0 | 0 | 0 | 0 |
| 64 | 5 | 5 | 5 | 4 | 0 | 0 | 0 | 0 | 0 |
| 65 | 5 | 5 | 5 | 5 | 0 | 0 | 0 | 0 | 0 |
| 66 | 5 | 5 | 4 | 5 | 0 | 0 | 0 | 0 | 0 |
| 67 | 5 | 4 | 4 | 4 | 0 | 0 | 0 | 0 | 0 |
| 68 | 4 | 5 | 4 | 4 | 0 | 0 | 0 | 0 | 0 |
| 69 | 4 | 5 | 4 | 4 | 0 | 0 | 0 | 0 | 0 |
| 70 | 5 | 5 | 5 | 5 | 0 | 0 | 0 | 0 | 0 |
| 71 | 5 | 5 | 4 | 4 | 0 | 0 | 0 | 0 | 0 |
| 72 | 4 | 5 | 5 | 4 | 0 | 0 | 0 | 0 | 0 |
| 73 | 5 | 4 | 4 | 4 | 0 | 0 | 0 | 0 | 0 |
| 74 | 5 | 5 | 5 | 5 | 0 | 0 | 0 | 0 | 0 |
| 75 | 4 | 5 | 4 | 4 | 0 | 0 | 0 | 0 | 0 |
| 76 | 4 | 4 | 4 | 4 | 0 | 0 | 0 | 0 | 0 |
| 77 | 5 | 5 | 5 | 5 | 0 | 0 | 0 | 0 | 0 |
| 78 | 5 | 5 | 5 | 4 | 0 | 0 | 0 | 0 | 0 |
| 79 | 5 | 5 | 5 | 5 | 0 | 0 | 0 | 0 | 0 |
| 80 | 5 | 5 | 5 | 5 | 0 | 0 | 0 | 0 | 0 |
| 81 | 5 | 5 | 4 | 4 | 0 | 0 | 0 | 0 | 0 |
| 82 | 5 | 5 | 5 | 4 | 0 | 0 | 0 | 0 | 0 |
| 83 | 5 | 5 | 5 | 5 | 0 | 0 | 0 | 0 | 0 |
| 84 | 4 | 5 | 4 | 4 | 0 | 0 | 0 | 0 | 0 |
| 85 | 4 | 5 | 4 | 4 | 0 | 0 | 0 | 0 | 0 |
| 86 | 5 | 5 | 5 | 4 | 0 | 0 | 0 | 0 | 0 |
| 87 | 5 | 5 | 4 | 5 | 0 | 0 | 0 | 0 | 0 |
| 88 | 4 | 4 | 4 | 4 | 0 | 0 | 0 | 0 | 0 |
| 89 | 5 | 5 | 5 | 5 | 0 | 0 | 0 | 0 | 0 |
| 90 | 4 | 5 | 4 | 4 | 0 | 0 | 0 | 0 | 0 |
| 91 | 5 | 5 | 4 | 4 | 0 | 0 | 0 | 0 | 0 |
| 92 | 4 | 5 | 4 | 4 | 0 | 0 | 0 | 0 | 0 |
| 93 | 5 | 5 | 4 | 4 | 0 | 0 | 0 | 0 | 0 |
| 94 | 5 | 5 | 4 | 4 | 0 | 0 | 0 | 0 | 0 |
| 95 | 4 | 5 | 4 | 4 | 0 | 0 | 0 | 0 | 0 |
| 96 | 4 | 5 | 4 | 4 | 0 | 0 | 0 | 0 | 0 |
| 97 | 4 | 5 | 4 | 4 | 0 | 0 | 0 | 0 | 0 |
| 98 | 5 | 5 | 4 | 4 | 0 | 0 | 0 | 0 | 0 |
| 99 | 4 | 4 | 5 | 4 | 0 | 0 | 0 | 0 | 0 |
| 100 | 4 | 5 | 5 | 4 | 0 | 0 | 0 | 0 | 0 |
| 101 | 5 | 5 | 5 | 4 | 0 | 0 | 0 | 0 | 0 |
| 102 | 4 | 4 | 4 | 4 | 0 | 0 | 0 | 0 | 0 |
| 103 | 4 | 5 | 4 | 4 | 0 | 0 | 0 | 0 | 0 |
| 104 | 5 | 4 | 5 | 5 | 0 | 0 | 0 | 0 | 0 |
| 105 | 5 | 5 | 5 | 4 | 0 | 0 | 0 | 0 | 0 |
| 106 | 4 | 5 | 5 | 5 | 0 | 0 | 0 | 0 | 0 |
| 107 | 4 | 5 | 5 | 4 | 0 | 0 | 0 | 0 | 0 |
| 108 | 5 | 5 | 5 | 4 | 0 | 0 | 0 | 0 | 0 |
| 109 | 4 | 5 | 4 | 4 | 0 | 0 | 0 | 0 | 0 |
| 110 | 5 | 4 | 4 | 4 | 0 | 0 | 0 | 0 | 0 |
| 111 | 4 | 4 | 5 | 5 | 0 | 0 | 0 | 0 | 0 |
| 112 | 4 | 5 | 4 | 4 | 0 | 0 | 0 | 0 | 0 |
| 113 | 4 | 5 | 4 | 4 | 0 | 0 | 0 | 0 | 0 |

TABLE 4-continued

| | Herbicidal effect on weeds in farm-field | | | | Phyto-toxicity to crop plants | | | | |
|---|---|---|---|---|---|---|---|---|---|
| | Crabgrass | Common lambsquarters | Pigweed | Smartweed | Soya bean | Sugar beet | Radish | Wheat | Maize |
| 114 | 4 | 4 | 4 | 4 | 0 | 0 | 0 | 0 | 0 |
| 115 | 4 | 5 | 4 | 4 | 0 | 0 | 0 | 0 | 0 |
| 116 | 4 | 4 | 4 | 4 | 0 | 0 | 0 | 0 | 0 |
| 117 | 4 | 5 | 4 | 4 | 0 | 0 | 0 | 0 | 0 |
| 118 | 4 | 5 | 5 | 4 | 0 | 0 | 0 | 0 | 0 |
| 119 | 4 | 5 | 4 | 4 | 0 | 0 | 0 | 0 | 0 |
| 120 | 5 | 5 | 5 | 4 | 0 | 0 | 0 | 0 | 0 |
| 121 | 4 | 5 | 4 | 4 | 0 | 0 | 0 | 0 | 0 |
| 122 | 4 | 5 | 5 | 4 | 0 | 0 | 0 | 0 | 0 |
| 123 | 4 | 4 | 4 | 4 | 0 | 0 | 0 | 0 | 0 |
| 124 | 5 | 5 | 5 | 5 | 0 | 0 | 0 | 1 | 0 |
| 125 | 5 | 5 | 5 | 4 | 0 | 0 | 0 | 0 | 0 |
| 126 | 5 | 5 | 5 | 5 | 0 | 0 | 0 | 1 | 0 |
| 127 | 5 | 4 | 4 | 4 | 0 | 0 | 0 | 0 | 0 |
| 128 | 5 | 5 | 5 | 5 | 0 | 0 | 0 | 0 | 0 |
| 129 | 5 | 5 | 5 | 5 | 0 | 0 | 0 | 0 | 0 |
| 130 | 5 | 5 | 4 | 5 | 0 | 0 | 0 | 0 | 0 |
| 131 | 5 | 5 | 4 | 4 | 0 | 0 | 0 | 0 | 0 |
| 132 | 5 | 5 | 4 | 4 | 0 | 0 | 0 | 0 | 0 |
| 133 | 5 | 5 | 4 | 5 | 0 | 0 | 0 | 0 | 0 |
| 134 | 4 | 5 | 4 | 4 | 0 | 0 | 0 | 0 | 0 |
| 135 | 5 | 5 | 4 | 4 | 0 | 0 | 0 | 0 | 0 |
| 136 | 5 | 5 | 5 | 5 | 0 | 0 | 0 | 0 | 0 |
| 137 | 5 | 5 | 4 | 5 | 0 | 0 | 0 | 0 | 0 |
| 138 | 5 | 5 | 5 | 5 | 0 | 0 | 1 | 1 | 1 |
| 139 | 5 | 5 | 5 | 5 | 0 | 0 | 0 | 0 | 0 |
| 140 | 5 | 5 | 5 | 5 | 0 | 0 | 0 | 0 | 0 |
| 141 | 5 | 5 | 5 | 5 | 0 | 0 | 0 | 0 | 0 |
| 142 | 5 | 5 | 5 | 5 | 0 | 0 | 0 | 0 | 0 |
| 143 | 5 | 5 | 5 | 5 | 0 | 0 | 0 | 0 | 0 |
| 144 | 4 | 4 | 4 | 5 | 0 | 0 | 0 | 0 | 0 |
| 145 | 5 | 4 | 4 | 4 | 0 | 0 | 0 | 0 | 0 |
| 146 | 4 | 5 | 5 | 5 | 0 | 0 | 0 | 0 | 0 |
| 147 | 5 | 5 | 5 | 4 | 0 | 0 | 0 | 0 | 0 |
| 148 | 5 | 5 | 5 | 4 | 0 | 0 | 0 | 0 | 0 |
| 149 | 4 | 4 | 4 | 5 | 0 | 0 | 0 | 0 | 0 |
| 150 | 4 | 4 | 4 | 4 | 0 | 0 | 0 | 0 | 0 |
| 151 | 5 | 4 | 4 | 5 | 0 | 0 | 0 | 0 | 0 |
| 152 | 5 | 5 | 5 | 5 | 0 | 0 | 0 | 0 | 0 |
| 153 | 4 | 5 | 4 | 5 | 0 | 0 | 0 | 0 | 0 |
| 154 | 5 | 5 | 5 | 5 | 0 | 0 | 0 | 0 | 0 |
| 155 | 5 | 4 | 4 | 5 | 0 | 0 | 0 | 0 | 0 |
| 156 | 4 | 5 | 4 | 5 | 0 | 0 | 0 | 0 | 0 |
| 157 | 4 | 4 | 4 | 4 | 0 | 0 | 0 | 0 | 0 |
| 158 | 4 | 5 | 5 | 5 | 0 | 0 | 0 | 0 | 0 |
| 159 | 4 | 4 | 4 | 4 | 0 | 0 | 0 | 0 | 0 |
| 160 | 5 | 5 | 4 | 5 | 0 | 0 | 0 | 0 | 0 |
| 161 | 4 | 4 | 5 | 5 | 0 | 0 | 0 | 0 | 0 |
| 162 | 5 | 4 | 4 | 4 | 0 | 0 | 0 | 0 | 0 |
| 163 | 5 | 4 | 4 | 4 | 0 | 0 | 0 | 0 | 0 |
| 164 | 4 | 4 | 4 | 5 | 0 | 0 | 0 | 0 | 0 |
| 165 | 4 | 4 | 4 | 4 | 0 | 0 | 0 | 0 | 0 |
| 166 | 5 | 4 | 4 | 4 | 0 | 0 | 0 | 0 | 0 |
| 167 | 5 | 5 | 4 | 5 | 0 | 0 | 0 | 0 | 0 |
| 168 | 4 | 4 | 4 | 4 | 0 | 0 | 0 | 0 | 0 |
| 169 | 4 | 5 | 4 | 5 | 0 | 0 | 0 | 0 | 0 |
| 170 | 4 | 4 | 4 | 4 | 0 | 0 | 0 | 0 | 0 |
| 171 | 5 | 4 | 5 | 5 | 0 | 0 | 0 | 0 | 0 |
| 172 | 5 | 5 | 4 | 5 | 0 | 0 | 0 | 0 | 0 |
| 173 | 5 | 4 | 4 | 4 | 0 | 0 | 0 | 0 | 0 |
| 174 | 5 | 5 | 5 | 5 | 0 | 0 | 0 | 0 | 0 |
| 175 | 5 | 5 | 4 | 5 | 0 | 0 | 0 | 0 | 0 |
| 176 | 5 | 5 | 5 | 5 | 0 | 0 | 0 | 0 | 0 |
| 177 | 5 | 5 | 4 | 5 | 0 | 0 | 0 | 0 | 0 |
| 178 | 4 | 4 | 5 | 4 | 0 | 0 | 0 | 0 | 0 |
| 179 | 4 | 5 | 4 | 4 | 0 | 0 | 0 | 0 | 0 |
| 180 | 4 | 4 | 4 | 4 | 0 | 0 | 0 | 0 | 0 |
| 181 | 5 | 5 | 4 | 5 | 0 | 0 | 0 | 0 | 0 |
| 182 | 4 | 5 | 4 | 5 | 0 | 0 | 0 | 0 | 0 |
| 183 | 5 | 5 | 5 | 5 | 0 | 0 | 0 | 0 | 0 |
| 184 | 5 | 5 | 5 | 4 | 0 | 0 | 0 | 0 | 0 |
| 185 | 5 | 5 | 5 | 5 | 0 | 0 | 0 | 0 | 0 |
| 186 | 4 | 4 | 4 | 4 | 0 | 0 | 0 | 0 | 0 |
| 187 | 5 | 5 | 5 | 4 | 0 | 0 | 0 | 0 | 0 |
| 188 | 4 | 5 | 4 | 4 | 0 | 0 | 0 | 0 | 0 |
| 189 | 5 | 5 | 5 | 4 | 0 | 0 | 0 | 0 | 0 |
| 190 | 4 | 4 | 4 | 4 | 0 | 0 | 0 | 0 | 0 |
| 191 | 4 | 4 | 5 | 4 | 0 | 0 | 0 | 0 | 0 |
| 192 | 5 | 4 | 5 | 5 | 0 | 0 | 0 | 0 | 0 |
| 193 | 4 | 4 | 4 | 4 | 0 | 0 | 0 | 0 | 0 |

TABLE 4-continued

|  | Herbicidal effect on weeds in farm-field | | | | Phyto-toxicity to crop plants | | | | |
| --- | --- | --- | --- | --- | --- | --- | --- | --- | --- |
|  | Crabgrass | Common lambsquarters | Pigweed | Smartweed | Soya bean | Sugar beet | Radish | Wheat | Maize |
| 194 | 4 | 4 | 4 | 4 | 0 | 0 | 0 | 0 | 0 |
| 195 | 4 | 4 | 4 | 4 | 0 | 0 | 0 | 0 | 0 |
| 196 | 4 | 5 | 4 | 4 | 0 | 0 | 0 | 0 | 0 |
| 197 | 5 | 5 | 4 | 5 | 0 | 0 | 0 | 0 | 0 |
| 198 | 4 | 4 | 4 | 4 | 0 | 0 | 0 | 0 | 0 |
| 199 | 4 | 4 | 5 | 5 | 0 | 0 | 0 | 0 | 0 |
| 200 | 4 | 4 | 4 | 4 | 0 | 0 | 0 | 0 | 0 |
| 201 | 4 | 4 | 4 | 4 | 0 | 0 | 0 | 0 | 0 |
| 202 | 4 | 5 | 4 | 5 | 0 | 0 | 0 | 0 | 0 |
| 203 | 5 | 5 | 5 | 5 | 0 | 0 | 0 | 0 | 0 |
| 204 | 5 | 5 | 4 | 5 | 0 | 0 | 0 | 0 | 0 |
| 205 | 5 | 5 | 5 | 5 | 0 | 0 | 0 | 0 | 0 |
| 206 | 5 | 5 | 5 | 5 | 0 | 0 | 0 | 0 | 0 |
| 207 | 4 | 4 | 5 | 5 | 0 | 0 | 0 | 0 | 0 |
| 208 | 4 | 5 | 4 | 5 | 0 | 0 | 0 | 0 | 0 |
| 209 | 4 | 5 | 4 | 5 | 0 | 0 | 0 | 0 | 0 |
| Comparative compound | | | | | | | | | |
| A | 3 | 3 | 2 | 1 | 0 | 0 | 0 | 1 | 1 |
| B | 3 | 3 | 1 | 0 | 0 | 0 | 0 | 1 | 0 |
| C | 0 | 1 | 1 | 0 | 0 | 0 | 0 | 0 | 0 |
| D | 0 | 1 | 0 | 0 | 0 | 0 | 0 | 0 | 0 |
| F | 4 | 3 | 3 | 3 | 1 | 1 | 1 | 2 | 2 |

(Notes 1):- Comparative Compounds A to D shown in Table 4 above are same as those identified for Table 2.

(Notes 2): Comparative compound F:

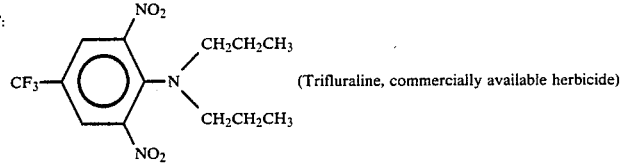

(Trifluraline, commercially available herbicide)

TEST EXAMPLE 4

This test was to evaluate the herbicidal effects of the compounds under test on the weeds predominant in the non-irrigated farm field of various crop plants, as well as the phytotoxicity of the compounds to crop plant when the compounds were applied at low rates of application of 50, 25 or 12.5 g of the active compound per 10 ares.

The procedure of Test Example 3 above was repeated, except that the herbicidal treatment of the weeds predominant in the farm field (non-irrigated) was effected by applying the test compounds at low rates. The herbicidal effects on the weeds and the phytotoxicity to crop plants were assessed in the same way as in Test Example 3 and with the same gradings as set out in Test Example 1 above. The test results obtained are shown in Table 5 below.

TABLE 5

| Test compound No. | Rate of application of active compound (g/10 ares) | Herbicidal effect on weeds in farm-field | | | | Phyto-toxicity to crop plants | | | | |
| --- | --- | --- | --- | --- | --- | --- | --- | --- | --- | --- |
|  |  | Crab-grass | Common lamb-squarters | Pig-weed | Smart-weed | Soya bean | Sugar beet | Radish | Wheat | Maize |
| 5 | 50 | 5 | 5 | 5 | 5 | 0 | 0 | 0 | 0 | 0 |
|  | 25 | 5 | 5 | 5 | 4 | 0 | 0 | 0 | 0 | 0 |
|  | 12.5 | 4 | 5 | 4 | 4 | 0 | 0 | 0 | 0 | 0 |
| 15 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 4 | 5 | 4 | 4 | 0 | 0 | 0 | 0 | 0 |
| 17 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 5 | 5 | 4 | 4 | 0 | 0 | 0 | 0 | 0 |
| 21 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 5 | 5 | 5 | 5 | 0 | 0 | 0 | 0 | 0 |
| 27 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 5 | 5 | 5 | 4 | 0 | 0 | 0 | 0 | 0 |
| 33 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 5 | 5 | 5 | 5 | 0 | 0 | 0 | 0 | 0 |
| 34 | 50 | 5 | 5 | 5 | 5 | 0 | 0 | 0 | 0 | 0 |
|  | 25 | 5 | 5 | 5 | 5 | 0 | 0 | 0 | 0 | 0 |
|  | 12.5 | 5 | 5 | 5 | 5 | 0 | 0 | 0 | 0 | 0 |
| 36 | 50 | 5 | 5 | 5 | 4 | 0 | 0 | 0 | 0 | 0 |
|  | 25 | 4 | 5 | 4 | 4 | 0 | 0 | 0 | 0 | 0 |
|  | 12.5 | 4 | 4 | 4 | 4 | 0 | 0 | 0 | 0 | 0 |
| 37 | 50 | 5 | 5 | 5 | 5 | 0 | 0 | 0 | 0 | 0 |
|  | 25 | 4 | 5 | 4 | 4 | 0 | 0 | 0 | 0 | 0 |
|  | 12.5 | 4 | 4 | 4 | 4 | 0 | 0 | 0 | 0 | 0 |

TABLE 5-continued

| Test compound No. | Rate of application of active compound (g/10 ares) | Herbicidal effect on weeds in farm-field | | | | Phyto-toxicity to crop plants | | | | |
|---|---|---|---|---|---|---|---|---|---|---|
| | | Crab-grass | Common lamb-squarters | Pig-weed | Smart-weed | Soya bean | Sugar beet | Radish | Wheat | Maize |
| 38 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 41 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 44 | 50 | 5 | 5 | 5 | 5 | 0 | 0 | 0 | 0 | 0 |
| | 25 | 5 | 5 | 4 | 4 | 0 | 0 | 0 | 0 | 0 |
| | 12.5 | 4 | 5 | 4 | 4 | 0 | 0 | 0 | 0 | 0 |
| 46 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 47 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 48 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 52 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 4 | 4 | 4 | 0 | 0 | 0 | 0 | 0 |
| 56 | 50 | 5 | 5 | 5 | 5 | 0 | 0 | 0 | 0 | 0 |
| | 25 | 5 | 4 | 5 | 5 | 0 | 0 | 0 | 0 | 0 |
| | 12.5 | 5 | 4 | 5 | 4 | 0 | 0 | 0 | 0 | 0 |
| 65 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 4 | 0 | 0 | 0 | 0 | 0 |
| 70 | 50 | 5 | 5 | 5 | 4 | 0 | 0 | 0 | 0 | 0 |
| | 25 | 4 | 5 | 4 | 4 | 0 | 0 | 0 | 0 | 0 |
| | 12.5 | 4 | 4 | 4 | 4 | 0 | 0 | 0 | 0 | 0 |
| 74 | 50 | 5 | 5 | 4 | 5 | 0 | 0 | 0 | 0 | 0 |
| | 25 | 4 | 5 | 4 | 4 | 0 | 0 | 0 | 0 | 0 |
| | 12.5 | 4 | 4 | 4 | 4 | 0 | 0 | 0 | 0 | 0 |
| 77 | 50 | 5 | 5 | 5 | 5 | 0 | 0 | 0 | 0 | 0 |
| | 25 | 5 | 5 | 4 | 4 | 0 | 0 | 0 | 0 | 0 |
| | 12.5 | 4 | 4 | 4 | 4 | 0 | 0 | 0 | 0 | 0 |
| 79 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 80 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 83 | 50 | 5 | 5 | 5 | 5 | 0 | 0 | 0 | 0 | 0 |
| | 25 | 5 | 5 | 5 | 4 | 0 | 0 | 0 | 0 | 0 |
| | 12.5 | 4 | 4 | 4 | 4 | 0 | 0 | 0 | 0 | 0 |
| 89 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 4 | 4 | 4 | 0 | 0 | 0 | 0 | 0 |
| 124 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 3 | 4 | 4 | 5 | 0 | 0 | 0 | 0 | 0 |
| 126 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 5 | 4 | 5 | 0 | 0 | 0 | 0 | 0 |
| 128 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 5 | 3 | 5 | 0 | 0 | 0 | 0 | 0 |
| 129 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 136 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 5 | 5 | 5 | 0 | 0 | 0 | 0 | 0 |
| 138 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 139 | 50 | 5 | 5 | 5 | 5 | 0 | 0 | 0 | 0 | 0 |
| | 25 | 4 | 4 | 4 | 5 | 0 | 0 | 0 | 0 | 0 |
| | 12.5 | 4 | 4 | 4 | 4 | 0 | 0 | 0 | 0 | 0 |
| 140 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 4 | 5 | 0 | 0 | 0 | 0 | 0 |
| 141 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 4 | 4 | 5 | 0 | 0 | 0 | 0 | 0 |
| 142 | 50 | 5 | 5 | 5 | 5 | 0 | 0 | 0 | 0 | 0 |
| | 25 | 4 | 4 | 4 | 5 | 0 | 0 | 0 | 0 | 0 |

TABLE 5-continued

| Test compound No. | Rate of application of active compound (g/10 ares) | Herbicidal effect on weeds in farm-field | | | | Phyto-toxicity to crop plants | | | | |
|---|---|---|---|---|---|---|---|---|---|---|
| | | Crab-grass | Common lamb-squarters | Pig-weed | Smart-weed | Soya bean | Sugar beet | Radish | Wheat | Maize |
| | 12.5 | 4 | 4 | 4 | 4 | 0 | 0 | 0 | 0 | 0 |
| 143 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 5 | 4 | 5 | 0 | 0 | 0 | 0 | 0 |
| 152 | 50 | 5 | 5 | 5 | 5 | 0 | 0 | 0 | 0 | 0 |
| | 25 | 5 | 4 | 5 | 5 | 0 | 0 | 0 | 0 | 0 |
| | 12.5 | 4 | 4 | 4 | 4 | 0 | 0 | 0 | 0 | 0 |
| 154 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 4 | 4 | 5 | 0 | 0 | 0 | 0 | 0 |
| 174 | 50 | 5 | 5 | 5 | 5 | 0 | 0 | 0 | 0 | 0 |
| | 25 | 5 | 4 | 5 | 5 | 0 | 0 | 0 | 0 | 0 |
| | 12.5 | 4 | 4 | 4 | 4 | 0 | 0 | 0 | 0 | 0 |
| 176 | 50 | 5 | 5 | 5 | 5 | 0 | 0 | 0 | 0 | 0 |
| | 25 | 5 | 5 | 4 | 5 | 0 | 0 | 0 | 0 | 0 |
| | 12.5 | 4 | 4 | 4 | 4 | 0 | 0 | 0 | 0 | 0 |
| 183 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 185 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 4 | 5 | 0 | 0 | 0 | 0 | 0 |
| 203 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 4 | 5 | 0 | 0 | 0 | 0 | 0 |
| 205 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 5 | 5 | 5 | 5 | 0 | 0 | 0 | 0 | 0 |
| 206 | 50 | 5 | 5 | 5 | 5 | 0 | 0 | 0 | 0 | 0 |
| | 25 | 5 | 5 | 5 | 5 | 0 | 0 | 0 | 0 | 0 |
| | 12.5 | 4 | 4 | 4 | 5 | 0 | 0 | 0 | 0 | 0 |
| Comparative compound A | 50 | 2 | 2 | 2 | 0 | 0 | 0 | 0 | 1 | 0 |
| | 25 | 1 | 0 | 0 | 0 | 0 | 0 | 0 | 0 | 0 |
| | 12.5 | 0 | 0 | 0 | 0 | 0 | 0 | 0 | 0 | 0 |
| Comparative compound B | 50 | 2 | 2 | 0 | 0 | 0 | 0 | 0 | 1 | 0 |
| | 25 | 1 | 1 | 0 | 0 | 0 | 0 | 0 | 0 | 0 |
| | 12.5 | 0 | 0 | 0 | 0 | 0 | 0 | 0 | 0 | 0 |
| Comparative compound C | 50 | 0 | 1 | 0 | 0 | 0 | 0 | 0 | 0 | 0 |
| | 25 | 0 | 0 | 0 | 0 | 0 | 0 | 0 | 0 | 0 |
| | 12.5 | 0 | 0 | 0 | 0 | 0 | 0 | 0 | 0 | 0 |
| Comparative compound D | 50 | 0 | 0 | 0 | 0 | 0 | 0 | 0 | 0 | 0 |
| | 25 | 0 | 0 | 0 | 0 | 0 | 0 | 0 | 0 | 0 |
| | 12.5 | 0 | 0 | 0 | 0 | 0 | 0 | 0 | 0 | 0 |
| Comparative compound F | 50 | 3 | 2 | 2 | 2 | 1 | 0 | 0 | 2 | 1 |
| | 25 | 3 | 1 | 1 | 0 | 0 | 0 | 0 | 1 | 0 |
| | 12.5 | 0 | 0 | 0 | 0 | 0 | 0 | 0 | 0 | 0 |

Notes:
Comparative compounds A to D shown in Table 5 above are the same as those indentified for Table 2 and Comparative compound F is the same as that identified for Table 4 above.

We claim:

1. A pyrazole derivative represented by the formula

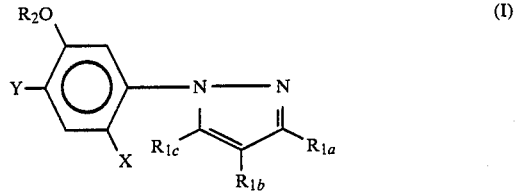

(I)

wherein $R_{1a}$, $R_{1b}$ and $R_{1c}$ are each a hydrogen atom, a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group;

$R_2$ is a hydrogen atom, a (lower)alkyl group, a (lower) alkenyl group, a (lower)alkynyl group, a (lower)alkoxy(lower) alkyl group, a (lower)alkylthio(lower)alkyl group, a (lower) alkylcarbonyl(-lower)alkyl group, a (lower)alkoxycarbonyl(lower)alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower)alkyl-substituted phenylsulfonyl group, and X and Y are the same or different and each are a halogen atom.

2. A compound as claimed in claim 1, which is a compound of the formula

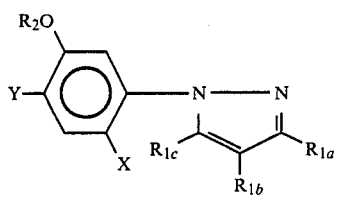

where
- $R_{1a}$, $R_{1b}$ and $R_{1c}$ are each a hydrogen atom, a halogen atom, a (lower)alkyl group, a (lower)alkenyl group or a (lower)alkynyl group
- $R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower) alkoxycarbonyl(lower)alkyl group, a (lower)alkylthiocarbonyl(lower)alkyl group or a cyano(lower)alkyl group, and X and Y are the same or different and each are a halogen atom.

3. A compound as claimed in claim 1, which is a compound of the formula

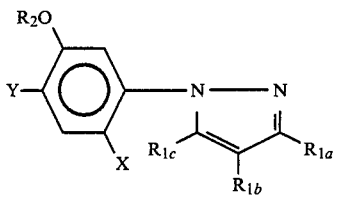

where
- $R_{1a}$, $R_{1b}$ and $R_{1c}$ are each a hydrogen atom, a halogen atom, a (lower)alkyl group, a (lower)alkenyl group or a (lower)alkynyl group
- $R_2$ is a (lower)alkylsulfonyl group, phenylsulfonyl group, a halogen-substituted phenylsulfonyl group or a (lower)alkyl-substituted phenylsulfonyl group, and
- X and Y are the same or different and each are a halogen atom.

4. A compound as claimed in claim 1, which is a compound of the formula

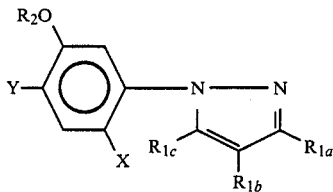

wherein
- $R_{1a}$, $R_{1b}$ and $R_{1c}$ are each a hydrogen atom, a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group; provided that at least one of $R_{1a}$ $R_{1b}$ and $R_{1c}$ is or are a halo-(lower)alkyl group, a nitro group, an amino group, a (lower)alkylcarbonylamino group, a (lower)alkoxycarbonylamino group, a mono-(lower)alkylaminocarbonylamino group or a di-(lower)alkylaminocarbonylamino group,
- $R_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower alkoxycarbonyl(lower)alkyl group, a (lower)alkylthiocarbonyl(lower)alkyl group or a cyano(lower)alkyl group, and
- X and Y are the same or different and each are a halogen atom.

5. A compound as claimed in claim 1, which is a compound of the formula

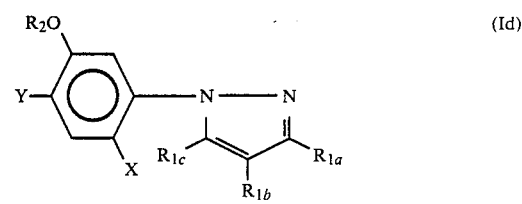

wherein
- $R_{1a}$, $R_{1b}$ and $R_{1c}$ are each a hydrogen atom, a halogen atom, a nitro group, an amino group, a (lower) alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group; provided that at least one of $R_{1a}$, $R_{1b}$ and $R_{1c}$ is or are a halo-(lower)alkyl group, a nitro group, an amino group, a (lower)alkylcarbonylamino group, a (lower)alkoxycarbonylamino group, a mono-(lower)alkylaminocarbonylamino group or a di-(lower)alkylaminocarbonylamino group,
- $R_2$ is a (lower)alkylsulfonyl group, phenylsulfonyl group, a halogen-substituted phenylsulfonyl group or a (lower)alkyl-substituted phenylsulfonyl group, and
- X and Y are the same or different and each are a halogen atom.

6. A compound as claimed in claim 1 or claim 2, which is a compound of the formula

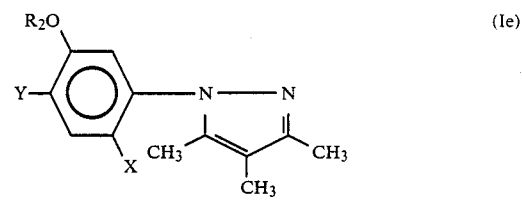

where
- $R_2$ is a (lower)alkyl group, a (lower)alkenyl group or a (lower)alkynyl group; and X and Y are the same or different and each are chlorine, bromine, fluorine or iodine atom.

7. A compound as claimed in claim 1 or claim 2, which is a compound of the formula

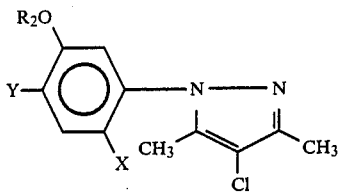

(If)

where

R$_2$ is a (lower)alkyl group, a (lower)alkenyl group or a (lower)alkynyl group; and X and Y are the same different and each are chlorine, bromine, fluorine or iodine atom.

8. A compound as claimed in claim 1 or claim 2, which is a compound of the formula

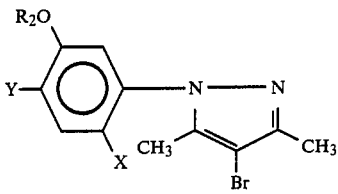

(Ig)

where

R$_2$ is a (lower)alkyl group, a (lower)alkenyl group or a (lower)alkynyl group; and X and Y are the same or different and each are chlorine, bromine, fluorine or iodine atom.

9. A compound as claimed in claim 1 or claim 4, which is a compound of the formula

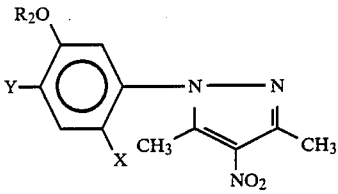

(Ih)

where

R$_2$ is a (lower)alkyl group, a (lower)alkenyl group or a (lower)alkynyl group; and X and Y are the same or different and each are chlorine, bromine, fluorine or iodine atom.

10. A compound as claimed in claim 1, which is 1-(2-fluoro-4-chloro-5-propargyloxyphenyl)-3,4,5-trimethylpyrazole.

11. A compound as claimed in claim 1, which is 1-(2-fluoro-4-chloro-5-propargyloxyphenyl)-3,5-dimethyl-4-chloropyrazole.

12. A compound as claimed in claim 1, which is 1-(2-fluoro-4-chloro-5-propargyloxyphenyl)-3,5-dimethyl-4-bromopyrazole.

13. A compound as claimed in claim 1, which is selected from:
1-(2-fluoro-4-chloro-5-allyloxyphenyl)-3,5-dimethyl-4-nitropyrazole,
1-(2-fluoro-4-chloro-5-propargyloxyphenyl)-3,5-dimethyl-4-nitropyrazole and
1-[2-fluoro-4-chloro-5-(1-methyl-2-propynyloxy)-phenyl]-3,5-dimethyl-4-nitropyrazole.

14. A herbicidal composition comprising an herbicidally effective amount of a compound of the formula

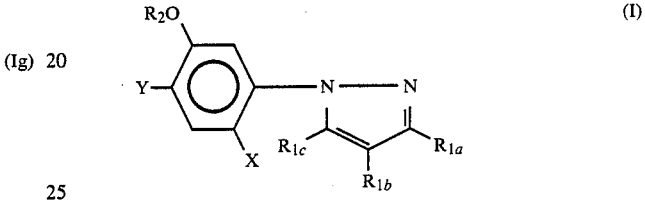

(I)

wherein

R$_{1a}$, R$_{1b}$ and R$_{1c}$ are each a hydrogen atom, a halogen atom, a nitro group, an amino group, a (lower)alkyl group, a halo-(lower)alkyl group, a (lower)alkenyl group, a (lower)alkynyl group, a (lower)alkylcarbonylamino group, a (lower)alkoxycarbonylamino group, a mono-(lower) alkylaminocarbonylamino group or a di-(lower)alkylaminocarbonylamino group;

R$_2$ is a hydrogen atom, a (lower)alkyl group, a (lower)alkenyl group, a (lower)alkynyl group, a (lower) alkoxy(lower)alkyl group, a (lower)alkylthio(lower)alkyl group, a (lower)alkylcarbonyl(lower)alkyl group, a (lower) alkoxycarbonyl(lower)alkyl group, a (lower)alkylthiocarbonyl(lower)alkyl group, a cyano(lower)alkyl group, a (lower)alkylsulfonyl group, phenylsulfonyl group, a halogen-substituted phenylsulfonyl group or a (lower) alkyl-substituted phenylsulfonyl group, and X and Y are the same or different and each are a halogen atom, in association with a solid or liquid carrier for the active ingredient.

15. A method of inhibiting the growth of unwanted weeds, which comprises applying to the weeds or to the locus thereof a herbicidally effective amount of the pyrazole derivative of the formula (I) as defined in claim 1.

* * * * *